(12) United States Patent
Haseba et al.

(10) Patent No.: US 6,248,260 B1
(45) Date of Patent: Jun. 19, 2001

(54) LIQUID-CRYSTAL COMPOUNDS HAVING FLUORINATED ALKYL GROUPS, LIQUID-CRYSTAL COMPOSITION, AND LIQUID-CRYSTAL DISPLAY ELEMENT

(75) Inventors: Yasuhiro Haseba; Kazutoshi Miyazawa; Shuichi Matsui; Hiroyuki Takeuchi; Yasuhiro Kubo; Fusayuki Takeshita; Etsuo Nakagawa, all of Chiba (JP)

(73) Assignee: Chisso Corporation, Osaka (JP)

( * ) Notice: Subject to any disclaimer, the term of this patent is extended or adjusted under 35 U.S.C. 154(b) by 0 days.

(21) Appl. No.: 09/355,285

(22) PCT Filed: Jan. 29, 1998

(86) PCT No.: PCT/JP98/00365

§ 371 Date: Jul. 28, 1999

§ 102(e) Date: Jul. 28, 1999

(87) PCT Pub. No.: WO98/32722

PCT Pub. Date: Jul. 30, 1998

(30) Foreign Application Priority Data

Jan. 29, 1997 (JP) .................................................. 9-029541

(51) Int. Cl.[7] .......................... C09K 19/12; C09K 19/30; C09K 19/08; C07C 22/00
(52) U.S. Cl. ............................... 252/299.66; 252/299.63; 570/129; 570/127; 570/144
(58) Field of Search ........................ 252/299.63, 299.66, 252/299.61

(56) References Cited

U.S. PATENT DOCUMENTS

| | | | | |
|---|---|---|---|---|
| 5,730,904 | * | 3/1998 | Bartmann et al. | 252/299.63 |
| 5,762,828 | * | 6/1998 | Tanaka et al. | 252/299.63 |
| 5,827,450 | * | 10/1998 | Numata et al. | 252/299.63 |
| 5,874,022 | * | 2/1999 | Kubo et al. | 252/299.01 |
| 5,948,319 | * | 9/1999 | Tanaka et al. | 252/299.66 |
| 5,951,913 | * | 9/1999 | Shimizu et al. | 252/299.61 |
| 5,980,778 | * | 11/1999 | Shimizu et al. | 252/299.61 |
| 5,985,171 | * | 11/1999 | Rieger et al. | 252/299.63 |
| 6,004,478 | * | 12/1999 | Shimizu et al. | 252/299.61 |

FOREIGN PATENT DOCUMENTS

| | | |
|---|---|---|
| 4142519 | 8/1992 | (DE) . |
| 4308028 | 9/1994 | (DE) . |
| 4329592 | 3/1995 | (DE) . |
| 19513007 | 10/1995 | (DE) . |
| 2-62834 | 3/1990 | (JP) . |
| 2-145531 | 6/1990 | (JP) . |
| 2-233626 | 9/1990 | (JP) . |
| 4-506361 | 5/1992 | (JP) . |
| 6-122636 | 5/1994 | (JP) . |
| 6-145082 | 5/1994 | (JP) . |
| 6-206836 | 7/1994 | (JP) . |
| 7-145099 | 6/1995 | (JP) . |
| 7-267885 | 10/1995 | (JP) . |
| 9-77703 | 3/1997 | (JP) . |
| 10-67694 | 3/1998 | (JP) . |
| 88/08441 | 11/1988 | (WO) . |
| 91/17135 | * | 11/1991 | (WO) . |

* cited by examiner

Primary Examiner—C. H. Kelly
(74) Attorney, Agent, or Firm—Wenderoth, Lind & Ponack, L.L.P.

(57) ABSTRACT

Provided are liquid crystalline compounds which are excellent in the miscibility with existing liquid crystalline compounds even at low temperatures and are electrically and chemically stable while having a high voltage holding ratio and a high $\Delta\epsilon$; liquid crystal compositions comprising the compound; and liquid crystal display devices fabricated by using the composition; the liquid crystalline compounds are expressed by the general formula (1)

(1)

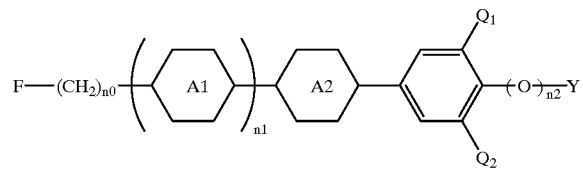

15 Claims, No Drawings

LIQUID-CRYSTAL COMPOUNDS HAVING FLUORINATED ALKYL GROUPS, LIQUID-CRYSTAL COMPOSITION, AND LIQUID-CRYSTAL DISPLAY ELEMENT

This application is a 371 application of International Application No. PCT/JP98/00365 field Jan. 29, 1998.

TECHNICAL FIELD

The present invention relates to liquid crystalline compounds and liquid crystal compositions. More specifically, the invention relates to liquid crystalline compounds having a fluoroalkyl group at both terminals and being preferable as component of liquid crystal compositions, particularly of liquid crystal compositions for TFT, liquid crystal compositions comprising the compound, and liquid crystal display devices fabricated by using the liquid crystal composition.

BACKGROUND ART

Liquid crystal display devices employ optical (refractive) anisotropy and dielectric anisotropy of liquid crystal substances, and are divided into various modes such as TN mode (twisted nematic mode), DS mode (dynamic scattering mode), G.H mode (guest-host mode), DAP (deformation of aligned phase mode), and STN mode (super twisted nematic mode) according to their display modes. Properties of liquid crystal substances suitable for each of the display mode are different. Recently, liquid crystal display devices particularly having a higher display quality are required, and demand for display devices of active matrix mode represented by TFT mode (thin film transistor mode) is increased in order to respond to the requirement. Liquid crystal substances used in display devices of any mode are necessary to be stable against moisture, air, heat, and light. Besides, the liquid crystal substances must exhibit a liquid crystal phase in a temperature range as large as possible with room temperature being its center, be low in viscosity, be excellent in miscibility with other liquid crystalline compounds (hereinafter used as a general term for the compounds having a liquid crystal phase and the compounds which do not impair a liquid crystal phase when mixed with other liquid crystal compounds) and liquid crystal compositions, have a high dielectric anisotropy value ($\Delta\epsilon$), and have an optimum optical anisotropy value ($\Delta n$). However, liquid crystal substances which completely satisfy such requirements by single compound have not been found, and it is a current situation that liquid crystal compositions obtained by mixing several to several tens kind of liquid crystalline compounds are used.

It is lately required in particular to liquid crystal display devices of TFT mode that they maintain a high contrast during frame time and can favorably be driven even at low temperatures. In order to cope with these requirements, advent of liquid crystalline compounds and liquid crystal compositions exhibiting a higher voltage holding ratio than that of conventional liquid crystal materials is expected for the former, and advent of liquid crystalline compounds which more hardly deposit crystals or develop smectic phase at low temperatures, that is, liquid crystalline compounds excellent in the miscibility with other liquid crystalline compounds and liquid crystal compositions at low temperatures is hoped for the latter.

Heretofore, as liquid crystal materials having a high voltage holding ratio and a high $\Delta\epsilon$, fluorine type compounds, for example, trifluorophenyl derivatives expressed by the formula (10) (Laid-open Japanese Patent Publication No. Hei 02-233626), and trifluoromethylphenyl derivatives expressed by the formula (11) and trifluoromethoxyphenyl derivatives expressed by the formula (12) (Laid-open Japanese Patent Publication No. Hei 04-506361) are known.

Whereas these compounds have an electron withdrawing group at one terminal, the alkyl chain length (total of the number of carbon atoms and the number of oxygen atom in the chain) in the group is 2 or less. Accordingly, these compounds readily deposit crystals or develop smectic phase at low temperatures when mixed with other liquid crystal substances.

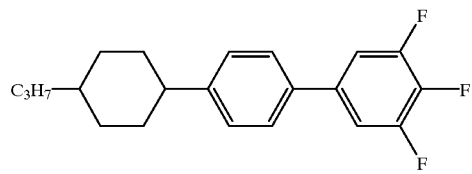

(10)

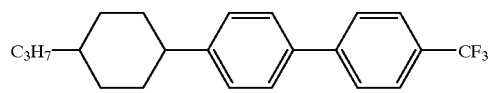

(11)

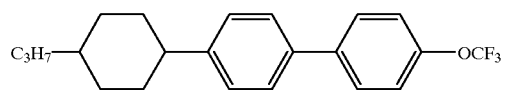

(12)

On the other hand, as component of liquid crystal compositions which makes excellent driving of liquid crystal display devices of TFT mode possible even at low temperatures, compounds a part of which is replaced by a fluorine substituted alkoxy group expressed by the formula (13) in which the number of carbon atom in the electron withdrawing group at one terminal is 2 (Laid-open Japanese Patent Publication No. Hei 7-145099) and compounds expressed by one of the formulas (14) to (18) in which the number of carbon atom described above is 2 or more (WO 88/08441, DE 4142519, DE 4329592, DE 4308028, and DE 19513007 in turn) are also known.

These compounds having an electron withdrawing group at one terminal are still insufficient as component of liquid crystal compositions for driving at low temperatures, and for instance, are liable to cause an extreme lowering in response speed and poor display at low temperatures.

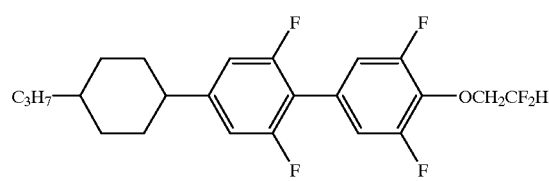

(13)

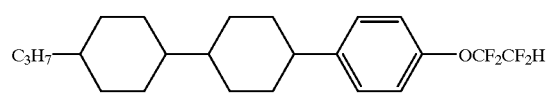

(14)

-continued

(15)
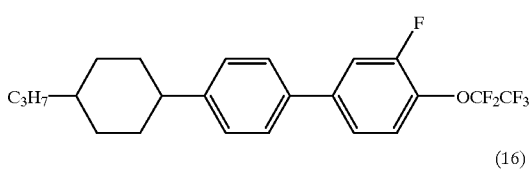

(16)
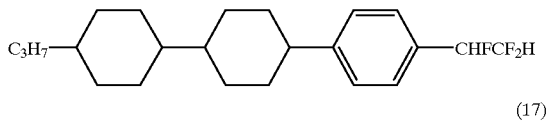

(17)
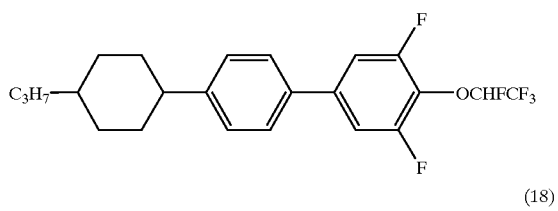

(18)
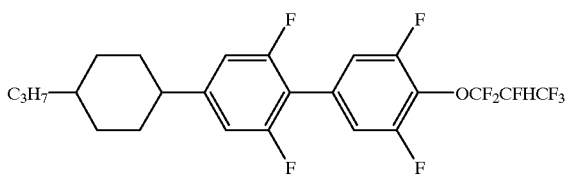

Further, compounds which are formed into a structure having an electron withdrawing group at both terminals by providing F, or an alkyl group or alkoxy group in which fluorine atom is introduced, for example, $CF_3$ or $OCF_3$ at the other terminal are known (Laid-open Japanese Patent Publication No. Hei 04-506817).

However, such compounds are not sufficient in the miscibility with other liquid crystals at low temperatures, and the compound expressed by the following formula (19) does not exhibit even a liquid crystal phase.

(19)
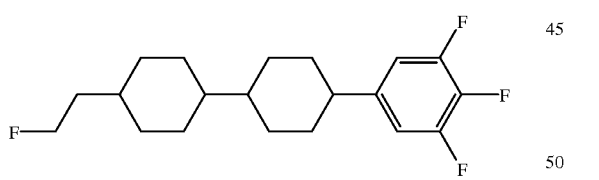

As described above, compounds excellent in the miscibility at low temperatures with other liquid crystals at low temperatures while having a high voltage holding ration and a high $\Delta\varepsilon$ have not been attained.

DISCLOSURE OF THE INVENTION

An object of the present invention is to eliminate the defects in the prior art described above. Another object of the present invention is to provide liquid crystalline compounds which are excellent in the miscibility with existing liquid crystalline compounds even at low temperatures, and electrically and chemically stable while having a high voltage holding ratio and a high $\Delta\varepsilon$, to provide liquid crystal compositions comprising the compound, and to provide liquid crystal display devices fabricated by using the composition.

As a result of diligent investigations by the present inventors, it has been found out that the compounds which are composed of a skeleton of two rings or three rings each of which rings is not linked through a bonding group, have a structure in which an electron withdrawing group is bonded at both terminals, the electron withdrawing group at one side is an alkyl chain having one fluorine atom at terminal and the group at the other side is one selected from fluoroalkyl chains and fluoroalkoxy chains are effective, leading to the accomplishment of the present invention.

That is, the present invention is summarized as follows:

(1) A liquid crystalline compound expressed by the general formula (1)

(1)
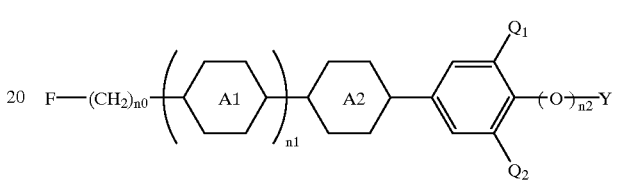

wherein n0 is an integer of 2 to 10; n1 and n2 are each independently 0 or 1; ring A1 and ring A2 each independently represent a group selected from the groups expressed by one of the formulas (a) to (i);

(a)

(b)

(c)
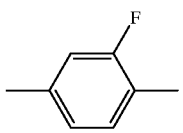

(d)
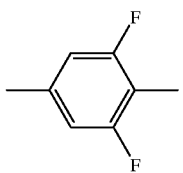

(e)
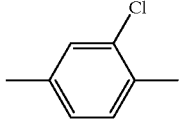

(f)
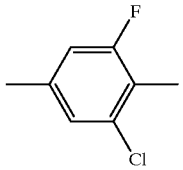

-continued (g)
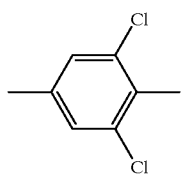

(h)
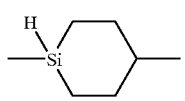

(i)
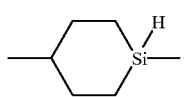

$Q_1$ and $Q_2$ each independently represent hydrogen atom, fluorine atom, or chlorine atom; Y represents a fluoroalkyl group having 2 to 7 carbon atoms; and each atom which constitutes the compound may be its isotope.

(2) The liquid crystalline compound recited in paragraph (1) above wherein n1 is 0.
(3) The liquid crystalline compound recited in paragraph (1) above wherein n1 is 1.
(4) The liquid crystalline compound recited in paragraph (1) above wherein n2 is 0.
(5) The liquid crystalline compound recited in paragraph (1) above wherein n2 is 1.
(6) The liquid crystalline compound recited in paragraph (1) above wherein n1 is 1 and ring A1 is a group selected from the groups expressed by any one of the formulas (a) to (d).

(a)

(b)
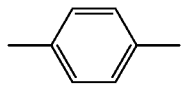

(c)
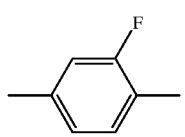

(d)
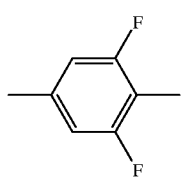

(7) A liquid crystal composition comprising at least one liquid crystalline compound recited in any one of paragraphs (1) to (6) above.
(8) A liquid crystal composition comprising, as a first component, at least one liquid crystalline compound recited in any one of paragraphs (1) to (6) above, and comprising, as a second component, at least one compound selected from the compounds expressed by any one of the general formulas (2), (3), and (4)

(2)
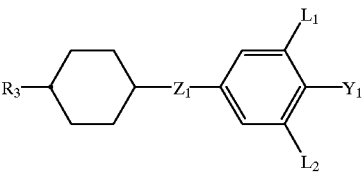

(3)
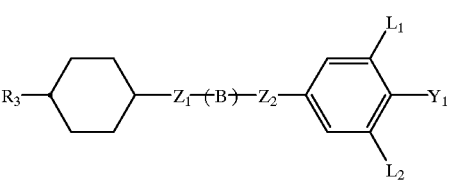

(4)
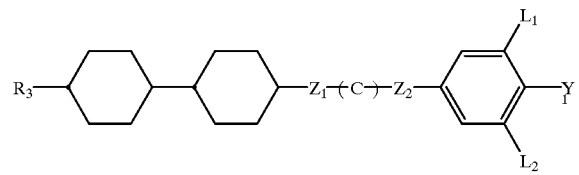

wherein $R_3$, $Y_1$, $L_1$, $L_2$, $Z_1$, and $Z_2$ may be the same or different among those general formulas; $R_3$ represents an alkyl group having 1 to 10 carbon atoms in which alkyl group one or not-adjacent two or more methylene groups may be replaced by oxygen atom or —CH=CH—, and any hydrogen atom may be replaced by fluorine atom; $Y_1$ represents fluorine atom, chlorine atom, $OCF_3$, $OCF_2H$, $CF_3$, $CF_2H$, $CFH_2$, $OCF_2CF_2H$, or $OCF_2CFHCF_3$; $L_1$ and $L_2$ each independently represent hydrogen atom or fluorine atom; $Z_1$ and $Z_2$ each independently represent —CH$_2$CH$_2$—, —CH$_2$CH$_2$CH$_2$CH$_2$—, —COO—, —CF$_2$O—, —OCF$_2$—, —CH=CH—, or single bond; ring B represents trans-1,4-cyclohexylene or 1,3-dioxane-2,5-diyl, or 1,4-phenylene in which hydrogen atom on the ring may be replaced by fluorine atom; ring C represents trans-1,4-cyclohexylene, or 1,4-phenylene in which hydrogen atom on the ring may be replaced by fluorine atom; and in the compounds expressed by each of those general formulas, any atom which constitutes those compounds may be replaced by its isotope.

(9) A liquid crystal composition comprising, as a first component, at least one liquid crystalline compound recited in any one of paragraphs (1) to (6) above, and comprising, as a second component, at least one compound selected from the compounds expressed by the general formula (5) and (6)

(5)
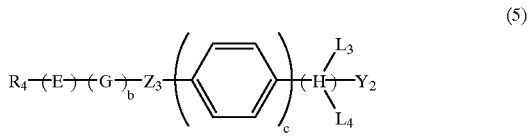

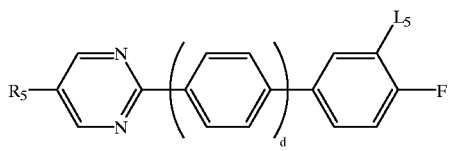

wherein $R_4$ and $R_5$ each independently represent an alkyl group having 1 to 10 carbon atoms in which alkyl group one or not-adjacent two or more methylene groups may be replaced by oxygen atom or —CH=CH—, and any hydrogen atom may be replaced by fluorine atom; $Y_2$ represents —CN group or —C≡C—CN; ring E represents trans-1,4-cyclohexylene, 1,4-phenylene, 1,3-dioxane-2,5-diyl, or pyrimidine-2,5-diyl; ring G represents trans-1,4-cyclohexylene, 1,4-phenylene in which hydrogen atom on the ring may be replaced by fluorine atom, or pyrimidine-2,5-diyl; ring H represents trans-1,4-cyclohexylene or 1,4-phenylene; $Z_3$ represents —CH$_2$CH$_2$——COO—, or single bond; $L_3$, $L_4$, and $L_5$ each independently represent hydrogen atom or fluorine atom; b, c, and d are each independently 0 or 1; and in the compounds expressed by each of those general formulas, each atom which constitutes those compounds may be its isotope.

(10) A liquid crystal composition comprising, as a first component, at least one liquid crystalline compound recited in any one of paragraphs (1) to (6) above, comprising, as a second component, at least one compound selected from the compounds expressed by any one of the general formulas (2), (3), and (4) described above, and comprising, as a third component, at least one compound selected from the compounds expressed by any one of the general formulas (7), (8), and (9)

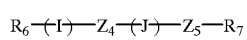  (7)

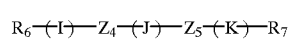  (8)

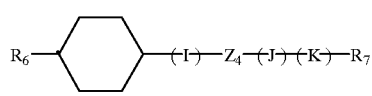  (9)

wherein $R_6$, $R_7$, I, J, and K may be the same or different among those general formulas; $R_6$ and $R_7$ each independently represent an alkyl group having 1 to 10 carbon atoms in which alkyl group one or not-adjacent two or more methylene groups may be replaced by oxygen atom or —CH=CH—, and any hydrogen atom may be replaced by fluorine atom; I, J, and K each independently represent trans-1,4-cyclohexylene or pyrimidine-2,5-diyl, or 1,4-phenylene in which hydrogen atom on the ring may be replaced by fluorine atom; $Z_4$ and $Z_5$ each independently represent —C≡C—, —COO—, —CH$_2$CH$_2$—, —CH=CH—, or single bond; and in the compounds expressed by each of those general formulas, each atom which constitutes those compounds may be its isotope.

(11) A liquid crystal composition comprising, as a first component, at least one liquid crystalline compound recited in any one of paragraphs (1) to (6) above, comprising, as a second component, at least one compound selected from the compounds expressed by the general formula (5) and (6) described above, and comprising, as a third component, at least one compound selected from the compounds expressed by any one of the general formulas (7), (8), and (9) described above.

(12) A liquid crystal composition comprising, as a first component, at least one liquid crystalline compound recited in any one of paragraphs (1) to (6) above, comprising, as a part of a second component, at least one compound selected from the compounds expressed by any one of the general formulas (2), (3), and (4) described above, comprising, as another part of the second component, at least one compound selected from the compounds expressed by the general formula (5) and (6) described above, and comprising, as a third component, at least one compound selected from the compounds expressed by any one of the general formulas (7), (8), and (9) described above.

(13) A liquid crystal composition recited in any one of paragraphs (7) to (12) above wherein the liquid crystal composition further comprises an optically active compound.

(14) A liquid crystal display device fabricated by using a liquid crystal composition recited in any one of paragraphs (7) to (13) above.

BEST MODE FOR CARRYING OUT THE INVENTION

Although any liquid crystalline compounds of the present invention expressed by the general formula (1) exhibit an excellent miscibility with existing liquid crystalline compounds even at low temperatures while having a high voltage holding ratio and a high ($\Delta\in$), these characteristics are influenced by —(O)$_{n2}$—Y which is an electron withdrawing group at the right hand side terminal (hereinafter sometimes referred to as first electron withdrawing group) and F—(CH$_2$)$_{n0}$— which is an electron withdrawing group at the left hand side terminal (hereinafter sometimes referred to as second electron withdrawing group). As the first electron withdrawing group, groups expressed by the formula in which n2 is 0 or 1, and Y is a fluoroalkyl group having 2 to 7 carbon atoms are suitable, and as the second electron withdrawing group, alkyl chains which are expressed by the formula in which n0 is an integer of 2 to 10 (based on the balance between temperature range of liquid crystal phase and viscosity) and have one fluorine atom at a terminal are broadly suitable, respectively.

As preferable examples of the first electron withdrawing groups, —OCF$_2$CF$_2$H, —OCF$_2$CF$_3$, —OCF$_2$CFHCF$_3$, —OCH$_2$CF$_2$H, —OCH$_2$CF$_3$, —CF$_2$CF$_2$H, —CF$_2$CF$_3$, —CHFCF$_3$, —OCHFCF$_3$, or —CHFCF$_2$H can be mentioned. Among which, as the groups which increase $\Delta\in$ of the compounds, —CF$_2$CF$_2$H or —CF$_2$CF$_3$; as the groups which improve the miscibility at low temperatures, —OCF$_2$CF$_2$H, —OCF$_2$CFHCF$_3$, or —OCH$_2$CF$_2$H can be mentioned, respectively.

As preferable examples of the second electron withdrawing groups, particularly as the groups which bring about excellent balance between the temperature range of liquid crystal phase and viscosity, groups expressed by the formula F—(CH$_2$)$_{n0}$— in which n0 is an integer of 2 to 7 can be mentioned.

As described above, ring A1 and ring A2 are each independently selected from the groups of the formulas (a)

to (i), and n1, $Q_1$, and $Q_2$ are as described above. While the compounds of the present invention are provided under such conditions, the compounds expressed by one of the formulas (1-A) to (1-E) can be mentioned as preferable examples of the compounds.

Further, in addition to the compounds described above, compounds which have the same structure as those expressed by one of the formulas (1-A) to (1-E) described above with the exception that at least one of the ring A1 and ring A2 in the general formula (1) is changed to the silacyclohexane ring selected from the rings of the formula (h) and (i) described above can be mentioned as preferable examples. That is because lowering of clearing point and improvement of miscibility at low temperatures can be obtained by these compounds.

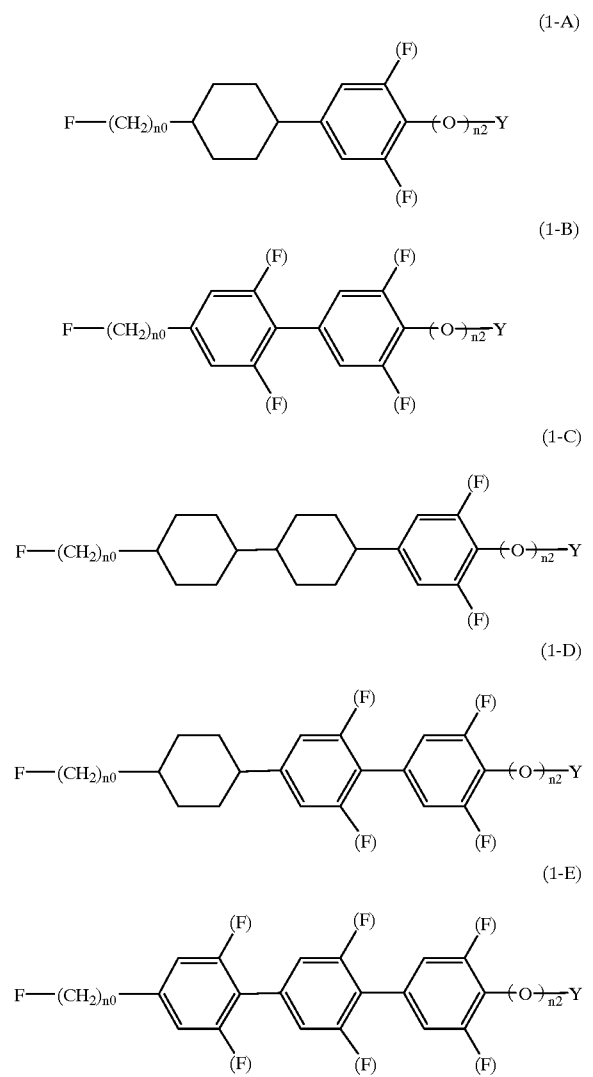

While any of the preferable compounds expressed by one of the formulas (1-A) to (1-E) described above exhibit a sufficiently high voltage holding ratio, the compounds have further excellent characteristics as follows:

First, two-ringed compounds expressed by the formula (1-A) or (1-B) are useful when used as component of liquid crystal compositions of which a low viscosity is required, since any of the compounds are remarkably excellent in the miscibility at low temperatures and are low in viscosity.

Among them, particularly the compounds expressed by the formula (1-B) in which both of two rings are substituted or unsubstituted phenyl groups exhibit a still higher Δn.

Among the three-ringed compounds expressed by one of the formulas (1-C) to (1-E), compounds expressed by the formula (1-C) are high in clearing point, have a low viscosity, and are remarkably excellent in miscibility at low temperatures.

Compounds expressed by the formula (1-E) exhibit a high Δn. As to the miscibility at low temperatures, however, the compounds of the formula (1-E) are outstandingly excellent for compounds having such a terphenyl skeleton, but inferior to the compounds expressed by the formula (1-C) described above. Compounds expressed by the formula (1-D) are placed at about the middle position between compounds of the formula (1-C) and compounds of the formula (1-E) in properties represented by Δn, clearing point, viscosity, and miscibility at low temperatures.

Further, in any type of compounds expressed by one of the formulas (1-A) to (1-E) described above, the larger number of fluorine atoms substituted at lateral positions in benzene ring the compounds have, the higher Δ∈ and the higher viscosity the compounds exhibit.

In the liquid crystalline compounds of the present invention expressed by the general formula (1), each element in the formula may be selected from its isotope. This is because characteristics of liquid crystals are not appreciably changed when the compounds contain such an isotope compared with the case in which the isotope is not contained, and similar effects can be expected.

While the compounds of the present invention are suitable as component of liquid crystal compositions particularly for TFT, they are also useful in other applications, for example, as component of liquid crystal compositions for TN, Guest-host mode, polymer dispersion type liquid crystal display devices, dynamic scattering mode, STN, in-plane switching, OCB mode, or R—OCB mode, and further, they are suitable as compound for ferroelectric liquid crystals and antiferroelectric liquid crystals.

Liquid crystal compositions provided according to the present invention comprise, as a first component, at least one liquid crystalline compound expressed by the general formula (1).

Its content is necessary to be 0.1 to 99.9% by weight based on the weight of liquid crystal composition in order to develop excellent characteristics, and the content is preferably 1 to 50% by weight and more desirably 3 to 20% by weight.

While the liquid crystal compositions of the present invention may be composed only of the first component described above, compositions are preferable in which at least one compound selected from the compounds expressed by one of the general formulas (2), (3), and (4) (hereinafter referred to as second component A) and at least one compound selected from the compounds expressed by the general formula (5) and (6) (hereinafter referred to as second component B) are mixed as a second component, or at least one compound selected from the compounds expressed by one of the general formulas (7), (8), and (9) is further mixed as a third component, in addition to the first component. Still further, an optically active compound, and a known compound for the purpose of adjusting threshold voltage, temperature range of liquid crystal phase, Δ∈, Δn, and viscosity can suitably be mixed as other components.

Among the second component A described above, as preferable examples of the compounds included in the general formula (2), the compounds of the following formulas (2-1) to (2-9); as preferable examples of the compounds included in the general formula (3), the compounds of the following (3-1) to (3-69); and as preferable examples of the compounds included in the general formula (4), the compounds of the following formulas (4-1) to (4-24) can be mentioned, respectively.
(2-1)
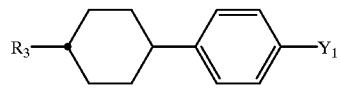
(2-2)
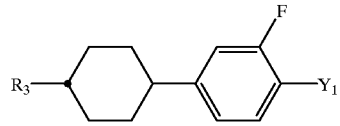
(2-3)
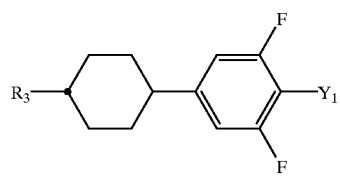
(2-4)
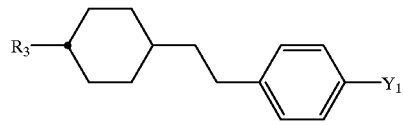
(2-5)
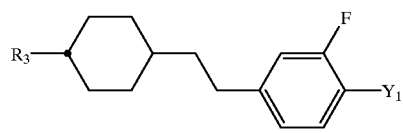
(2-6)
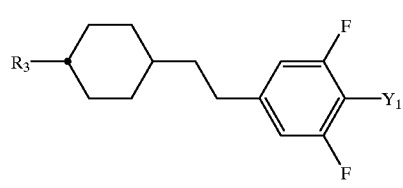
(2-7)
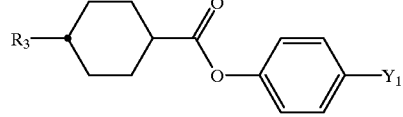
(2-8)
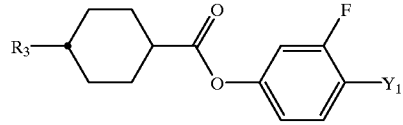
(2-9)
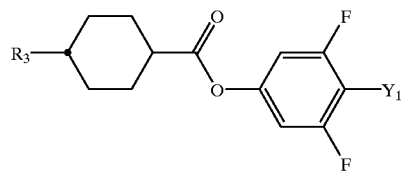
(3-1)
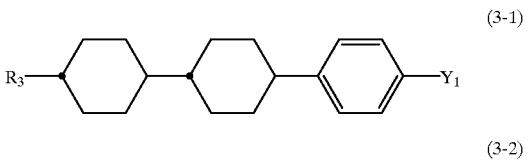
(3-2)
(3-3)
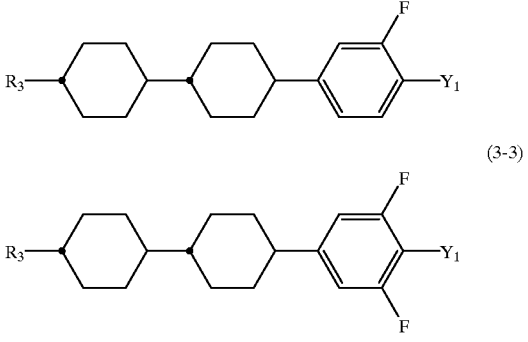
(3-4)
(3-5)
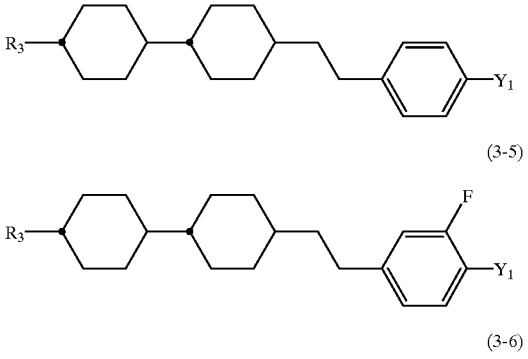
(3-6)
(3-7)
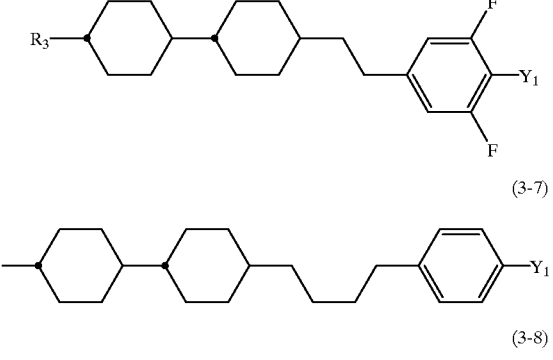
(3-8)
(3-9)
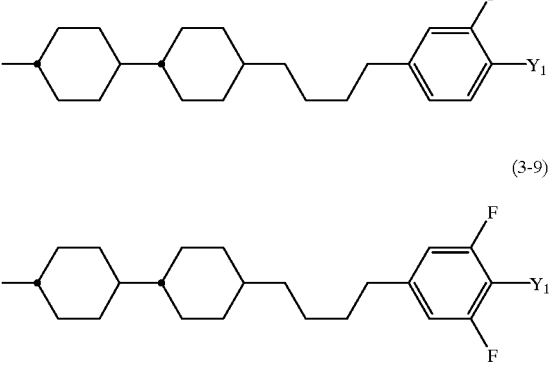

(3-10)
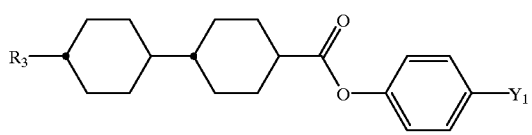
(3-11)
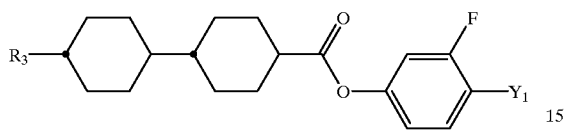
(3-12)
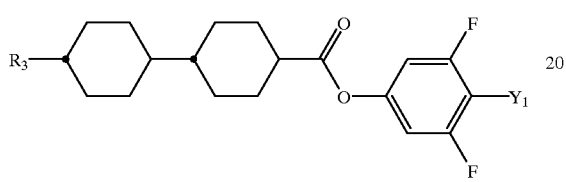
(3-13)
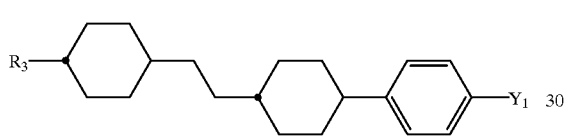
(3-14)
(3-15)
(3-16)
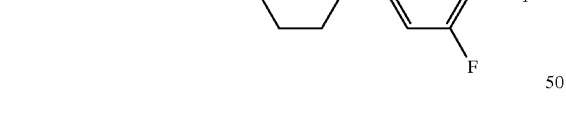
(3-17)
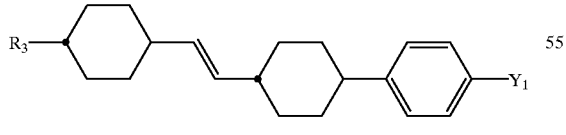
(3-18)
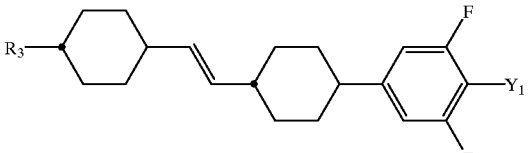
(3-19)
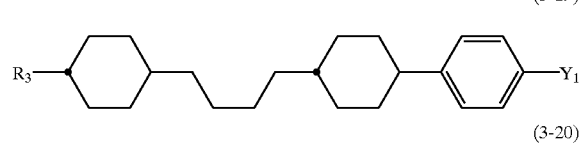
(3-20)
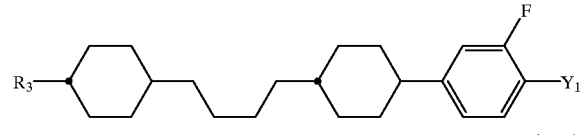
(3-21)
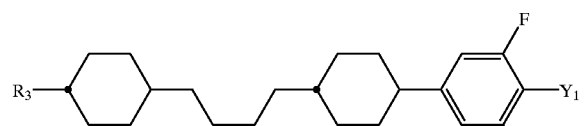
(3-22)
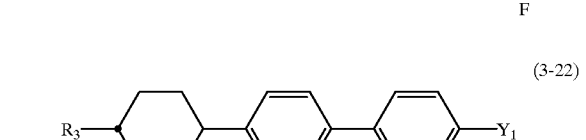
(3-23)
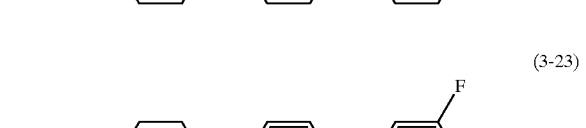
(3-24)
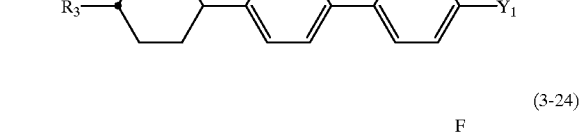
(3-25)
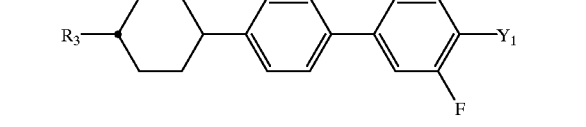
(3-26)
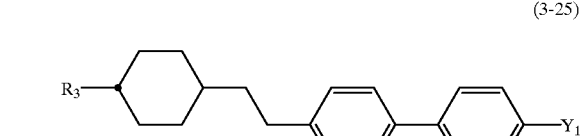

(3-27)
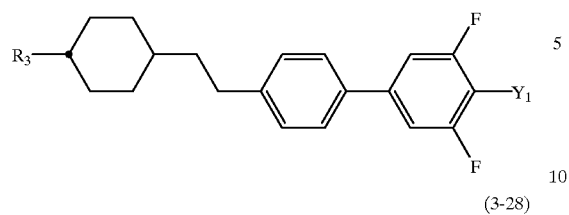
(3-28)
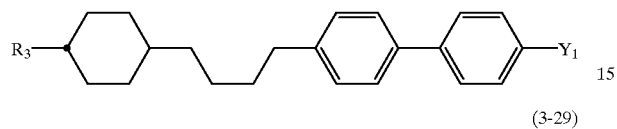
(3-29)
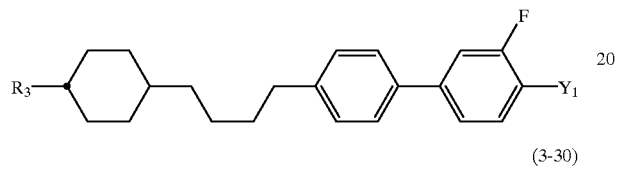
(3-30)
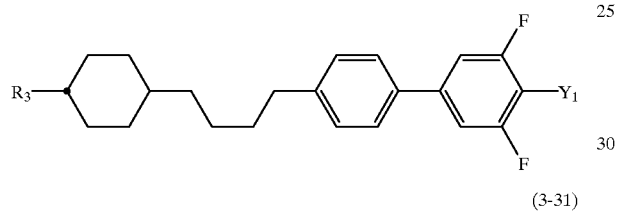
(3-31)
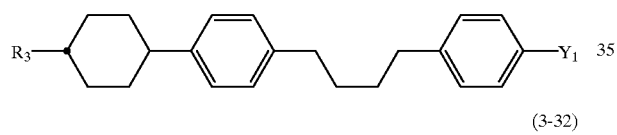
(3-32)
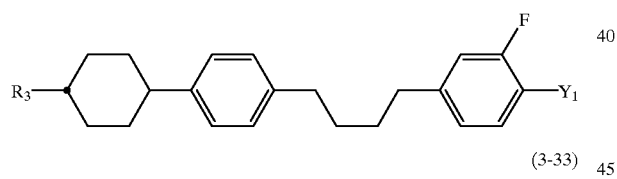
(3-33)
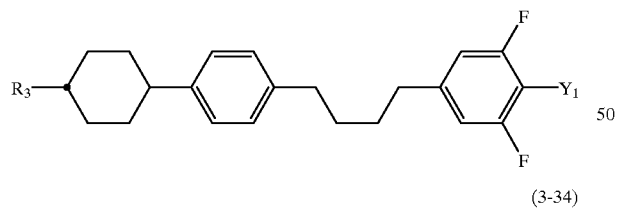
(3-34)
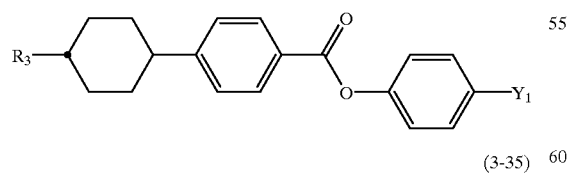
(3-35)
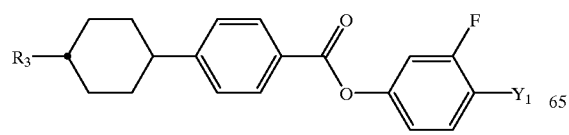
(3-36)
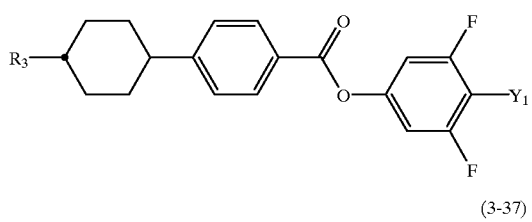
(3-37)
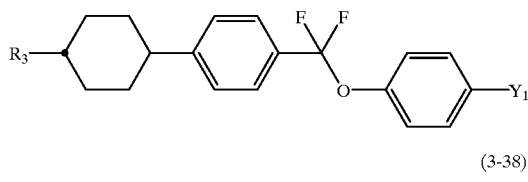
(3-38)
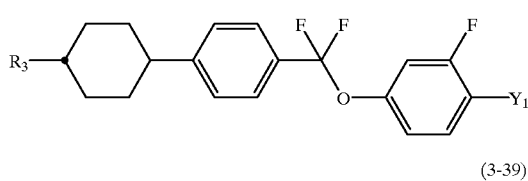
(3-39)
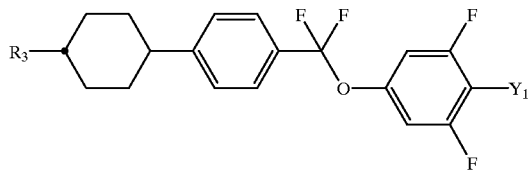
(3-40)
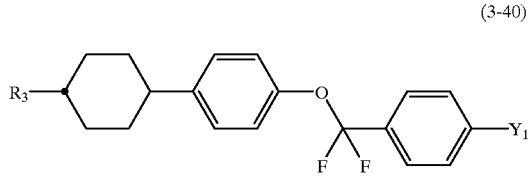
(3-41)
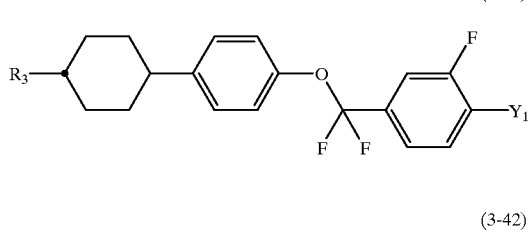
(3-42)
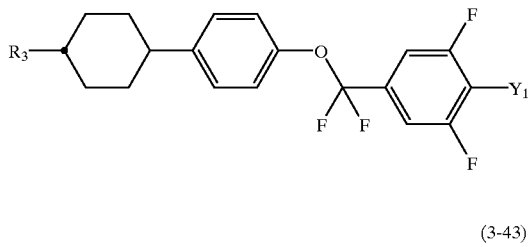
(3-43)
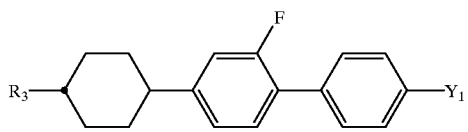

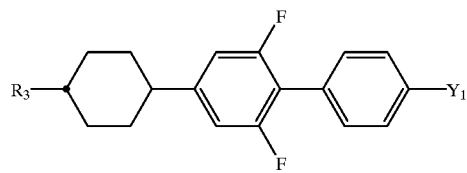
(3-44)
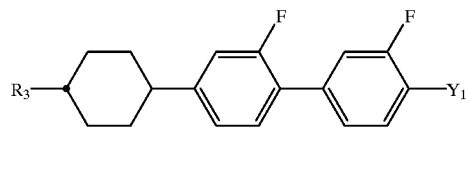
(3-45)
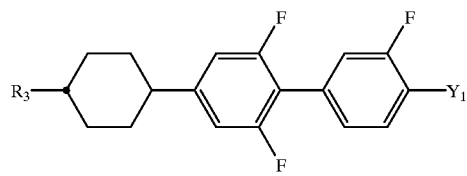
(3-46)
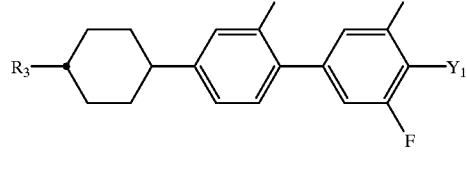
(3-47)
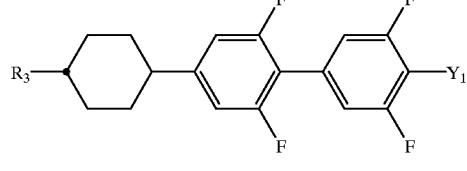
(3-48)
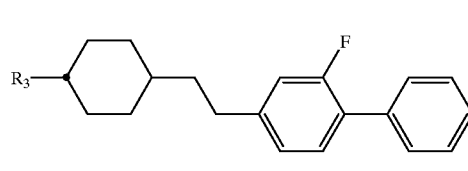
(3-49)
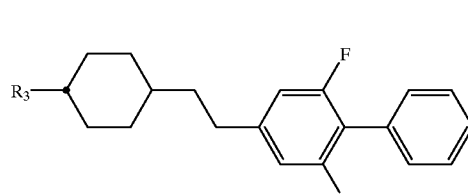
(3-50)
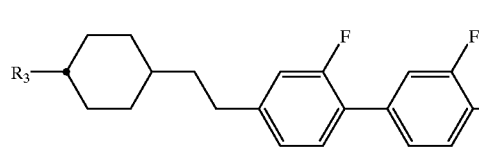
(3-51)
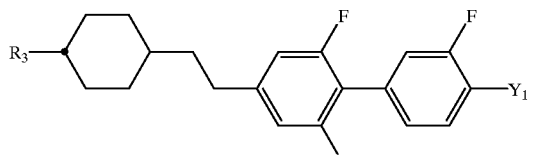
(3-52)
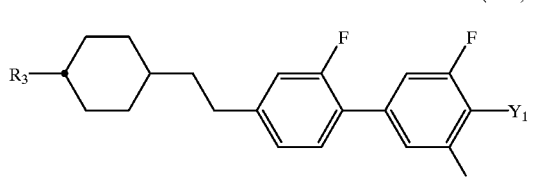
(3-53)
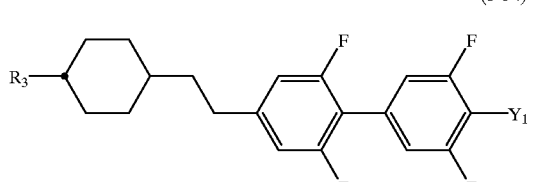
(3-54)
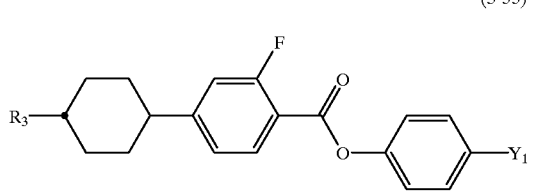
(3-55)
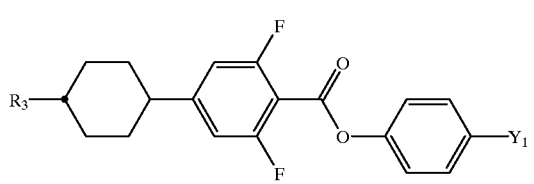
(3-56)
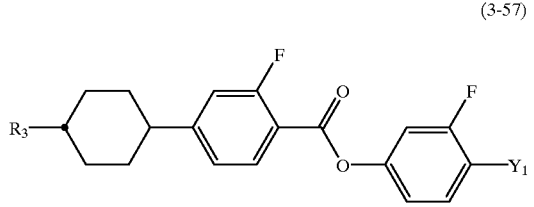
(3-57)
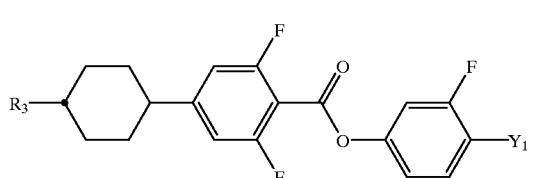
(3-58)

(3-59)
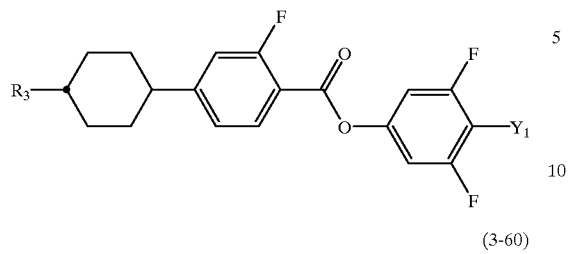
(3-60)
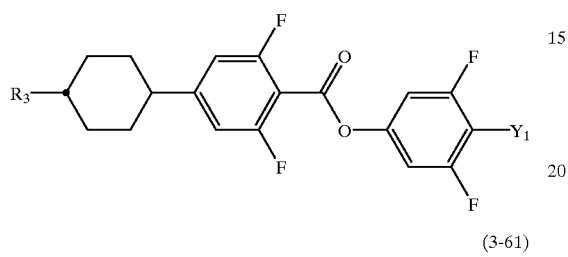
(3-61)
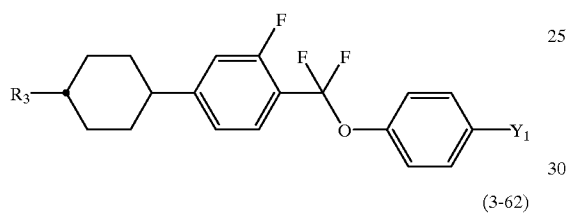
(3-62)
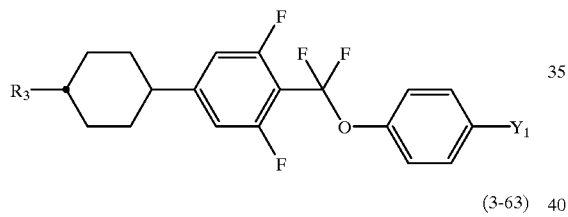
(3-63)
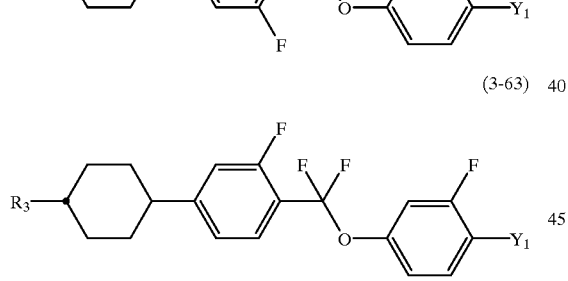
(3-64)
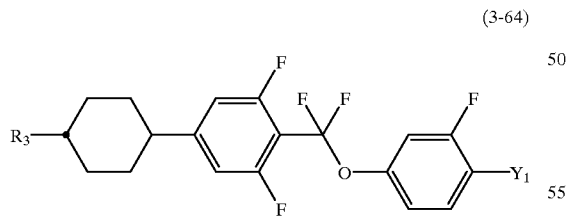
(3-65)
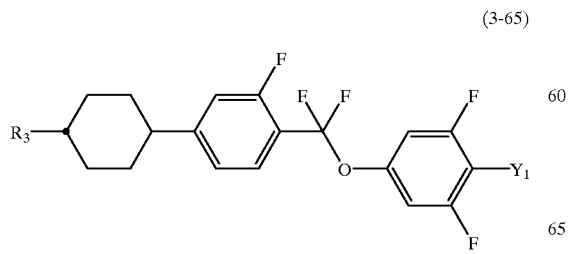
(3-66)
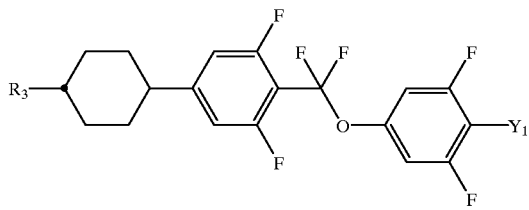
(3-67)
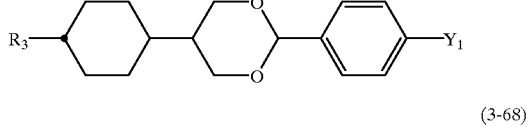
(3-68)
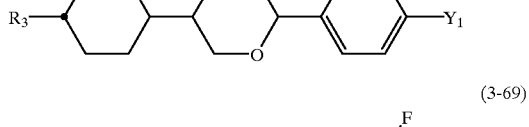
(3-69)
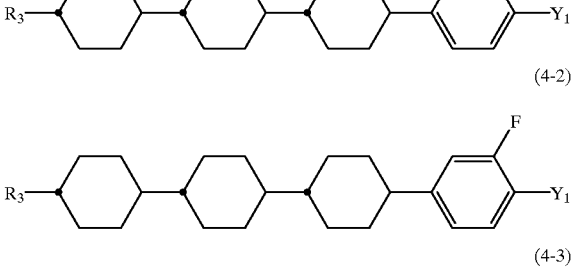
(4-1)
(4-2)
(4-3)
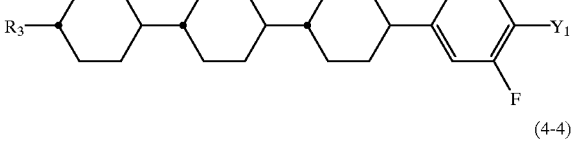
(4-4)
(4-5)
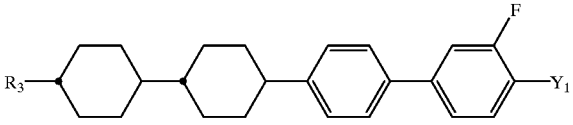

(4-6) 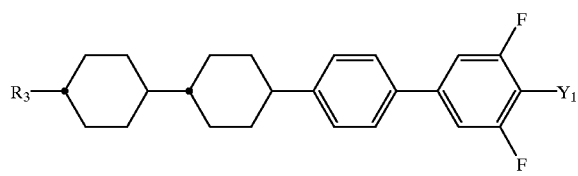
(4-7) 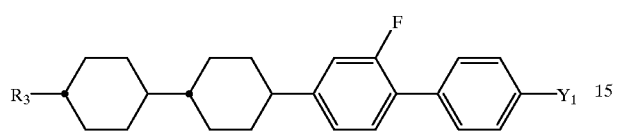
(4-8) 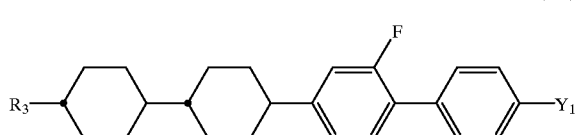
(4-9) 
(4-10) 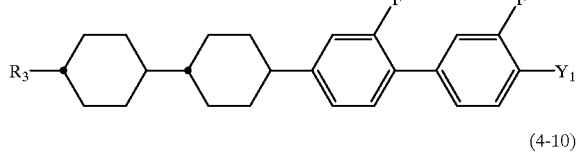
(4-11) 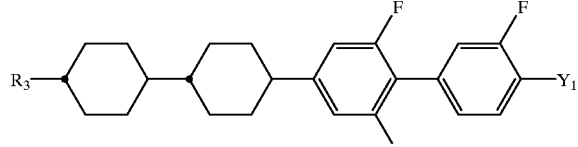
(4-12) 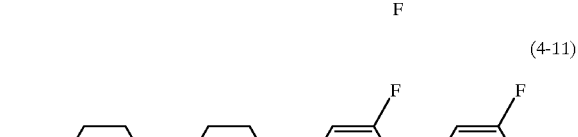
(4-13) 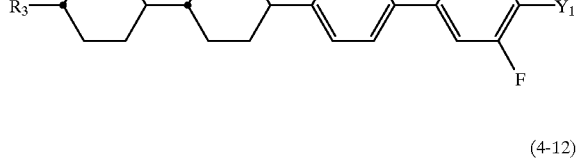
(4-14) 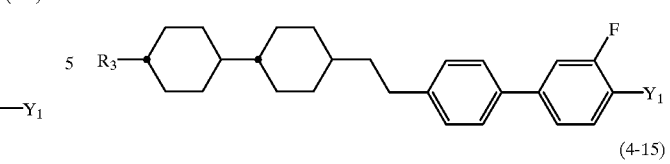
(4-15) 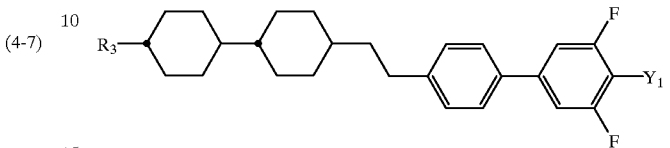
(4-16) 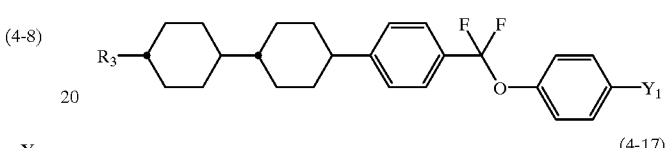
(4-17) 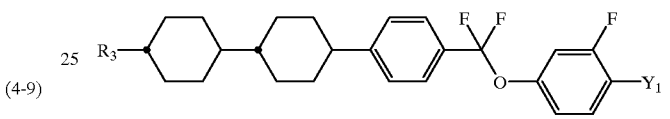
(4-18) 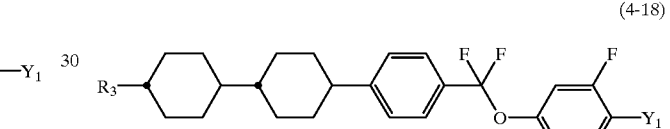
(4-19) 
(4-20) 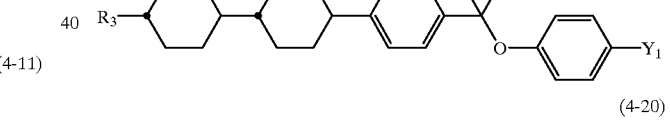
(4-21) 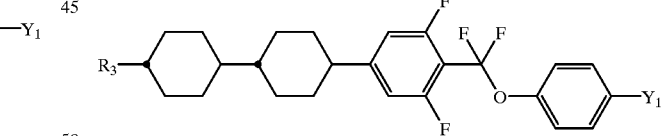
(4-22) 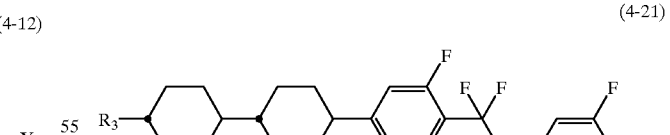

(4-23)

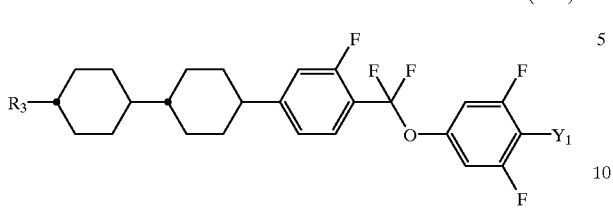

(4-24)

wherein $R_3$ and $Y_1$ have the same meaning as described above, and each atom which constitutes the compounds of each formula may be its isotope.

Compounds expressed by one of these general formulas (2) to (4) exhibit a positive $\Delta\varepsilon$, are excellent in thermal stability and chemical stability, and are indispensable when liquid crystal compositions for TFT of which a high reliability such as a high voltage holding ratio (a large specific resistivity) is required are produced.

While the amount of the compound to be used is suitably in the range of 1 to 99% by weight when liquid crystal compositions for TFT are produced, the amount is preferably 10 to 97% by weight and more desirably 40 to 95% by weight. At that time, compounds expressed by one of the general formulas (7) to (9) may be comprised.

Compounds expressed by one of the general formulas (2) to (4) described above can also be used when liquid crystal compositions for STN display mode or TN display mode are produced.

Next, among the second component B described above, as preferable examples of the compounds included in the general formula (5), the compounds expressed by one of the following formulas (5-1) to (5-40); and as preferable examples of the compounds included in the general formulas (6), the compounds expressed by one of the following formulas (6-1) to (6-3) can be mentioned.

(5-1)

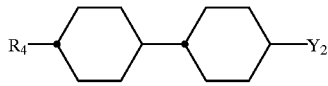

(5-2)

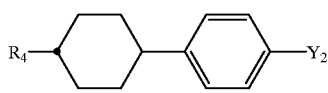

(5-3)

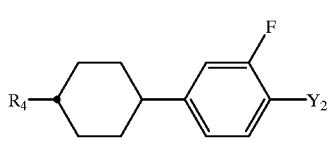

(5-4)

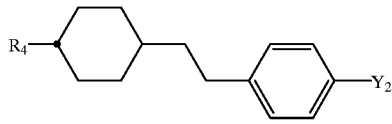

(5-5)

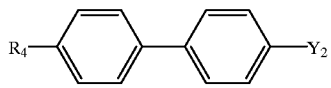

(5-6)

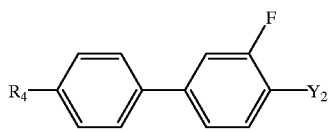

(5-7)

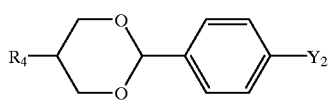

(5-8)

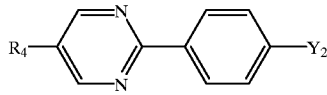

(5-9)

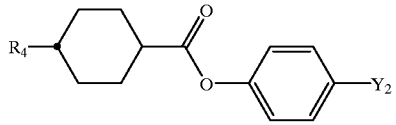

(5-10)

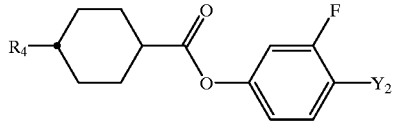

(5-11)

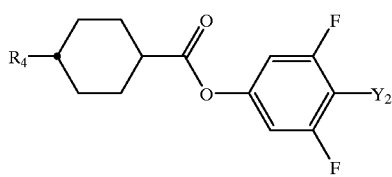

(5-12)

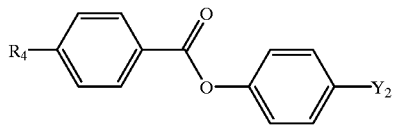

(5-13)

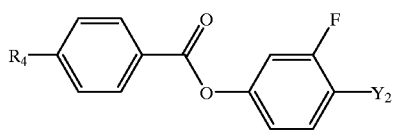

(5-14) 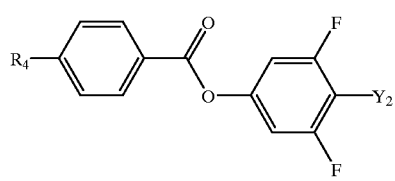
(5-15) 
(5-16) 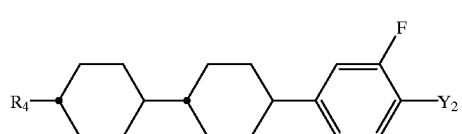
(5-17) 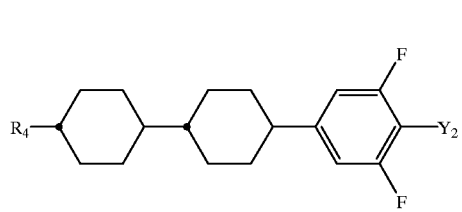
(5-18) 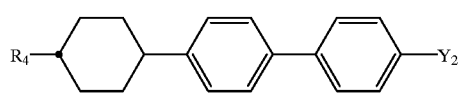
(5-19) 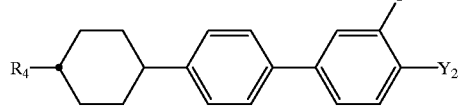
(5-20) 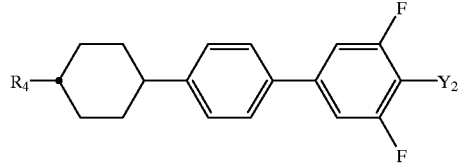
(5-21) 
(5-22) 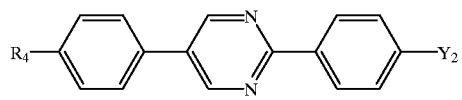
(5-23) 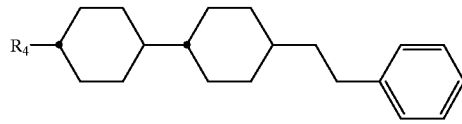
(5-24) 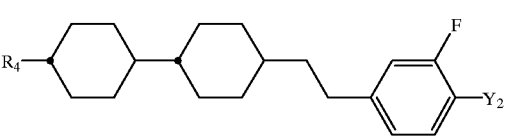
(5-25) 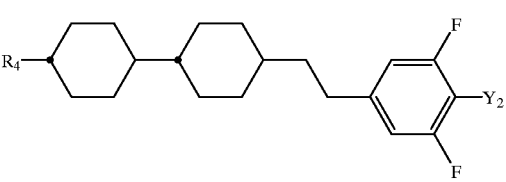
(5-26) 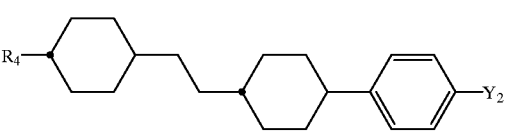
(5-27) 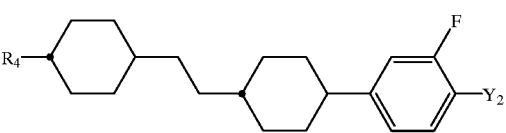
(5-28) 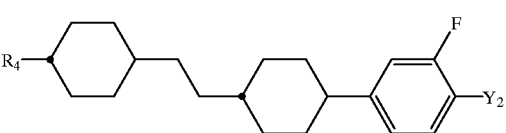
(5-29) 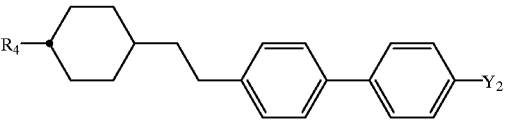
(5-30) 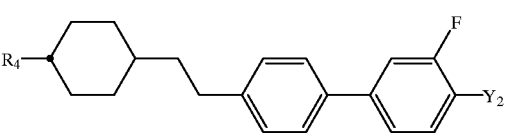
(5-31) 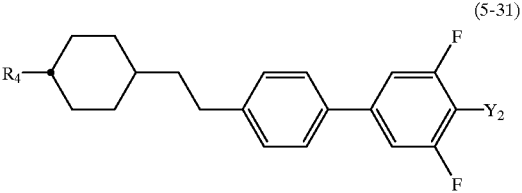

(5-32)
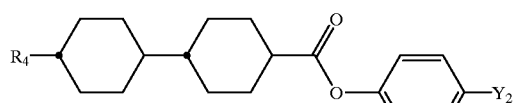

(5-33)
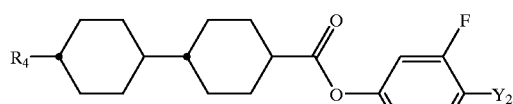

(5-34)
(5-35)
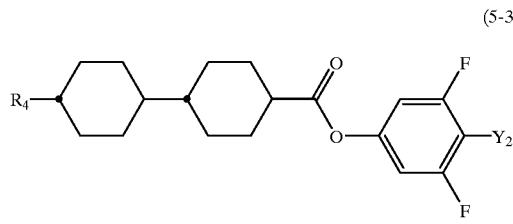

(5-36)
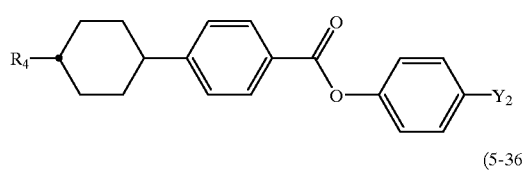

(5-37)
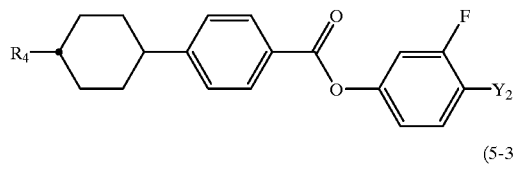

(5-38)
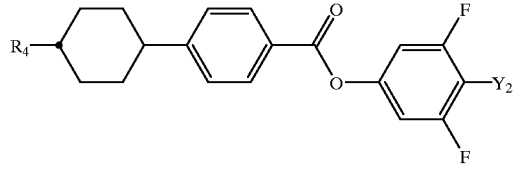

(5-39)
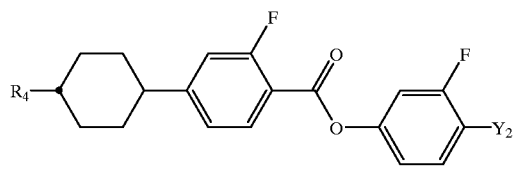

(5-40)
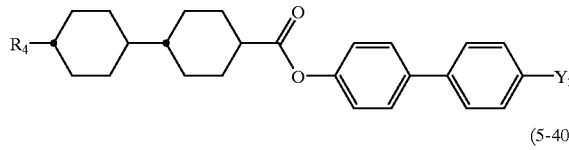

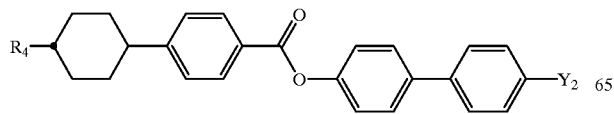

(6-1)
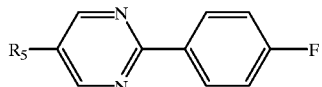

(6-2)
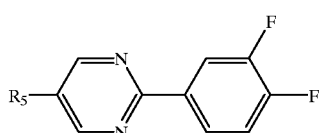

(6-3)
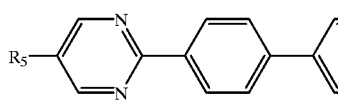

wherein $R_4$, $R_5$, and $Y_2$ have the same meaning as described above, and each atom which constitutes the compounds of each formula may be its isotope.

Compounds expressed by the general formula (5) and (6) have a positive and particularly large value of $\Delta\epsilon$, and are used for the purpose of lowering threshold voltage of liquid crystal compositions. Also, they are used for the purpose of improving steepness of the threshold voltage of liquid crystal compositions for STN display mode or TN display mode including for the purpose of adjusting $\Delta n$ and widening nematic range of liquid crystal compositions such as raising clearing point, and thus are indispensable compounds when liquid crystal compositions particularly for STN display mode and TN display mode are produced.

As the amount of the compounds to be used is increased, threshold voltage of liquid crystal compositions can be lowered, but, on the other hand, viscosity of the compositions rises. Accordingly, it is advantageous for driving devices that the amount of the compounds used is as large as possible so far as the viscosity of the liquid crystal compositions satisfies required characteristics.

Due to such circumstances, when liquid crystal compositions for STN display mode or TN display mode are produced, the amount of the compounds used is suitably in the range of 0.1 to 99.9% by weight, preferably 10 to 97% by weight, and more desirably 40 to 95% by weight based on the total amount of liquid crystal composition.

Among the third component described above, as preferable examples of the compounds included in the general formula (7), the compounds of the following formulas (7-1) to (7-11); as preferable examples of the compounds included in the general formula (8), the compounds of the following formulas (8-1) to (8-18); and as preferable examples of the compounds included in the general formula (9), the compounds of the following formulas (9-1) to (9-6) can be mentioned, respectively.

(7-1)
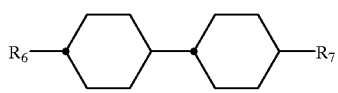

(7-2)
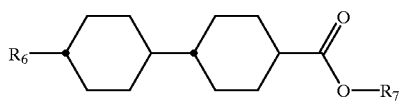

-continued
(7-3) 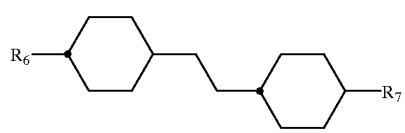
(7-4) 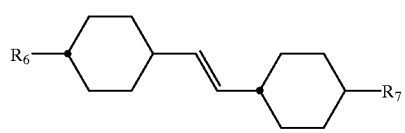
(7-5) 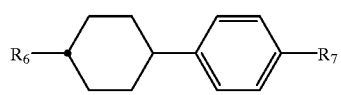
(7-6) 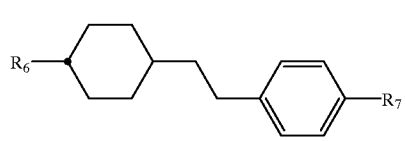
(7-7) 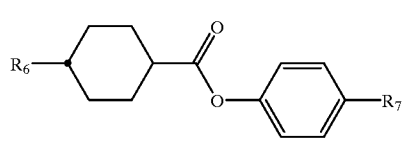
(7-8) 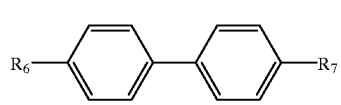
(7-9) 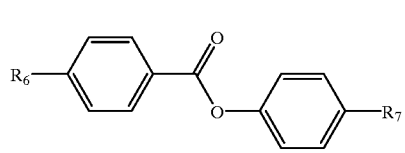
(7-10) 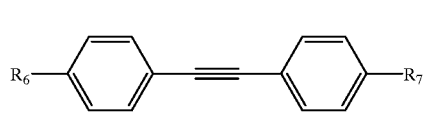
(7-11) 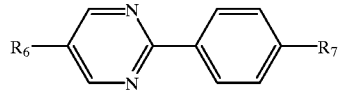
(8-1) 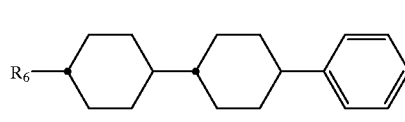
(8-2) 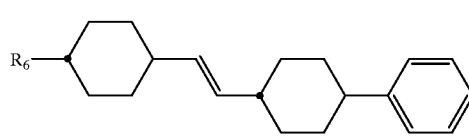
-continued
(8-3) 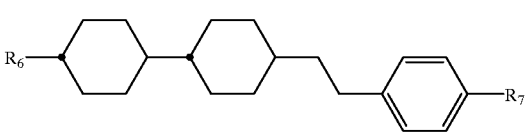
(8-4) 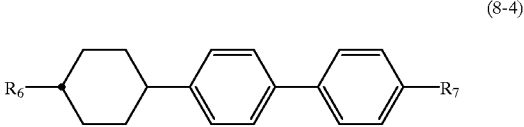
(8-5) 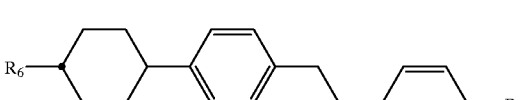
(8-6) 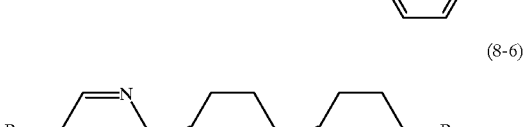
(8-7) 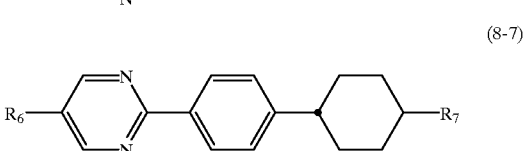
(8-8) 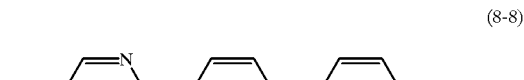
(8-9) 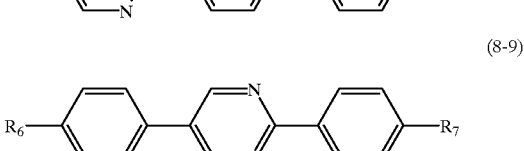
(8-10) 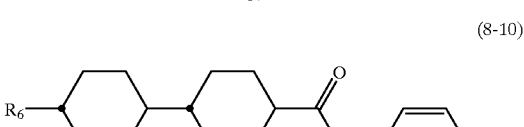
(8-11) 
(8-12) 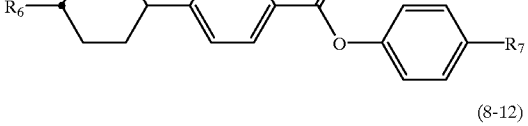

(8-13)
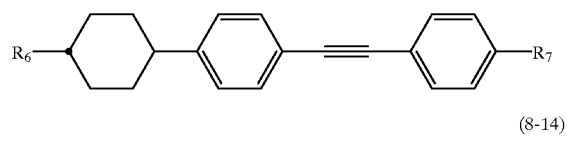

(8-14)
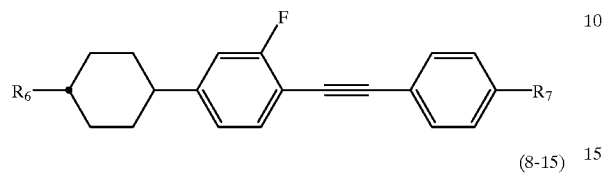

(8-15)
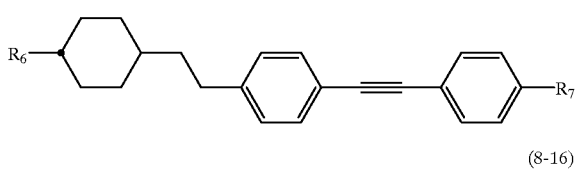

(8-16)
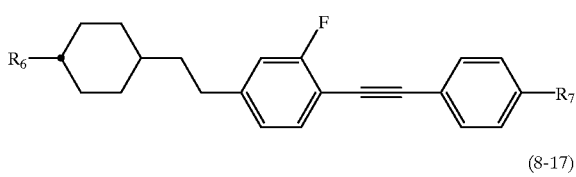

(8-17)
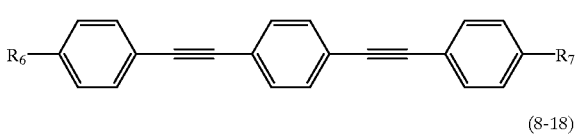

(8-18)
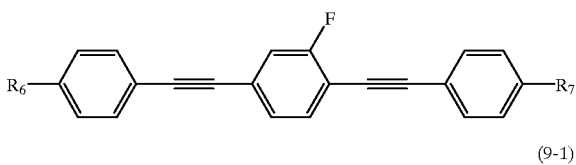

(9-1)
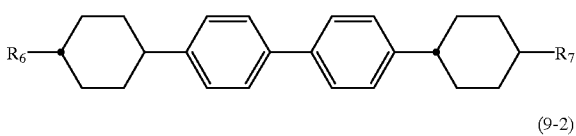

(9-2)
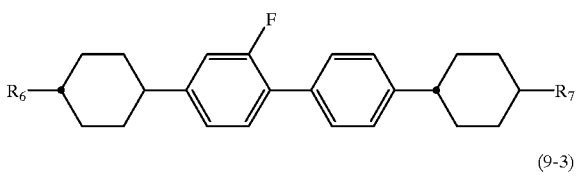

(9-3)
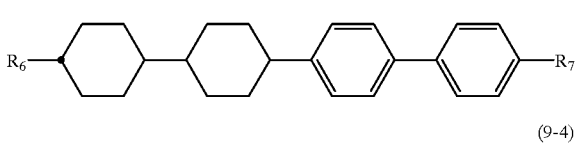

(9-4)

(9-5)
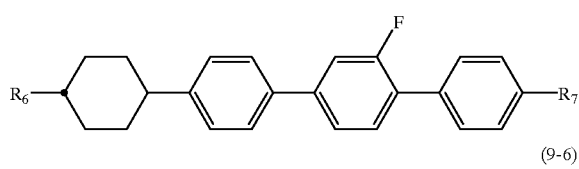

(9-6)
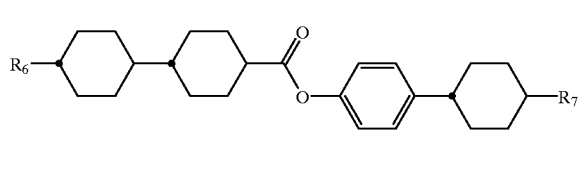

wherein $R_6$ and $R_7$ have the same meaning as described above, and each atom which constitutes the compounds of each formula may be its isotope.

Compounds expressed by one of these general formulas (7) to (9) have a small absolute value or close to 0 of $\Delta\varepsilon$. Among them, compounds of the general formula (7) are used principally for the purpose of adjusting viscosity or adjusting $\Delta n$ of liquid crystal compositions, and compounds of the general formula (8) or (9) are used for the purpose of widening nematic range of liquid crystal compositions such as raising clearing point and for the purpose of adjusting $\Delta n$.

As the amount of the compounds to be used is increased, threshold voltage of liquid crystal compositions rises, but, on the other hand, viscosity of the compositions lowers. Accordingly, the amount of the compound used is preferably as large as possible so far as the threshold voltage of liquid crystal compositions satisfies required characteristics.

Due to such circumstances, when liquid crystal compositions for TFT are produced, the amount of the compounds used is suitably 40% by weight or less, and preferably 35% by weight or less based on the total amount of liquid crystal composition. On the other hand, when liquid crystal compositions for STN display mode or TN display mode are produced, the amount of the compounds used is suitably 70% by weight or less, and preferably 60% by weight or less based on the total amount of liquid crystal composition.

Next, with the exception of such specific cases, for example, as liquid crystal compositions for OCB (Optically Compensated Birefringence) mode, an optically active compound among other components is added to the liquid crystal compositions of the present invention generally for the purpose of inducing helical structure of liquid crystal composition to adjust required twist angle and to prevent reverse twist.

While the optically active compound is broadly selected from known compounds so far as such purposes as described above can be achieved, optically active compounds expressed by one of the following formulas (Op-1) to (Op-8) can preferably be mentioned as preferable ones.

(Op-1)
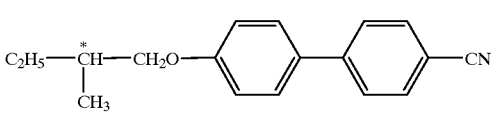

-continued (Op-2)
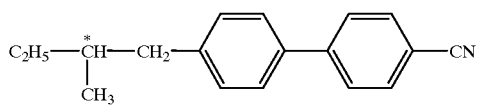

(Op-3)
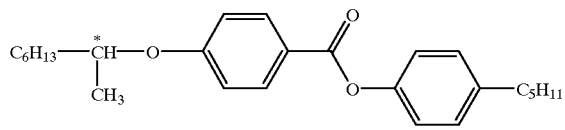

(Op-4)
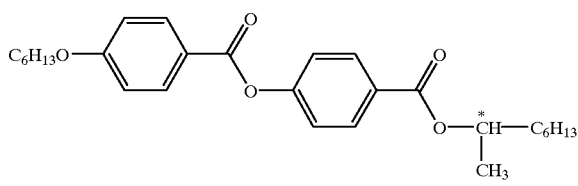

(Op-5)
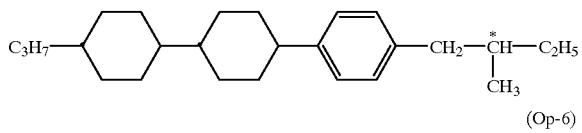

(Op-6)
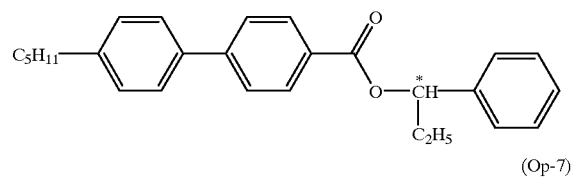

(Op-7)
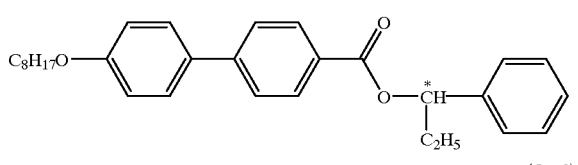

(Op-8)
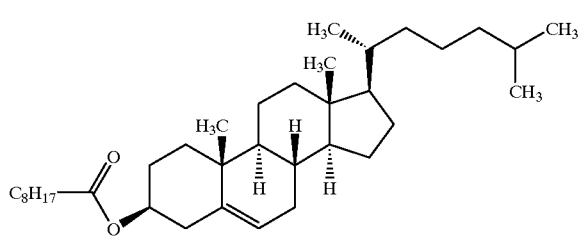

Pitch length of the twist of liquid crystal compositions are adjusted by adding these optically active compounds. The pitch length is preferably adjusted in the range of 40 to 200 μm in the case of liquid crystal compositions for TFT or TN, preferably adjusted in the range of 6 to 20 μm in the case of liquid crystal compositions for STN, and preferably adjusted in the range of 1.5 to 4 μm in the case for bistable TN mode, respectively.

Further, two or more kind of optically active compounds may be added for the purpose of adjusting the dependency of the pitch length on temperature.

Liquid crystal compositions provided according to the present invention can be produced by methods which are conventional by themselves. Generally, they are produced by a method in which various components are dissolved in one another at a high temperature.

Further, the liquid crystal compositions of the present invention can be used as ones for guest-host (GH) mode by adding a dichroic dye such as merocyanine type, styryl type, azo type, azomethine type, azoxy type, quinophthalone type, anthraquinone type, and tetrazine type thereto at the time of production. Alternatively, the liquid crystal compositions can be used as NCAP which is prepared by the microencapsulation of a nematic liquid crystal, or as liquid crystal compositions for polymer dispersed liquid crystal display devices (PDLCD) represented by polymer net work liquid crystal display devices (PNLCD) prepared by forming a polymer of three-dimensional reticulated structure in a liquid crystal. Still further, the liquid crystal compositions of the present invention can be used as ones for electrically controlled birefringence (ECB) mode or dynamic scattering (DS) mode.

While the nematic liquid crystal compositions of the present invention are produced by such methods, the following Composition Examples 1 to 26 can be mentioned as their examples:

In each of the following composition examples, compounds are designated by indicating the left hand side terminal group, bonding group, ring structure, and right hand side terminal group in the compounds with corresponding symbols shown in columns for the groups and structure according to the definition shown in Table 1 below.

When hydrogen atoms on trans-1,4-cyclohexylene or trans, trans-bicyclohexane-4,4'-diyl group are replaced by their isotopes, heavy hydrogen atoms (deuteriums), and each of the groups mentioned above are expressed by the formula (70) and (71), respectively, the heavy hydrogen atoms are indicated with symbols H[1D, ~8D] and biH[1D,~8D] assuming that hydrogen atom on the ring $J^1$, $J^2$, $J^3$, $J^4$, $J^5$, $J^6$, $J^7$, or $J^8$ is replaced by only heavy hydrogen atom selected from corresponding heavy hydrogen atoms 1D, 2D, 3D, 4D, 5D, 6D, 7D, and 8D in turn.

Compound No. appended to the compounds of the present invention in the following Composition Examples means that the compounds are the same as those shown in Examples described below and having the same appended Compound No.; and the content of compounds means % by weight unless otherwise specified.

Further, data of characteristics of compositions in Composition Examples are indicated by TNI (transition temperature of nematic phase-isotropic liquid, or clearing point), η (viscosity: determined at 20.0° C.), Δn (optical anisotropy value: determined at 25.0° C.), Δ∈ (dielectric anisotropy value: determined at 25.0° C.), Vth (threshold voltage: determined at 25.0° C.), and P (pitch: determined at 25.0° C.).

(71)
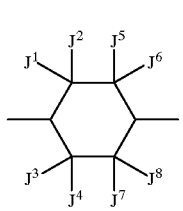

(72)

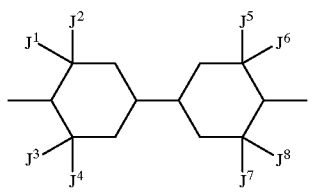

TABLE 1

Method for designating compounds by using symbols
R—(A₁)—Z₁—...—Zₙ—(Aₙ)—X

| 1) Left side terminal group R— | Symbol |
|---|---|
| $C_nH_{2n+1}$— | n- |
| $C_nH_{2n+1}O$— | nO— |
| $C_nH_{2n+1}OC_mH_{2m}$— | nOm- |
| $CH_2=CH$— | V— |
| $CH_2=CHC_nH_{2n}$— | Vn- |
| $C_nH_{2n+1}CH=CHC_mH_{2m}$— | nVm- |
| $C_nH_{2n+1}CH=CHC_mH_{2m}CH=CHC_kH_{2k}$— | nVmVk- |
| $FC_nH_{2n}$— | Fn- |

| 2) Ring structure —(A1)—, —(An)— | Symbol |
|---|---|
| (benzene ring) | B |
| (benzene ring with F) | B(F) |
| (benzene ring with 2F,3F) | B(2F,3F) |
| (benzene ring with F,F) | B(F,F) |
| (benzene ring with F,CL) | B(F,CL) |
| (cyclohexane) | H |

TABLE 1-continued

Method for designating compounds by using symbols
R—(A₁)—Z₁—...—Zₙ—(Aₙ)—X

| | Symbol |
|---|---|
| (pyrimidine ring) | Py |
| (dioxane ring) | G |
| (cyclohexene ring) | Ch |

| 3) Bonding group —Z₁—, —Zₙ— | Symbol |
|---|---|
| —$C_2H_4$— | 2 |
| —$C_4H_8$— | 4 |
| —COO— | E |
| —C≡C— | T |
| —CH=CH— | V |
| —$CF_2O$— | CF2O |
| —$OCF_2$— | OCF2 |

| 4) Right side terminal group —X | Symbol |
|---|---|
| —F | —F |
| —Cl | —CL |
| —CN | —C |
| —$CF_3$ | —CF3 |
| —$CF_2CF_2H$ | —CF2CF2H |
| —$OCF_3$ | —OCF3 |
| —$OCH_2CF_3$ | —OlCF3 |
| —$OCF_2H$ | —OCF2H |
| —$OCH_2CF_2H$ | —OlCF2H |
| —$OCF_2CF_2H$ | —OCF2CF2H |
| —$OCF_2CFHCF_3$ | —OCF2CFHCF3 |
| —$C_nH_{2n+1}$ | -n |
| —$OC_nH_{2n+1}$ | —On |
| —$COOCH_3$ | —EMe |
| —$C_nH_{2n}CH=CH_2$ | -nV |
| —$C_mH_{2m}CH=CHC_nH_{2n+1}$ | -mVn |
| —$C_mH_{2m}CH=CHC_nH_{2n}F$ | -mVnF |
| —CH=$CF_2$ | —VFF |
| —$C_nH_{2n}CH=CF_2$ | -nVFF |

5) Examples of designation

Example 1 3-H2B(F,F)B(F)-F $C_3H_7$—(cyclohexane)—$C_2H_4$—(benzene with 2F)—(benzene with F)—F Example 2 3-HB(F)TB-2

$C_3H_7$—(cyclohexane)—(benzene with F)—C≡C—(benzene)—$C_2H_5$

TABLE 1-continued

Method for designating compounds by using symbols
R–(A₁)—Z₁— ... —Zₙ—(Aₙ)—X

Example 3  1V2-BEB(F,F)-C

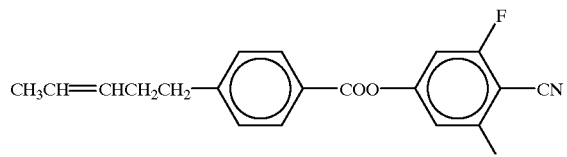

COMPOSITION EXAMPLE 1

Liquid crystal composition comprising the following compounds in the content shown below was prepared.

| | | |
|---|---|---|
| F3-HB (F, F) B (F) -OCF2CF2H | (No. 92) | 10.0% |
| 1 V2-BEB (F, F) -C | | 5.0% |
| 3-HB-C | | 15.0% |
| 1-BTB-3 | | 5.0% |
| 2-BTB-1 | | 10.0% |
| 3-HH-4 | | 11.0% |
| 3-HHB-1 | | 11.0% |
| 3-HHB-3 | | 9.0% |
| 3-H2BTB-2 | | 4.0% |
| 3-H2BTB-3 | | 4.0% |
| 3-H2BTB-4 | | 4.0% |
| 3-HB (F) TB-2 | | 6.0% |
| 3-HB (F) TB-3 | | 6.0% |

Characteristics of this composition was determined to be as follows:

TNI=92.3° C.
η=18.8 mPa·s
Δn=0.162
Δ∈=6.6
Vth=2.56 V

Further, a secondary composition was obtained by mixing 0.8 part of the optically active compound expressed by the formula (Op-4) described above with 100 parts of the primary composition described above. Characteristic of the secondary composition was determined to be as follows:

P=12.3 μm

COMPOSITION EXAMPLE 2

Liquid crystal composition comprising the following compounds in the content shown below was prepared.

| | | |
|---|---|---|
| F6-HB-O1CF3 | (No. 14) | 5.0% |
| F7-B (F, F) B (F) -OCF2CF3 | (No. 35) | 5.0% |
| V2-HB-C | | 12.0% |
| 1 V2-HB-C | | 12.0% |
| 3-HB-C | | 5.0% |
| 3-H [1D, 2D, 3D] B-C | | 9.0% |
| 3-HB (F) -C | | 5.0% |
| 2-BTB-1 | | 2.0% |
| 3-HH-4 | | 8.0% |
| 3-HH-VFF | | 6.0% |
| 2-H [1D, 2D, 3D] HB-C | | 3.0% |
| 3-HHB-C | | 6.0% |

-continued

| | |
|---|---|
| 3-HB (F) TB-2 | 8.0% |
| 3-H2 BTB-2 | 5.0% |
| 3-H2 BTB-3 | 5.0%. |
| 3-H2 BTB-4 | 4.0% |

Characteristics of this composition was determined to be as follows:

TNI=77.5° C.
η=19.3 mPa·s
Δn=0.158
Δ∈=7.2
Vth=2.38 V

COMPOSITION EXAMPLE 3

Liquid crystal composition comprising the following compounds in the content shown below was prepared.

| | | |
|---|---|---|
| F4-HHB (F) -O1CF2H | (No. 72) | 5.0% |
| 3O1-BEB (F) -C | | 15.0% |
| 4O1-BEB (F) -C | | 13.0% |
| 5O1-BEB (F) -C | | 13.0% |
| 2-HHB (F) -C | | 15.0% |
| 3-HHB (F) -C | | 15.0% |
| 3-HB (F) TB-2 | | 4.0% |
| 3-HB (F) TB-3 | | 4.0% |
| 3-HB (F) TB-4 | | 4.0% |
| 3-HHB-1 | | 8.0% |
| 3-HHB-O1 | | 4.0% |

Characteristics of this composition was determined to be as follows:

TNI=95.9° C.
η=86.3 mPa·s
Δn=0.149
Δ∈=29.2
Vth=1.05 V

COMPOSITION EXAMPLE 4

Liquid crystal composition comprising the following compounds in the content shown below was prepared.

| | | |
|---|---|---|
| F5-B (F, F) B (F) B-OCF2CFHCF3 | (No. 129) | 4.0% |
| 5-PyB - F | | 4.0% |
| 3-PyB (F) -F | | 4.0% |
| 2-BB-C | | 5.0% |
| 5-BB-C | | 5.0% |
| 2-PyB-2 | | 2.0% |
| 3-PyB-2 | | 2.0% |
| 4-PyB-2 | | 2.0% |
| 6-PyB-O5 | | 3.0% |
| 6-PyB-O6 | | 3.0% |
| 6-PyB-O7 | | 3.0%. |
| 6-PyB-O8 | | 3.0% |
| 3-PyBB-F | | 6.0% |
| 4-PyBB-F | | 6.0% |
| 5-PyBB-F | | 6.0% |
| 3-HHB-1 | | 6.0% |
| 3-HHB-3 | | 8.0% |
| 2-H2BTB-2 | | 4.0% |
| 2-H2BTB-3 | | 4.0% |
| 2-H2BTE-4 | | 5.0% |
| 3-H2BTB-2 | | 5.0% |

-continued

| | |
|---|---|
| 3-H2BTB-3 | 5.0% |
| 3-H2BTB-4 | 5.0% |

Characteristics of this composition was determined to be as follows:

TNI=95.0° C.
$\eta$=35.6 mPa·s
$\Delta n$=0.200
$\Delta \epsilon$=5.8
Vth=2.47 V

COMPOSITION EXAMPLE 5

Liquid crystal composition comprising the following compounds in the content shown below was prepared.

| | | |
|---|---|---|
| F5-HB (F, CL) B (F, F) -CF2CF2H | (No. 110) | 2.0% |
| 3-GB-C | | 10.0% |
| 4-GB-C | | 10.0% |
| 2-BEB-C | | 12.0% |
| 3-BEB-C | | 4.0% |
| 3-PyB (F) -F | | 6.0% |
| 3-HEB-O4 | | 8.0% |
| 4-HEB-O2 | | 6.0% |
| 5-HEB-O1 | | 6.0% |
| 3-HEB-O2 | | 5.0% |
| 5-HEB-O2 | | 4.0% |
| 5-HEB-5 | | 5.0% |
| 4-HEB-5 | | 5.0% |
| 1O-BEB-2 | | 4.0% |
| 3-HHB-1 | | 4.0% |
| 3-HHEBB-C | | 3.0% |
| 3-HBEBB-C | | 3.0% |
| 5-HBEBB-C | | 3.0% |

Characteristics of this composition was determined to be as follows:

TNI=66.6° C.
$\eta$=40.3 mPa·s
$\Delta n$=0.121
$\Delta \epsilon$=11.5
Vth=1.30 V

COMPOSITION EXAMPLE 6

Liquid crystal composition comprising the following compounds in the content shown below was prepared.

| | | |
|---|---|---|
| F3-HB (F, F) B (F) -OCF2CF2H | (No. 92) | 7.0% |
| F6-HB-O1CF3 | (No. 14) | 4.0% |
| F7-B (F, F) B (F) -OCF2CF3 | (No. 35) | 4.0% |
| 3-HB-C | | 10.0% |
| 7-HB-C | | 3.0% |
| 1O1-HB-C | | 10.0% |
| 3-HB (F) -C | | 10.0% |
| 2-PyB-2 | | 2.0% |
| 3-PyB-2 | | 2.0% |
| 4-PyB-2 | | 2.0% |
| 1O1-HH-3 | | 7.0% |
| 2-BTB-O1 | | 7.0% |
| 3-HHB-F | | 4.0% |
| 3-HHB-O1 | | 4.0% |
| 3-HHB-3 | | 8.0% |
| 3-H2BTB-2 | | 3.0% |

-continued

| | |
|---|---|
| 3-H2BTB-3 | 3.0% |
| 2-PyBH-3 | 4.0% |
| 3-PyBH-3 | 3.0% |
| 3-PyBB-2 | 3.0% |

Characteristics of this composition was determined to be as follows:

TNI=64.6° C.
$\eta$=22.9 mPa·s
$\Delta n$=0.137
$\Delta \epsilon$=6.7
Vth=2.12 V

COMPOSITION EXAMPLE 7

Liquid crystal composition comprising the following compounds in the content shown below was prepared.

| | | |
|---|---|---|
| F7-B (F, F) B (F) -OCF2CF3 | (No. 35) | 5.0% |
| 3O1-BEB (F) -C | | 12.0% |
| 5O1-BEB (F) -C | | 4.0% |
| 1 V2-BEB (F, F) -C | | 10.0% |
| 3 HH-EMe | | 10.0% |
| 3-HB-O2 | | 18.0% |
| 7-HEB-F | | 2.0% |
| 3-HHEB-F | | 2.0% |
| 5-HHEB-F | | 2.0% |
| 3-HBEB-F | | 4.0% |
| 2O1-HBEB (F) -C | | 2.0% |
| 3-HB (F) EB (F) -C | | 2.0% |
| 3-HBEB (F, F) -C | | 2.0% |
| 3 HHB-F | | 4.0% |
| 3-HHB-O1 | | 4.0% |
| 3-HHB-3 | | 13.0% |
| 3-HEBEB-F | | 2.0% |
| 3-HEBEB-1 | | 2.0% |

Characteristics of this composition was determined to be as follows:

TNI=73.3° C.
$\eta$=34.9 mPa·s
$\Delta n$=0.115
$\Delta \epsilon$=21.6
Vth=1.12 V

COMPOSITION EXAMPLE 8

Liquid crystal composition comprising the following compounds in the content shown below was prepared.

| | | |
|---|---|---|
| F4-HHB (F) -O1CF2H | (No. 72) | 5.0% |
| 5-BEB (F) -C | | 5.0% |
| V-HB-C | | 11.0% |
| 5-PyB-C | | 6.0% |
| 4-BB-3 | | 11.0% |
| 3-HH-2V | | 10.0% |
| 5-HH-V | | 11.0% |
| V-HHB-1 | | 7.0% |
| V2-HHB-1 | | 15.0% |
| 3-HHB-1 | | 4.0% |
| 1V2-HBB-2 | | 10.0% |
| 3-HHEBH-3 | | 5.0% |

Characteristics of this composition was determined to be as follows:

TNI=88.4° C.
η=16.7 mPa·s
Δn=0.116
Δ∈=4.7
Vth=2.48 V

COMPOSITION EXAMPLE 9

Liquid crystal composition comprising the following compounds in the content shown below was prepared.

| F6-HB-O1CF3 | (No. 14) | 5.0% |
|---|---|---|
| 3O1-BEB (F) -C | | 12.0% |
| 5O1-BEB (F) -C | | 4.0% |
| 1V2-BEB (F, F) -C | | 16.0% |
| 3-HB-O2 | | 10.0% |
| 3-HH-4 | | 3.0% |
| 3-HHB-F | | 3.0% |
| 3-HHB-1 | | 8.0% |
| 3-HHB-O1 | | 4.0% |
| 3-HBEB-F | | 4.0% |
| 3-HHEB-F | | 7.0% |
| 5-HHEB-F | | 7.0% |
| 3-H2BTB-2 | | 4.0% |
| 3-H2BTB-3 | | 4.0% |
| 3-H2BTB-4 | | 4.0% |
| 3-HB (F) TB-2 | | 5.0% |

Characteristics of this composition was determined to be as follows:
TNI=87.1° C.
η=39.5 mPa·s
Δn=0.137
Δ∈=26.3
Vth=1.21 V

COMPOSITION EXAMPLE 10

Liquid crystal composition comprising the following compounds in the content shown below was prepared.

| F3-HB (F, F) B (F) -OCF2CF2H | (No. 92) | 7.0% |
|---|---|---|
| F7-B (F, F) B (F) -OCF2CF3 | (No. 35) | 4.0% |
| F4-HHB (F) -O1CF2H | (No. 72) | 5.0% |
| F5-B (F, F) B (F) B-OCF2CFHCF3 | (No. 129) | 7.0% |
| F5-HB (F, CL) B (F, F) -CF2CF2H | (No. 110) | 7.0% |
| 2-BEB-C | | 12.0% |
| 3-BEB-C | | 4.0% |
| 4-BEB-C | | 6.0% |
| 3-HB-C | | 3.0% |
| 3-HEB-O4 | | 12.0% |
| 4-HEB-O2 | | 8.0% |
| 5-HEB-O1 | | 8.0% |
| 3-HEB-O2 | | 6.0% |
| 5-HEB-O2 | | 5.0% |
| 3-HHB-1 | | 2.0% |
| 3-HHB-O1 | | 4.0% |

Characteristics of this composition was determined to be as follows:
TNI=55.3° C.
η=38.5 mPa·s
Δn=0.113
Δ∈=6.4
Vth=1.81 V

COMPOSITION EXAMPLE 11

Liquid crystal composition comprising the following compounds in the content shown below was prepared.

| F5-B (F, F) B (F) B-OCF2CFHCF3 | (No. 129) | 3.0% |
|---|---|---|
| 2-BEB-C | | 10.0% |
| 5-BB-C | | 12.0% |
| 7-BB-C | | 7.0% |
| 1-BTB-3 | | 7.0% |
| 2-BTB-1 | | 10.0% |
| 1O-BEB-2 | | 10.0% |
| 1O-BEB-5 | | 12.0% |
| 2-HHB-1 | | 4.0% |
| 3-HHB-F | | 4.0% |
| 3-HHB-1 | | 4.0% |
| 3-HHB-O1 | | 4.0% |
| 3-HHB-3 | | 13.0% |

Characteristics of this composition was determined to be as follows:
TNI=63.4° C.
η=21.2 mPa·s
Δn=0.161
Δ∈=6.5
Vth=1.78 V

COMPOSITION EXAMPLE 12

Liquid crystal composition comprising the following compounds in the content shown below was prepared.

| F3-HB (F, F) B (F) -OCF2CF2H | (No. 92) | 5.0% |
|---|---|---|
| F4-HHB (F) -O1CF2H | (No. 72) | 5.0% |
| 1V2-BEB (F, F) -C | | 8.0% |
| 3-HB-C | | 10.0% |
| V2V-HB-C | | 14.0% |
| V2V-HH-3 | | 19.0% |
| 3-HB-O2 | | 4.0%; |
| 3-HHB-3 | | 15.0% |
| 3-HB (F) TB-2 | | 4.0% |
| 3-HB (F) TB-3 | | 4.0% |
| 3-H2BTB-2 | | 4.0% |
| 3-H2BTB-3 | | 4.0% |
| 3-H2BTB-4 | | 4.0% |

Characteristics of this composition was determined to be as follows:
TNI=93.8° C.
η=20.8 mPa·s
Δn=0.131
Δ∈=7.7
Vth=2.38 V

COMPOSITION EXAMPLE 13

Liquid crystal composition comprising the following compounds in the content shown below was prepared.

| F5-HB (F, CL) B (F, F)-CF2CF2H | (No. 129) | 3.0% |
|---|---|---|
| 5-BTB (F) TB-3 | | 10.0% |
| V2-HB-TC | | 10.0% |
| 3-HB-TC | | 10.0% |
| 3-HB-C | | 7.0% |
| 5-HB-C | | 7.0% |
| 5-BB-C | | 3.0% |
| 2-BTB-1 | | 10.0% |
| 2-BTB-O1 | | 5.0% |
| 3-HH-4 | | 5.0% |

| | | |
|---|---|---|
| 3-HHB-1 | | 10.0% |
| 3-HHB-3 | | 11.0% |
| 3-H2BTB-2 | | 3.0% |
| 3-H2BTB-3 | | 3.0% |
| 3-HB (F) TB-2 | | 3.0% |

Characteristics of this composition was determined to be as follows:
TNI=100.3° C.
η=15.3 mPa·s
Δn=0.205
Δ∈=6.4
Vth=2.36 V

COMPOSITION EXAMPLE 14

Liquid crystal composition comprising the following compounds in the content shown below was prepared.

| | | |
|---|---|---|
| F3-HB (F, F) B (F) -OCF2CF2H | (No. 92) | 5.0% |
| F6-HB-O1CF3 | (No. 14) | 5.0% |
| F5-B (F, F) B (F) B-OCF2CFHCF3 | (No. 129) | 5.0% |
| 1V2-BEB (F, F) -C | | 6.0% |
| 3-HB-C | | 3.0% |
| 2-BTB-1 | | 10.0% |
| 5-HH-VFF | | 30.0% |
| 1-BHH-VFF | | 8.0% |
| 1-BHH-2VFF | | 11.0% |
| 3-H2BTB-2 | | 5.0% |
| 3-H2BTB-3 | | 4.0% |
| 3-H2BTB-4 | | 4.0% |
| 3-HHB-1 | | 4.0% |

Characteristics of this composition was determined to be as follows:
TNI=77.3° C.
η=17.6 mPa·s
Δn=0.125
Δ∈=4.2
Vth=2.76 V

COMPOSITION EXAMPLE 15

Liquid crystal composition comprising the following compounds in the content shown below was prepared.

| | | |
|---|---|---|
| F7-B (F, F) B (F) -OCF2CF3 | (No. 35) | 2.0% |
| 2-HB-C | | 5.0% |
| 3-HB-C | | 10.0% |
| 3-HB-O2 | | 15.0% |
| 2-BTB-1 | | 3.0% |
| 3-HHB-1 | | 8.0% |
| 3-HHB-F | | 4.0% |
| 3-HHB-O1 | | 5.0% |
| 3-HHB-3 | | 14.0% |
| 3-HHEB-F | | 4.0% |
| 5-HHEB-F | | 4.0% |
| 2-HHB (F) -F | | 7.0% |
| 3-HHB (F) -F | | 7.0% |
| 5-HHB (F) -F | | 7.0% |
| 3-HHB (F, F) -F | | 5.0% |

Characteristics of this composition was determined to be as follows:
TNI=98.4° C.
η=18.4 mPa·s
Δn=0.101
Δ∈=4.3
Vth=2.64 V

COMPOSITION EXAMPLE 16

Liquid crystal composition comprising the following compounds in the content shown below was prepared.

| | | |
|---|---|---|
| F3-HB (F, F) B (F) -OCF2CF2H | (No. 92) | 13.0% |
| 2-HHB (F) -F | | 17.0% |
| 3-HHB (F) -F | | 17.0% |
| 5-HHB (F) -F | | 16.0% |
| 2-H2HB (F) -F | | 10.0% |
| 3-H2HB (F) -F | | 5.0% |
| 5-H2BB (F) -F | | 10.0% |
| 2-HBB (F) -F | | 6.0% |
| 3-HBB (F) -F | | 6.0% |

Characteristics of this composition was determined to be as follows:
TNI=96.8° C.
η=26.6 mPa·s
Δn=0.090
Δ∈=5.0
Vth=2.31 V Further, a secondary composition was obtained by mixing 0.3 part of the optically active compound expressed by the formula (Op-8) described above with 100 parts of the primary composition described above. Characteristic of the secondary composition was determined to be as follows:
P=77 μm

COMPOSITION EXAMPLE 17

Liquid crystal composition comprising the following compounds in the content shown below was prepared.

| | | |
|---|---|---|
| F6-HB-O1CF3 | (No. 14) | 3.0% |
| F7-B (F, F) B (F) -OCF2CF3 | (No. 35) | 3.0% |
| 7-HB (F) -F | | 5.0% |
| 5-H2B (F) - F | | 5.0% |
| 3-HB-O2 | | 10.0% |
| 3-HH-4 | | 2.0% |
| 3-HH [5D, 6D, 7D] -4 | | 3.0% |
| 2-HHB (F) -F | | 10.0% |
| 3-HHB (F) -F | | 10.0% |
| 5-HH [5D, 6D, 7D] B (F) -F | | 10.0% |
| 3-H2HB (F) -F | | 5.0% |
| 2-HBB (F) -F | | 3.0% |
| 3-HBB (F) -F | | 3.0% |
| 2-H2BB (F) -F | | 5.0% |
| 3-H2BB (F) -F | | 6.0% |
| 3-HHB- 1 | | 8.0% |
| 3-HHB-O1 | | 5.0% |
| 3-HHB- 3 | | 4.0% |

Characteristics of this composition was determined to be as follows:
TNI=82.7° C.
η=17.2 mPa·s
Δn=0.089
Δ∈=3.2
Vth=2.73 V

COMPOSITION EXAMPLE 18

Liquid crystal composition comprising the following compounds in the content shown below was prepared.

| | | |
|---|---|---|
| F3-HB- (F, F) B (F) -OCF2CF2H | (No. 92) | 4.0% |
| F4-HHB (F) -O1CF2H | (No. 72) | 4.0% |
| F5-B (F, F) B (F) B-OCF2CFHCF3 | (No. 129) | 4.0% |
| F5-HB (F, CL) B (F, F) -CF2CF2H | (No. 110) | 4.0% |
| 7-HB (F, F) -F | | 3.0% |
| 3-HB-O2 | | 7.0% |
| 2-HHB (F) -F | | 10.0% |
| 3-HHB (F) -F | | 10.0% |
| 5-HHB (F) -F | | 10.0% |
| 2-HBB (F) -F | | 9.0% |
| 3-HBB (F) -F | | 9.0% |
| 2-HBB-F | | 4.0% |
| 3-HBB-F | | 4.0% |
| 5-HBB-F | | 3.0% |
| 3-HBB (F, F) -F | | 5.0% |
| 5-HBB (F, F) -F | | 10.0% |

Characteristics of this composition was determined to be as follows:

TNI=81.1° C.

η=26.1 mPa·s

Δn=0.111

Δ∈=5.8

Vth=1.99 V

COMPOSITION EXAMPLE 19

Liquid crystal composition comprising the following compounds in the content shown below was prepared.

| | | |
|---|---|---|
| F4-HHB (F) -O1CF2H | (No. 72) | 5.0% |
| 7-HB (F, F) -F | | 3.0% |
| 3-H2HB (F, F) -F | | 12.0% |
| 4-H2HB (F, F) -F | | 10.0% |
| 5-H2HB (F, F) -F | | 10.0% |
| 3-HHB (F, F) -F | | 5.0% |
| 3-HH2B (F, F) -F | | 15.0% |
| 5-HH2B (F, F) -F | | 10.0% |
| 3-HBB (F, F) -F | | 12.0% |
| 5-HBB (F, F) -F | | 12.0% |
| 3-HBCF2OB (F, F) -F | | 6.0% |

Characteristics of this composition was determined to be as follows:

TNI=73.8° C.

η=25.7 mPa·s

Δn=0.089

Δ∈=8.4

Vth=1.72 V

COMPOSITION EXAMPLE 20

Liquid crystal composition comprising the following compounds in the content shown below was prepared.

| | | |
|---|---|---|
| F5-B (F, F) B (F) B-OCF2CFHCF3 | (No. 129) | 5.0% |
| 7-HB (F, F) -F | | 5.0% |
| 3-H2HB (F, F) -F | | 12.0% |
| 4-H2HB (F, F) LF | | 10.0% |
| 3-HHB (F, F) -F | | 10.0% |
| 3-HBB (F, F) -F | | 10.0% |
| 3-HHEB (F, F) -F | | 10.0% |
| 4-HHEB (F, F) -F | | 3.0% |
| 5-HHEB (F, F) -F | | 3.0% |

-continued

| | | |
|---|---|---|
| 2-HBEB (F, F) -F | | 3.0% |
| 3-HBEB (F, F) -F | | 5.0% |
| 5-HBEB (F, F) -F | | 3.0% |
| 3-HGB (F, F) -F | | 15.0% |
| 3-HHBB (F, F) -F | | 6.0% |

Characteristics of this composition was determined to be as follows:

TNI=74.5° C.

η=34.4 mPa·s

Δn=0.087

Δ∈=12.8

Vth=1.46 V

COMPOSITION EXAMPLE 21

Liquid crystal composition comprising the following compounds in the content shown below was prepared.

| | | |
|---|---|---|
| F3-HB (F, F) B (F) -OCF2CF2H | (No. 92) | 7.0% |
| F7-B (F, F) B (F) -OCF2CF3 | (No. 35) | 7.0% |
| 3-HB-CL | | 10.0% |
| 5-HB-CL | | 4.0% |
| 7-HB-CL | | 4.0% |
| 1O1-HH-5 | | 5.0% |
| 2-HBB (F) -F | | 8.0% |
| 3-HBB (F) -F | | 8.0% |
| 4-HHB-CL | | 8.0% |
| 5-HHB-CL | | 8.0% |
| 3-H2HB (F) -CL | | 4.0% |
| 3-HBB (F, F) -F | | 10.0% |
| 5-H2BB (F, F) -F | | 9.0% |
| 3-HB (F) VB-2 | | 4.0% |
| 3-HB (F) VB-3 | | 4.0% |

Characteristics of this composition was determined to be as follows:

TNI=79.4° C.

η=20.7 mPa·s

Δn=0.128

Δ∈=4.8

Vth=2.48 V

COMPOSITION EXAMPLE 22

Liquid crystal composition comprising the following compounds in the content shown below was prepared.

| | | |
|---|---|---|
| F3-HB (F, F) B (F) -OCF2CF2H | (No. 92) | 10.0% |
| F4-HHB (F) -O1CF2H | (No. 72) | 10.0% |
| 3-HHB (F, F) -F | | 9.0% |
| 3-H2HB (F, F) -F | | 8.0% |
| 4-H2HB (F, F) -F | | 8.0% |
| 5-H2HB (F, F) -F | | 8.0% |
| 3-HBB (F, F) -F | | 21.0% |
| 3-H2BB (F, F) -F | | 10.0% |
| 5-HHBB (F, F) -F | | 3.0% |
| 5-HHEBB-F | | 2.0% |
| 3-HH2BB (F, F) -F | | 3.0% |
| 1O1-HBBH-4 | | 4.0% |
| 1O1-HBBH-5 | | 4.0% |

Characteristics of this composition was determined to be as follows:

TNI=101.2° C.
η=35.5 mPa·s
Δn=0.118
Δ∈=8.6
Vth=1.89 V

While this composition was allowed to stand at −20° C. for 60 days, it showed nematic phase without developing crystals and smectic phase; and its voltage holding ratio was 98% at 20° C. and 96% after allowed to stand at 100° C. for 1 hour.

COMPOSITION EXAMPLE 23

Liquid crystal composition comprising the following compounds in the content shown below was prepared.

| F7-B (F, F) B (F) -OCF2CF3 | (No. 35) | 5.0% |
|---|---|---|
| 5-HB-F | | 12.0% |
| 6-HB-F | | 9.0% |
| 7-HB-F | | 7.0% |
| 2-HHB-OCF3 | | 7.0% |
| 3-HHB-OCF3 | | 7.0% |
| 4-HHB-OCF3 | | 7.0% |
| 5-HHB-OCF3 | | 5.0% |
| 3-HH2B-OCF3 | | 4.0% |
| 5-HH2 B-OCF3 | | 4.0% |
| 3-HHB (F, F) -OCF3 | | 5.0% |
| 3-HBB (F) -F | | 10.0% |
| 5-HBB (F) -F | | 5.0% |
| 3-HH2B (F) -F | | 3.0% |
| 3-HB (F) BH-3 | | 3.0% |
| 5-HBBH-3 | | 3.0% |
| 3-HHB (F, F) -OCF2H | | 4.0% |

Characteristics of this composition was determined to be as follows:
TNI=78.1° C.
η=14.4 mPa·s
Δn=0.092
Δ∈=4.5
Vth=2.40 V

COMPOSITION EXAMPLE 24

Liquid crystal composition comprising the following compounds in the content shown below was prepared.

| F5-HB (F, CL) B (F, F) -CF2CF2H | (No. 110) | 2.0% |
|---|---|---|
| 5-H4HB (F, F) -F | | 7.0% |
| 5-H4HB-OCF3 | | 15.0% |
| 3-H4HB (F, F) -CF3 | | 8.0% |
| 5-H4HB (F, F) -CF3 | | 10.0% |
| 3-HB-CL | | 6.0% |
| 5-HB-CL | | 4.0% |
| 2-H2BB (F) -F | | 5.0% |
| 3-H2BB (F) -F | | 10.0% |
| 5-HVHB (F, F) -F | | 5.0% |
| 3-HHB-OCF3 | | 5.0% |
| 3-H2HB-OCF3 | | 5.0% |
| V-HHB (F) -F | | 5.0% |
| 3-HHB (F) -F | | 3.0% |
| 5-HHEB-OCF3 | | 2.0% |
| 3-HBEB (F, F) -F | | 5.0% |
| 5-HH-V2F | | 3.0% |

Characteristics of this composition was determined to be as follows:

TNI=67.7° C.
η=25.8 mPa·s
Δn=0.094
Δ∈=8.0
Vth=1.91 V

COMPOSITION EXAMPLE 25

Liquid crystal composition comprising the following compounds in the content shown below was prepared.

| F6-HB-O1CF3 | (No. 14) | 4.0% |
|---|---|---|
| 2-HHB (F) -F | | 2.0% |
| 3-HHB (F) -F | | 2.0% |
| 5-HHB (F) -F | | 2.0% |
| 2-HBB (F) -F | | 6.0% |
| 3-HBB (F) -F | | 6.0% |
| 5-HBB (F) -F | | 6.0% |
| 2-H2BB (F) -F | | 9.0% |
| 3-H2BB (F) -F | | 9.0% |
| 3-HBB (F, F) -F | | 25.0% |
| 5-HBB (F, F) -F | | 19.0% |
| 1O1-HBBH-4 | | 5.0% |
| 1O1-HBBH-5 | | 5.0% |

Characteristics of this composition was determined to be as follows:
TNI=90.7° C.
η=34.4 mPa·s
Δn=0.130
Δ∈=7.2
Vth=2.00 V Further, a secondary composition was obtained by mixing 0.25 part of the optically active compound expressed by the formula (Op-5) described above with 100 parts of the primary composition described above. Characteristic of the secondary composition was determined to be as follows:
P=63 μm

COMPOSITION EXAMPLE 26

Liquid crystal composition comprising the following compounds in the content shown below was prepared.

| F5-B (F, F) B (F) B-OCF2CFHCF3 | (No. 129) | 5.0% |
|---|---|---|
| 5-HB-CL | | 12.0% |
| 3-HH-4 | | 7.0% |
| 3-HB-O2 | | 20.0% |
| 3-H2HB (F, F) -F | | 8.0% |
| 3-HHB (F, F) -F | | 8.0% |
| 3-HBB (F, F) -F | | 6.0% |
| 2-HHB (F) -F | | 5.0% |
| 5-HHB (F) -F | | 5.0% |
| 2-H2HB (F) -F | | 2.0% |
| 3-H2HB (F) -F | | 1.0% |
| 5-H2HB (F) -F | | 2.0% |
| 3-HHBB (F, F) -F | | 4.0% |
| 3-HBCF2OB-OCF3 | | 4.0% |
| 5-HBCF2OB (F, F) -CF3 | | 4.0% |
| 3-HHB-1 | | 3.0% |
| 3-HHB-O1 | | 4.0% |

Characteristics of this composition was determined to be as follows:
TNI=69.5° C.
η=17.3 mPa·s
Δn=0.085

$\Delta \in = 4.1$
Vth=2.27 V
Compounds of the present invention expressed by the general formula (1) can be produced by freely using known methods of organic synthesis and examples of which are shown below.
I. Production of intermediate materials (compounds expressed by the formula (23), (30), (41), (42), or (43)) in which a second electron withdrawing group (a fluoroalkyl group) is introduced
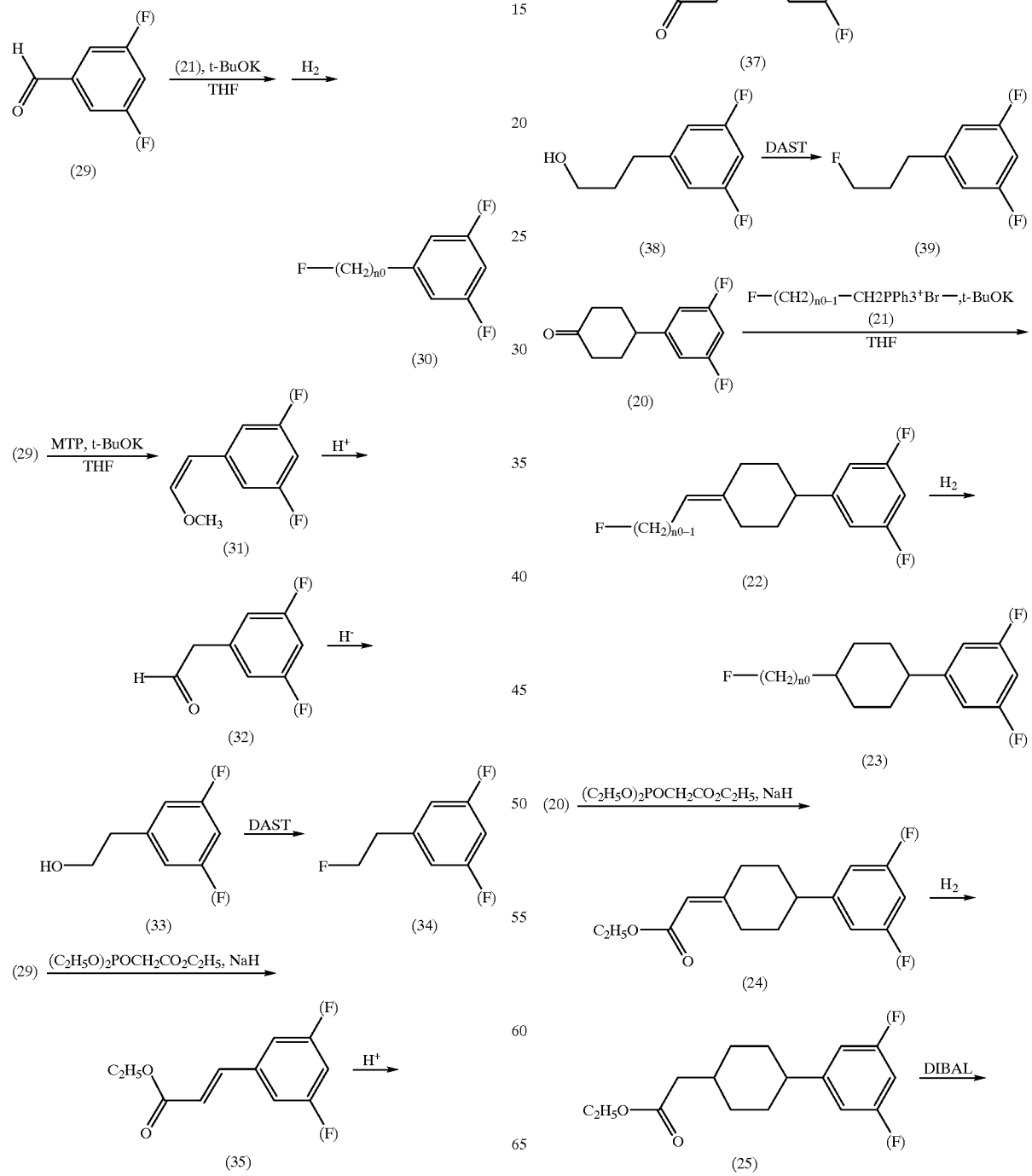

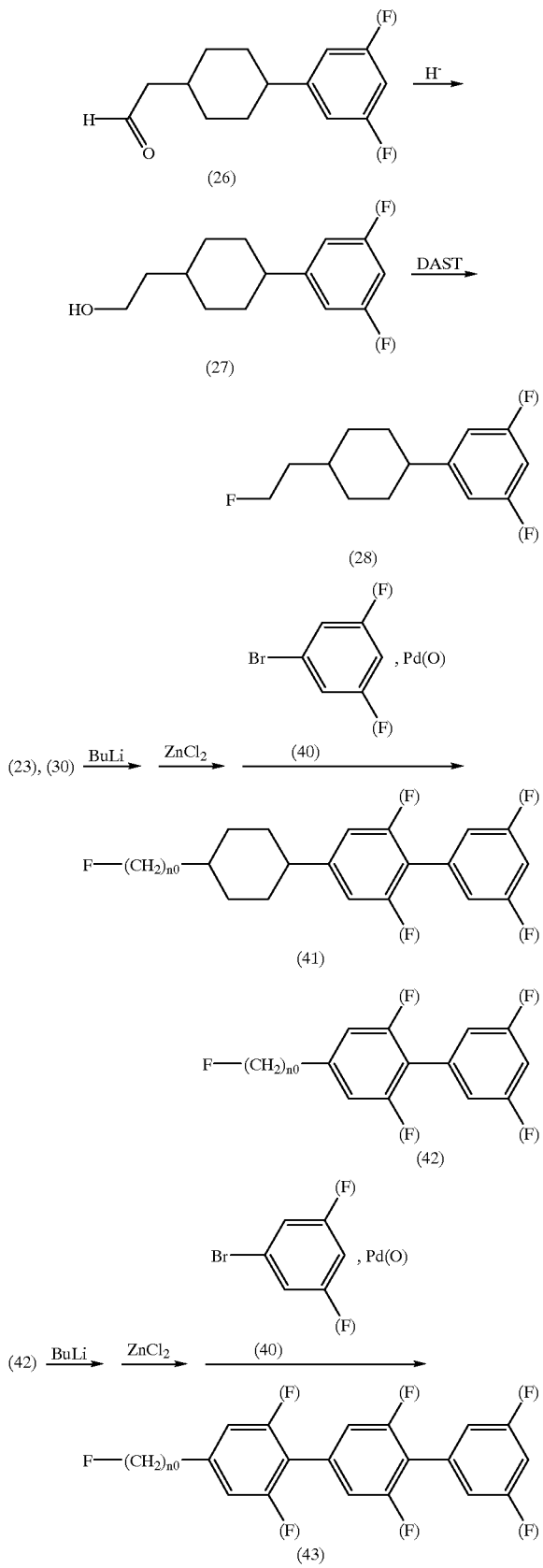

Production of compounds expressed by the formula (23):

Compound expressed by the formula (23) can be obtained by reacting phenylcyclohexanone (20) with an ylide prepared from phosphonium salt (21) and a base such as potassium-t-butoxide (t-BuOK) in tetrahydrofuran (THF) to obtain compound (22), and then hydrogenating it in the presence of a catalyst such as Pd/C.

Compounds expressed by the formula (23) in which n0 is 2 are preferably produced by the method as follows:

That is, ethyl diethylphosphonoacetate is reacted with sodium hydride in a solvent which does not participate in the reaction such as dimethoxyethane, and then phenyl-cyclohexanone (20) is reacted with the reaction solution. The compound (24) thus obtained is hydrogenated in the presence of a Pd/C catalyst to obtain ethyl ester derivative (25), diisobutyl-aluminum hydride (hereinafter abbreviated as DIBAL) is reacted with toluene solution of the derivative (25) to obtain aldehyde derivative (26), and this derivative is converted into alcohol derivative (27) with a reducing agent such as sodium borohydride. Objective compound (28) can be obtained by reacting diethylaminosulfur trifluoride (hereinafter abbreviated to DAST) with the derivative (27) in a solvent which does not participate in the reaction such as dichloromethane and ethylene glycol dimethyl ether.

Production of compounds expressed by the formula (30):

Compounds expressed by the formula (30) can be synthesized by the same method as that described above for synthesizing the compounds expressed by the formula (23) with the exception that phenylcyclohexanone (20) is changed to benzaldehyde derivative (29).

Further, compounds expressed by the formula (30) in which n0 is 2 or 3 can also preferably be produced by the following method.

(Production of compounds in which n0 is 2)

The benzaldehyde derivative (29) described above is reacted with an ylide prepared from methoxymethyltriphenylphosphonium bromide (hereinafter abbreviated to MTP) and t-BuOK in THF to obtain compound (31), and this compound is treated with an acid to form aldehyde derivative (32). Subsequently, the objective compound (34) can be obtained by the same method as that described above for obtaining compound (28) with the exception that the derivative (32) is used in place of aldehyde derivative (26).

(Production of compounds in which n0 is 3)

Objective compound (39) can be obtained by the same method as that described above for obtaining compound (28) with the exception that the phenylcyclohexanone (20) is changed to benzaldehyde derivative (29).

Production of the compounds expressed by the formula (41), (42), or (43):

(Production of the compounds expressed by the formula (41) or (42))

Compounds expressed by the formula (41) or (42) can be obtained, respectively, by reacting butyl lithium (BuLi) with the compound expressed by the formula (23) or (30) described above, and then reacting zinc chloride (ZnCl₂), Pd(0), and compound (40) in turn with the lithio compound obtained. While this result is obtained by applying a method described in J. Org. Chem., 42, 1821 (1977), another method described in J. Chem. Soc. Perkin Trans. 2, 2041 (1989) can also be applied.

(Production of the compounds expressed by the formula (43))

Objective compound (43) can be obtained by the same method as described above with the exception that the compound expressed by the formula (30) mentioned above is changed to compound (42).

wherein n0 has the same meaning as described above.

II. Production of examples of the compounds of the present invention in which a first electron withdrawing group (a fluoroalkyl group or fluoroalkoxy group) is introduced
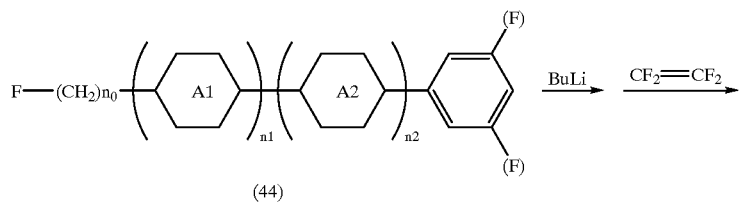
(44)
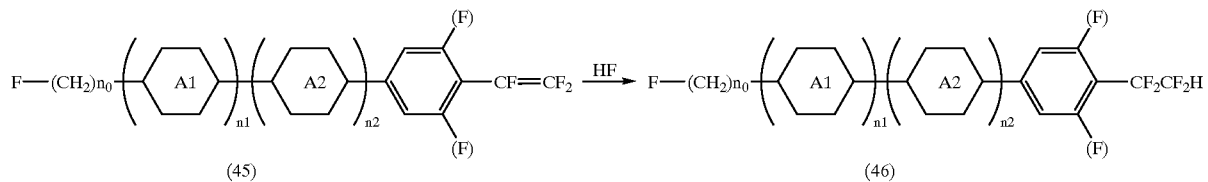
(45) (46)
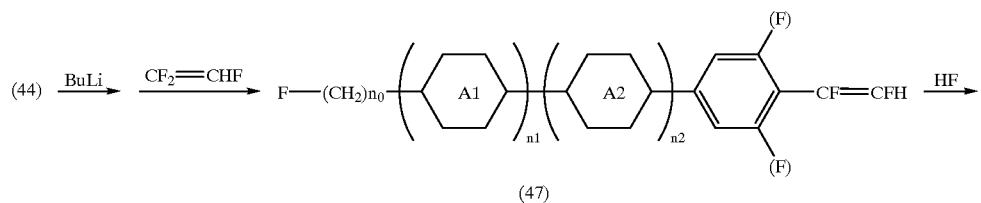
(47)
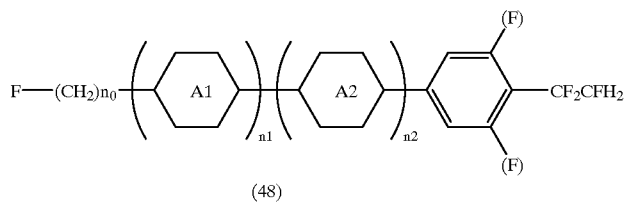
(48)
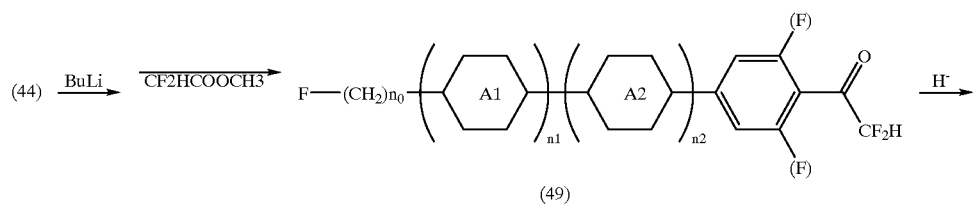
(49)
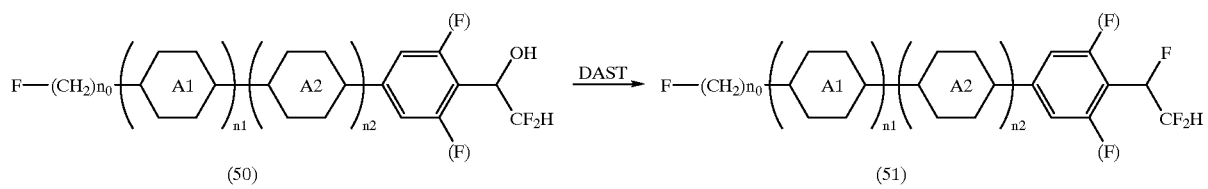
(50) (51)
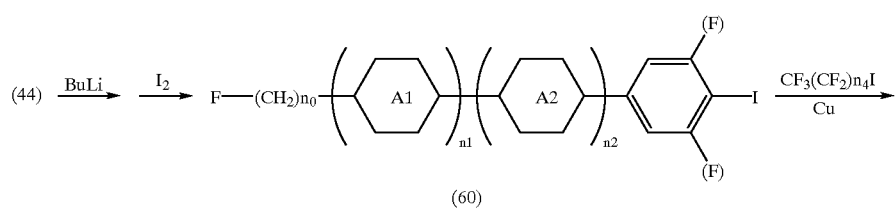
(60)
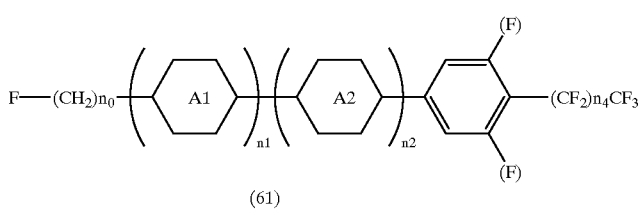
(61)

-continued
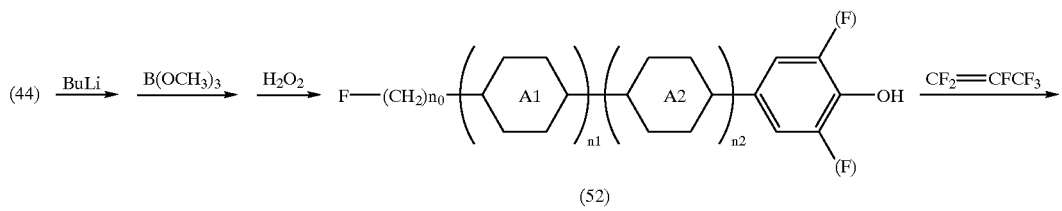
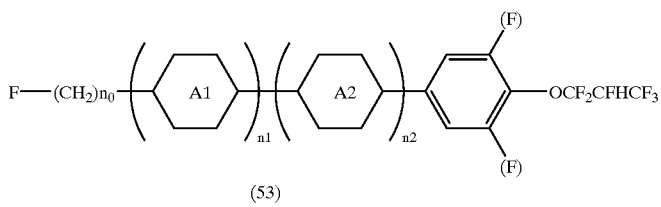
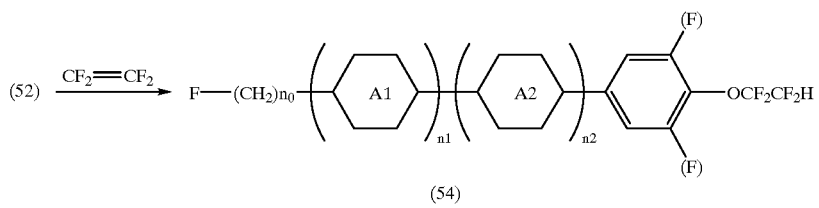
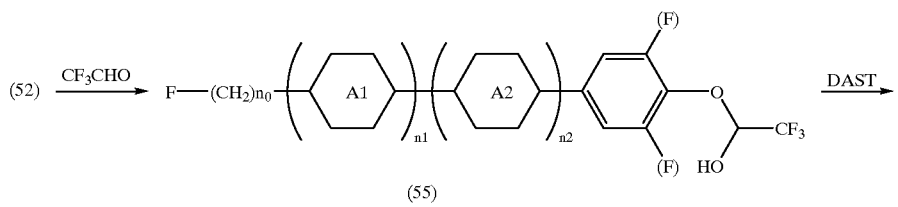
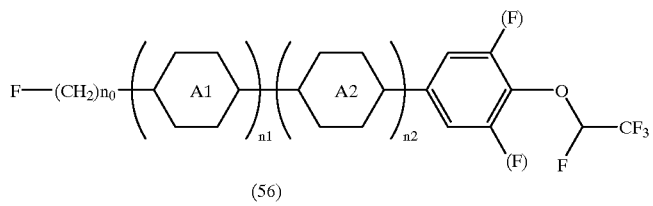
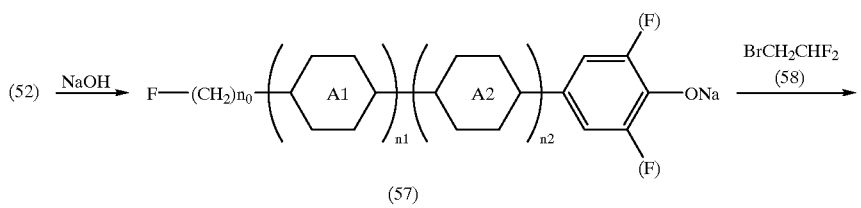
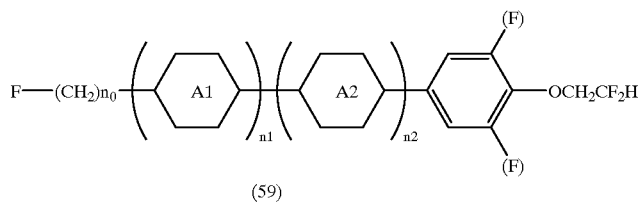
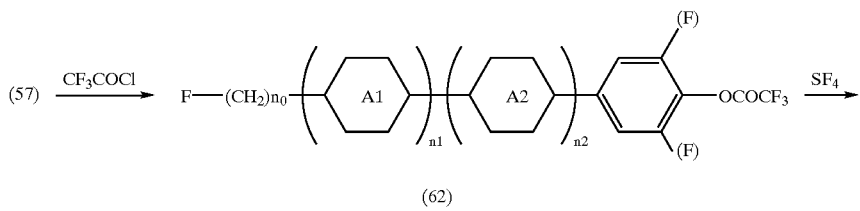

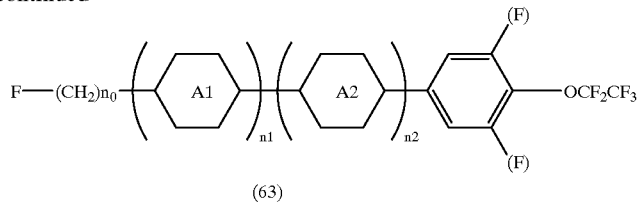

(63)

wherein n0, n1, n2, ring A1, and ring A2 have the same meaning as described above.

Intermediate materials obtained in the production examples described above and expressed by the formula (23), (30), (41), (42), or (43) are expressed by the general formula (44) together, and examples of methods for producing the compounds of the present invention using the compounds of the general formula (44) as starting material are described below.

Production of compounds in which fluoroalkyl groups is $CF_2CF_2H$:

These compounds can be produced in the same manner as described above by using a method described in DE 4329592 A1 described above.

That is, the objective compound expressed by the general formula (46) can be obtained by reacting BuLi with compound (44) which is a starting material, reacting tetrafluoroethylene ($CF_2=CF_2$) with the lithiated compound thus obtained to obtain the compounds expressed by the general formula (45), and then reacting hydrogen fluoride therewith or reacting difluoroacetic acid ester (omitted in the diagrams) with the litiated compound described above followed by the reaction with DAST or sulfur tetrafluoride.

Production of compounds in which fluoroalkyl group is $CF_2CFH_2$:

These compounds can also be produced in the same manner as described above by using a method described in DE 4329592 A1 mentioned above.

That is, the objective compound expressed by the general formula (48) can be obtained by reacting BuLi with compound (44) which is a starting material, to obtain a lithiated compound, reacting trifluoroethylene ($CF_2=CHF$) with the lithiated compound to obtain the compound expressed by the general formula (47), and then reacting HF with the compound of the general formula (47).

Production of compounds in which fluoroalkyl group is $CFHCF_2H$:

These compounds can also be produced in the same manner as described above by using a method described in DE 4329592 A1 mentioned above.

That is, the objective compound expressed by the general formula (51) can be obtained by reacting BuLi with compound (44) which is a starting material, to obtain a lithiated compound, reacting methyl difluoroacetate ($CF_2HCOOCH_3$) with the lithiated compound to obtain the compound expressed by the general formula (49), reacting a reducing agent such as sodium borohydride with the compound of the general formula (49) to convert it into the compound expressed by the general formula (50), and then reacting DAST therewith.

Production of compounds in which fluoroalkyl group is $(CF_2)_{n4}CF_3$ (n4 is an integer of 1 to 6):

Compound (44) which is a starting material is lithiated and then iodinated to obtain the iodobenzene derivative expressed by the general formula (60). Then, the objective compound expressed by the general formula (61) can be obtained by reacting copper powders with perfluoroalkyl halide ($CF_3(CF_2)_{n4}I$) in an aprotic solvent according to a method described, for example, in Jikken Kagaku Kouza (Course of Chemical Experiment), fourth edition, vol. 19, p 403, and then reacting the iodobenzene derivative (60) obtained by the procedure described above, with the solution of the complex formed by previous reaction.

Production of compounds in which fluoroalkoxy group is $OCF_2CFHCF_3$:

These compounds can be produced by using a method described in DE 19513007 A1 mentioned above.

That is, BuLi is reacted with compound (44) which is a starting material, to obtain a lithiated compound and reacting trimethyl borate ($B(OCH_3)_3$) or triisopropyl borate with the lithiated compound. Objective compound expressed by the general formula (53) can be obtained by reacting a peroxide such as hydrogen peroxide, performic acid, and peracetic acid with the product formed by previous reaction, to obtain the phenol derivative expressed by the general formula (52), and then reacting hexafluoropropene ($CF_2=CFCF_3$) with the phenol derivative in the presence of a base such as t-BuOK under normal pressure or raised pressure, preferably raised pressure.

Production of compounds in which fluoroalkoxy group is $OCF_2CF_2H$:

These compounds can be produced by using a method described in DE 4142519 A1 mentioned above.

That is, the objective compound expressed by the general formula (54) can be obtained by reacting tetrafluoroethylene ($CF_2=CF_2$) with the phenol derivative expressed by the general formula (52) described above in the presence of a base such as BuLi under normal pressure or raised pressure, preferably raised pressure.

Production of compounds in which fluoroalkoxy group is $OCFHCF_3$:

These compounds can be produced by using a method described in DE 4308028 A1 mentioned above.

That is, the objective compounds expressed by the general formula (56) can be obtained by reacting trifluoroacetaldehyde ($CF_3CHO$), and hydrogen fluoride or DAST in turn with the phenol derivative expressed by the general formula (52) described above.

Production of compounds in which fluoroalkoxy group is $OCH_2CF_2H$:

These compounds can be produced by using a method described in Laid-open Japanese Patent Publication No. Hei 6-329573.

That is, the objective compounds expressed by the general formula (59) can be obtained by reacting a base such as sodium hydroxide to the phenol derivative expressed by the general formula (52) described above to obtain the phenoxide derivative expressed by the general formula (57), and then reacting 1-bromo-2,2-difluoroethane ($BrCH_2CHF_2$) with the phenoxide derivative in a solvent which does not participate in the reaction.

Production of compounds in which fluoroalkoxy group is $OCF_2CF_3$:

These compounds can be produced by using a method described in the DE 4142519 A1 mentioned above.

That is, the objective compounds expressed by the general formula (63) can be obtained by reacting trifluoroacetic acid chloride ($CF_3COCl$) with the phenoxide derivative expressed by the general formula (57) in a solvent which does not participate in the reaction such as THF to obtain the compound expressed by the general formula (62), and then reacting sulfur tetrafluoride ($SF_4$) with the compound of the general formula (62).

Further, the compounds of the present invention expressed by the general formula (1) and having silacyclohexane ring can readily be produced by methods described in Laid-open Japanese Patent Publication Nos. Hei 7-70148, Hei 7-112990, Hei 7-173176, and Hei 7-252273, respectively.

Now, the present invention will be described in more detail with reference to Examples. However, it should be understood that the scope of the present invention is by no means restricted by such specific examples.

In each of the Examples, C indicates crystal, S: smectic phase, N: nematic phase, and I: isotropic liquid phase, and the unit of all phase transition points is °C.

EXAMPLE 1

Preparation of 1-(4-(3-fluoropropyl)cyclohexyl)-4-(3-fluoro-4-(1,1,2,2-tetrafluoroethoxy)phenyl)-3,5-difluorobenzene (Compound expressed by the general formula (1) in which n0 is 3, n1 is 1, n2 is 1, ring A1 is the group expressed by the formula (a), ring A2 is the group expressed by the formula (d), $Q_1$ is fluorine atom, $Q_2$ is hydrogen atom, and Y is $CF_2CF_2H$ (Compound No. 92))

First Step

To 3 l of toluene was dissolved 200.0 g (1.42 mol) of 3-fluorobromopropane, 372 g (1.42 mol) of triphenylphosphine was added thereto, and refluxed for 15 hours. Deposited crystals were filtered off and subjected to suction drying to obtain 486 g (1.21 mol) of 3-fluoropropyltriphenylphosphine bromide. Yield of this compound from 3-fluorobromopropane was 85.2%.

Second Step

Grignard reagent was prepared from 50.0 g (259 mmol) of 3,5-difluorobromobenzene and 6.32 g (260 mmol) of dried magnesium in 350 ml of THF, and cooled down to 0° C. Solution of 40.6 g (260 mmol) of a commercially available cyclohexanedionemonoethylene ketal in 300 ml of THF was added dropwise thereto. After finishing of the dropping, the reaction product was warmed up to room temperature and stirred for 3 hours. The reaction product was added to 500 ml of 6N hydrochloric acid, the product was extracted with toluene, washed with saturated aqueous sodium bicarbonate solution and water, dried over magnesium sulfate, and the solvent was distilled off. To the residue was added 100 ml of toluene and 5 g of p-toluene sulfonic acid (hereinafter abbreviated to PTS) and refluxed for 5 hours with the water formed by the reaction being removed by a Dean and Stark. Subsequently, 2 g of ethylene glycol was added and refluxed for 2 hours. To the reaction product was added 200 ml of water, the organic layer was washed with saturated aqueous sodium bicarbonate solution and water in turn, dried over magnesium sulfate, and then the solvent was distilled off. The residue was purified by column chromatography treatment using toluene/ethyl acetate (4/1) as eluent, and then subjected to hydrogenation in ethanol using 2.02 g of 5% Pd/C as catalyst. After termination of the reaction, the catalyst was filtered off, and the ethanol was distilled off. After the concentrated product thus obtained was refluxed in 150 ml of formic acid for 3 hours, 400 ml of water was added to the reaction product, the product was extracted with toluene, the extract was washed with saturated aqueous sodium bicarbonate solution and water in turn, the toluene layer was dried over magnesium sulfate, and then the toluene was distilled off to obtain 20.2 g (96.1 mmol) of 4-(3,5-difluorophenyl)cyclohexanone. Yield of this product from 3,5-difluorobromobenzene was 37.1%.

Third Step

THF in an amount of 100 ml was added to 12.5 g (31.0 mmol) of the 3-fluoropropyltriphenylphosphine bromide synthesized in the first step, and cooled down to 0° C. under nitrogen gas atmosphere. Solution of 3.4 g (31.0 mmol) of potassium-t-butoxide in 30 ml of THF was added thereto and stirred for 3 hours. To this reaction product was added dropwise a solution of 5.0 g (23.8 mmol) of the 4-(3,5-difluorophenyl)cyclohexanone synthesized in the second step in 50 ml of THF at 0° C., stirred at the temperature as it was for 1 hour, warmed up to room temperature, and then stirred for further 4 hours. Water in an amount of 100 ml was added to the reaction product, the product was extracted with ethyl acetate, the extract was washed with saturated aqueous sodium bicarbonate solution and water in turn, and then the organic layer was dried over magnesium sulfate. The solvent was distilled off under a reduced pressure and the residue was purified by column chromatography treatment using toluene as eluent. The purified product was subjected to hydrogenation in ethanol in the presence of 5% Pd/C catalyst. After termination of the reaction, the catalyst was filtered off, the ethanol was distilled off under a reduced pressure to obtain 1.3 g (5.1 mmol) of 4-(3,5-difluorophenyl)-1-(3-fluoropropyl)cyclohexane. Yield of this product from 4-(3,5-difluorophenyl)cyclohexanone was 21%.

Fourth Step

THF in an amount of 10 ml was added to 1.3 g (5.1 mmol) of the 4-(3,5-difluorophenyl)-1-(3-fluoropropyl)cyclohexane synthesized in the third step, cooled down to −60° C. under nitrogen gas atmosphere, 3.8 ml (6.1 mmol) of 1.60N solution of n-butyl lithium in hexane was added dropwise by a syringe, stirred at the temperature as it was for 1 hour, and then 12.2 ml (6.1 mmol) of a solution of 0.5 mol of zinc chloride in THF was added dropwise thereto. After finishing of the dropping, the temperature of the reaction product was raised to room temperature and then stirred for 2 hours. After 250 mg of tetrakistriphenylphosphine palladium was added as catalyst to the reaction product, 1.7 g (5.8 mmol) of 3-fluoro-4-(1,1,2,2-tetrafluoroethoxy)bromobenzene was added dropwise, and then refluxed for 2 hours.

The reaction product was added to chilled 6N hydrochloric acid, the product was extracted with toluene, the extract was washed with saturated aqueous sodium bicarbonate solution and water in turn, dried over magnesium sulfate, and then the solvent was distilled off. The residue was purified by column chromatography treatment using toluene/heptane (1/1) as eluent on a silica gel, and recrystallized to synthesize 0.15 g (0.32 mmol) of the subject 1-(4-(3-fluoropropyl)cyclohexyl)-4-(3-fluoro-4-(1,1,2,2-tetrafluoroethoxy)phenyl)-3,5-difluorobenzene. Yield of this product from 4-(3,5-difluorophenyl)-1-(3-fluoropropyl)cyclohexane was 6.3%.

C-I point 95.5° C., I-N point 90.3° C. $^1$H-NMR (CDCl3) δ (ppm): 7.47~7.19 (m,3H), 6.85 (d, 2H), 5.99 (tt, 1H), 4.72 (t, 1H), 4.19 (t, 1H), 2.51 (m, 1H), 1.99~1.13 (m, 13H)

Based on the descriptions in Example 1 and the section of BEST MODE FOR CARRYING OUT THE INVENTION, the following compounds (Compound Nos. 1 through 166) can be prepared. In the following, compound obtained in Example 1 was shown again.

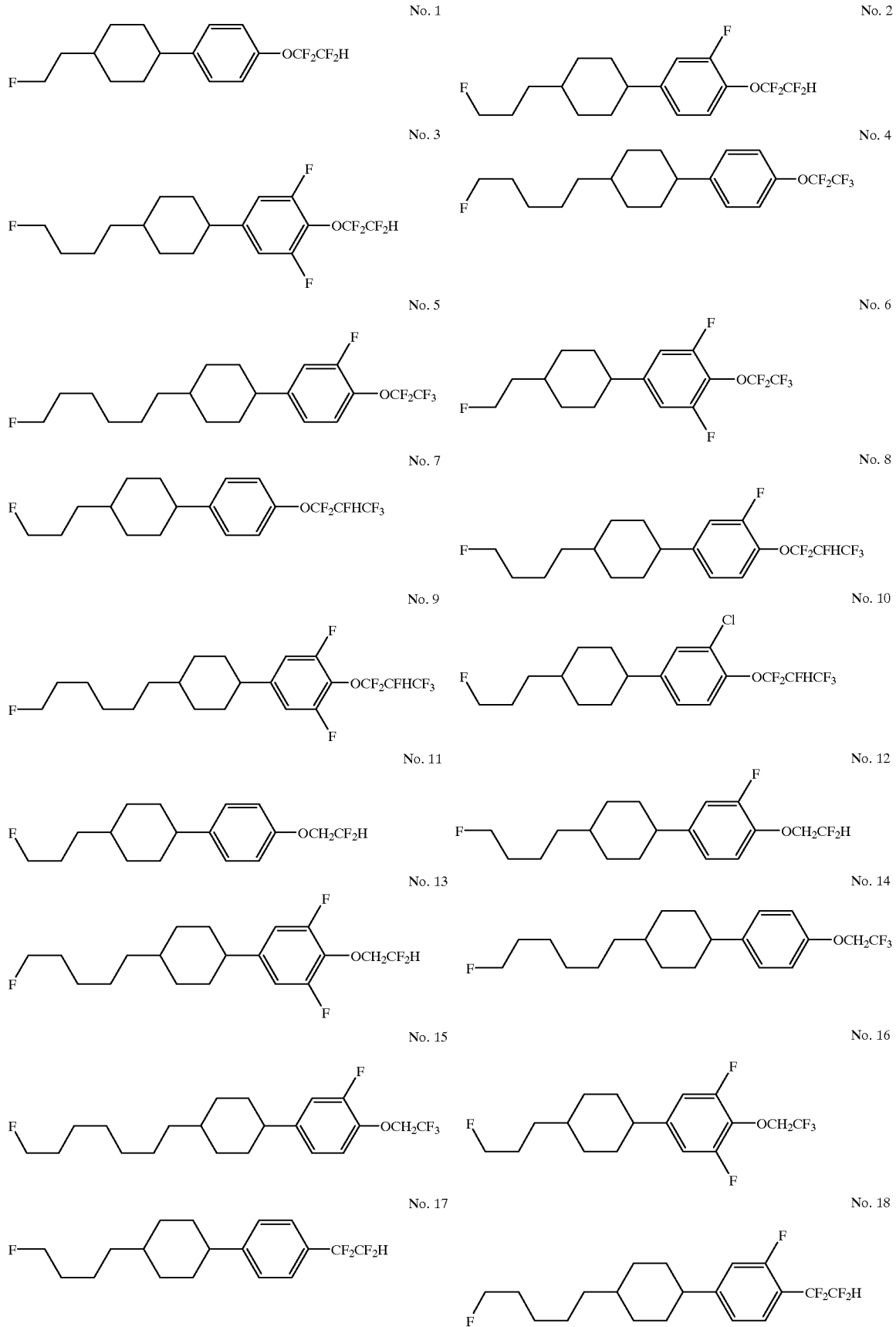

-continued
No. 19
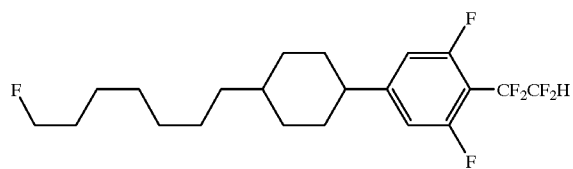
No. 20
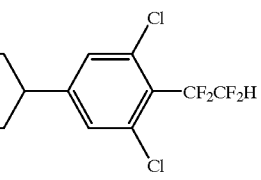
No. 21
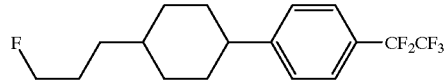
No. 22
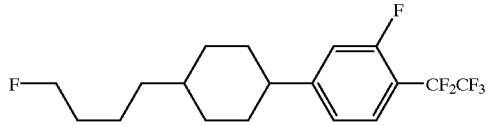
No. 23
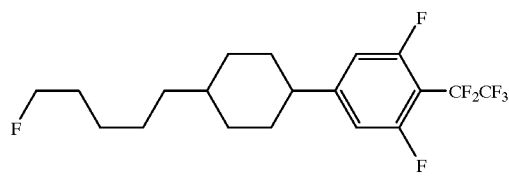
No. 24
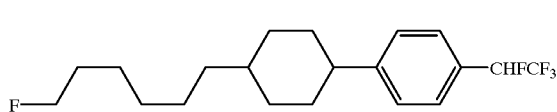
No. 25
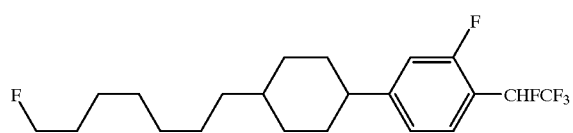
No. 26
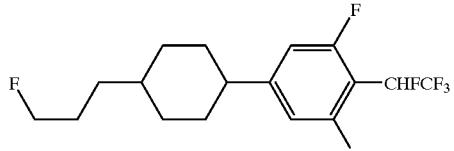
No. 27
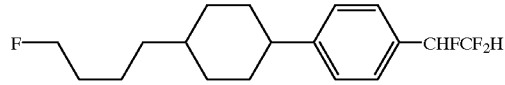
No. 28
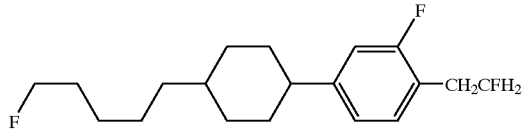
No. 29
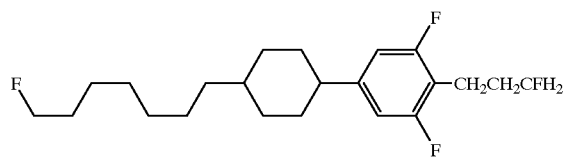
No. 30
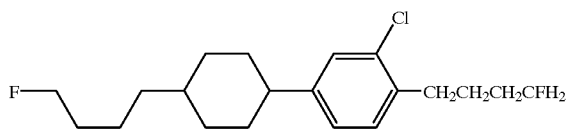
No. 31
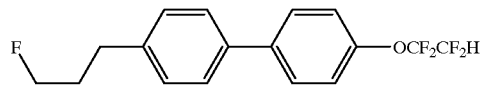
No. 32
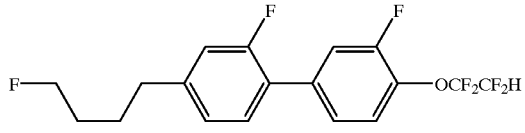
No. 33
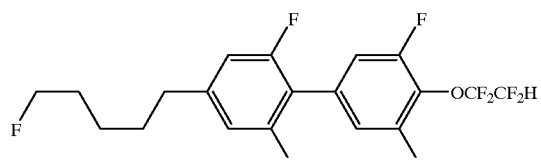
No. 34
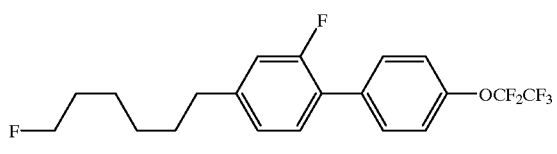
No. 35
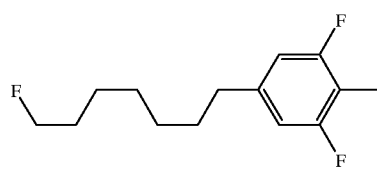
No. 36
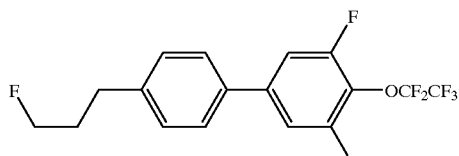

-continued
No. 37
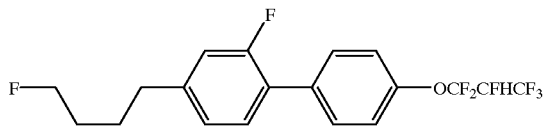
No. 38
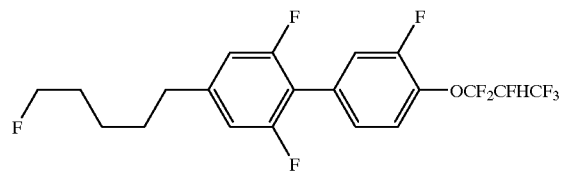
No. 39
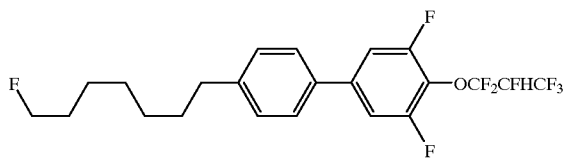
No. 40
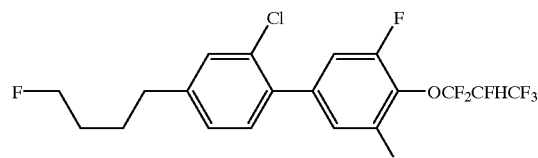
No. 41
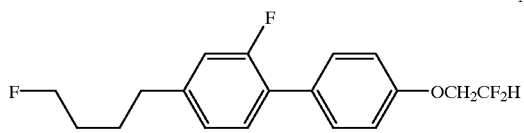
No. 42
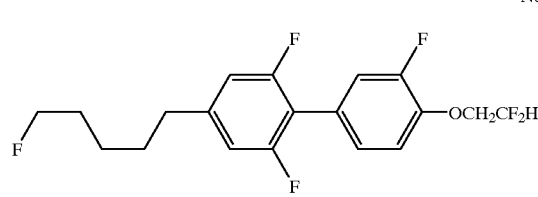
No. 43
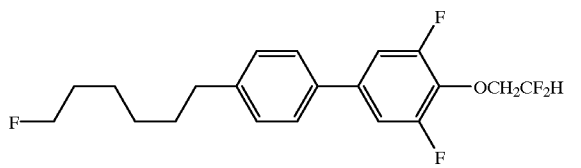
No. 44
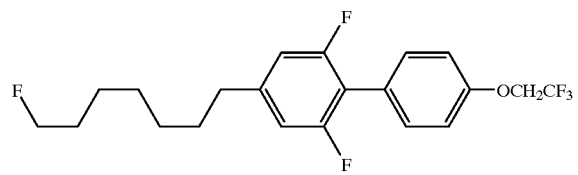
No. 45
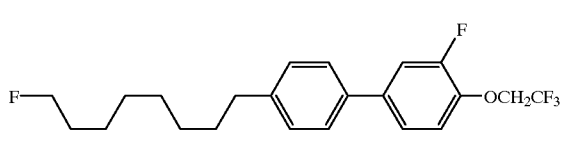
No. 46
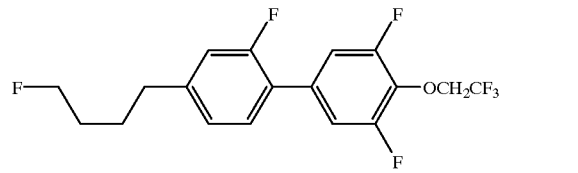
No. 47
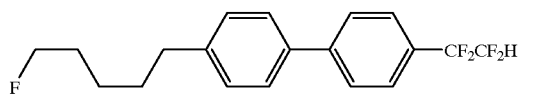
No. 48
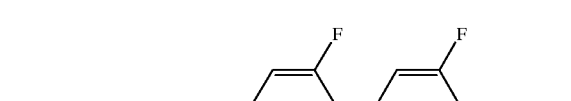
No. 49
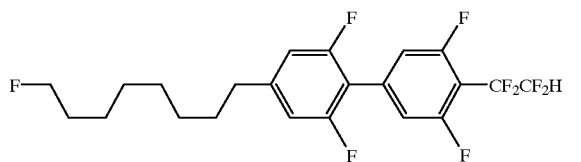
No. 50
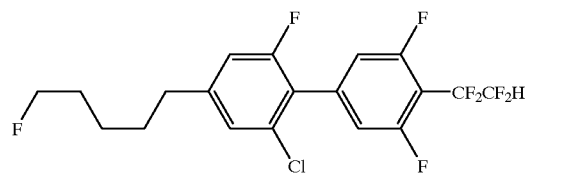
No. 51
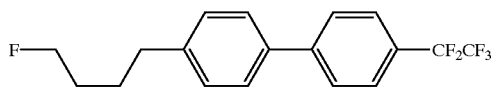
No. 52
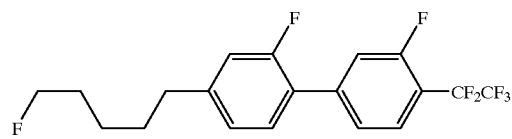

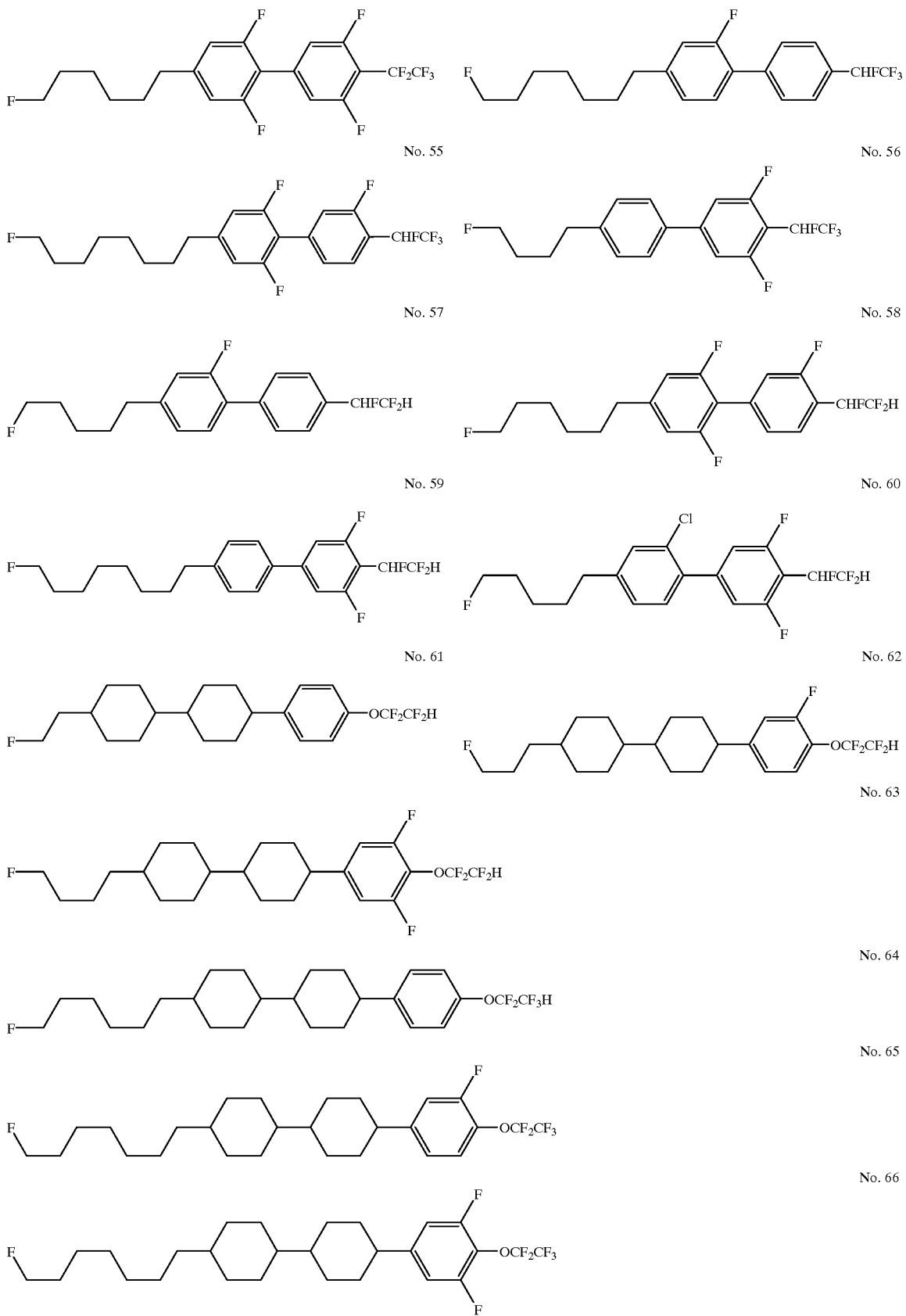

-continued
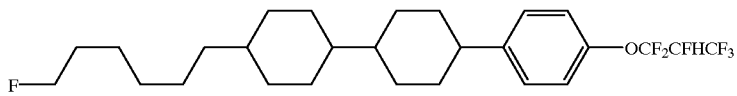
No. 67
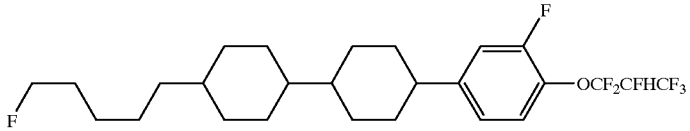
No. 68
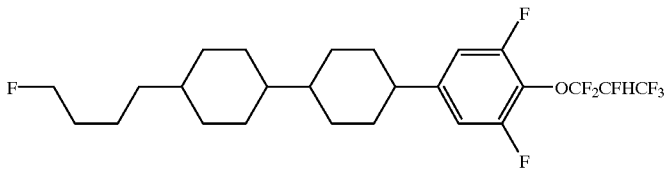
No. 69
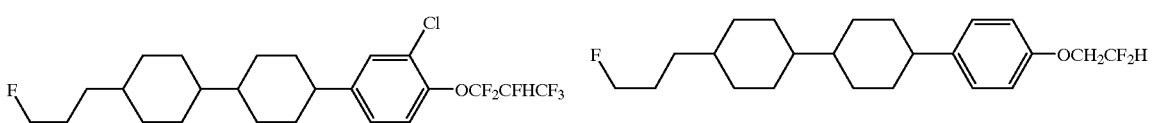
No. 70　　　　　　　　　　　　　　　　　　No. 71
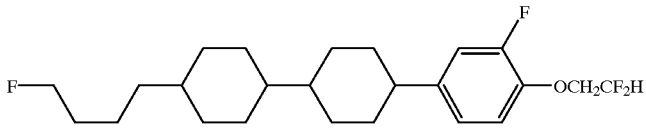
No. 72
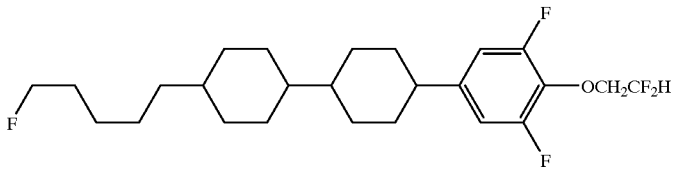
No. 73
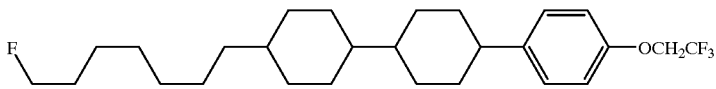
No. 74
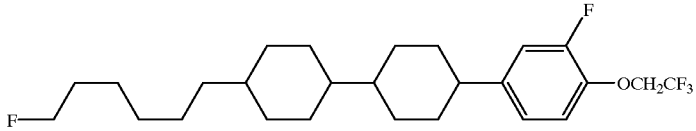
No. 75
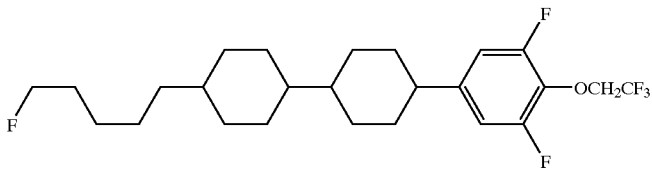
No. 76
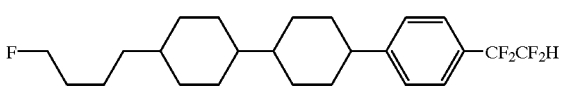
No. 77
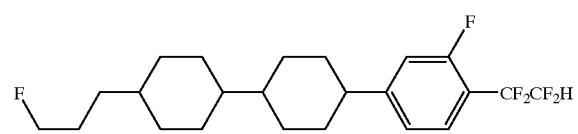
No. 78

-continued
No. 79
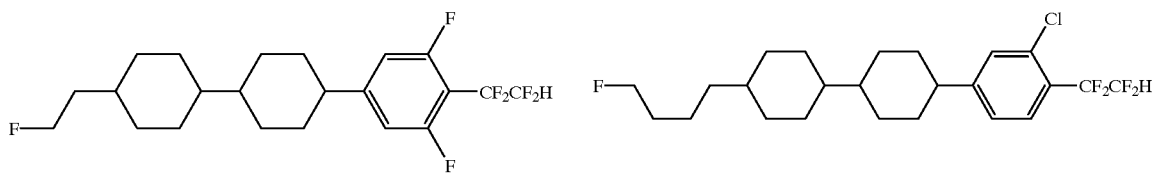
No. 80
No. 81
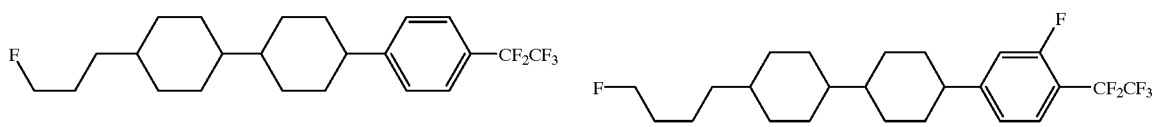
No. 82
No. 83
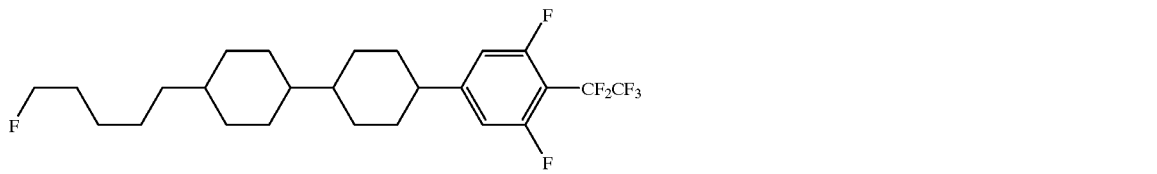
No. 84
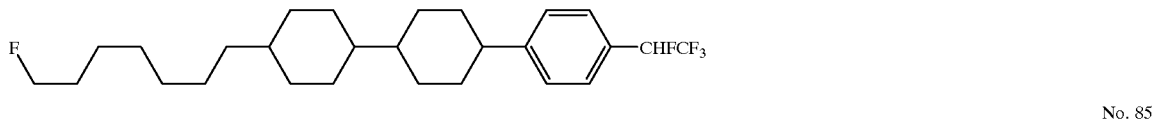
No. 85
No. 86
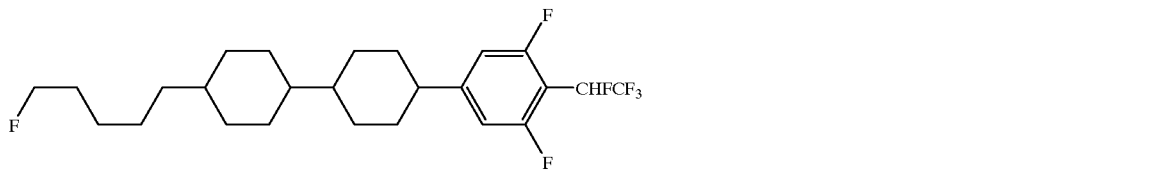
No. 87
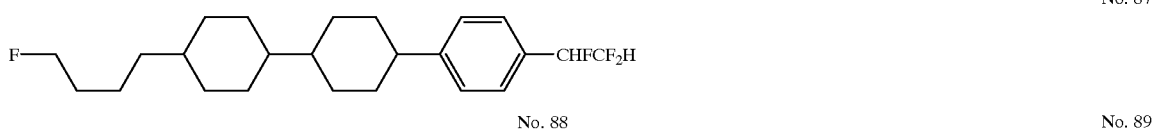
No. 88
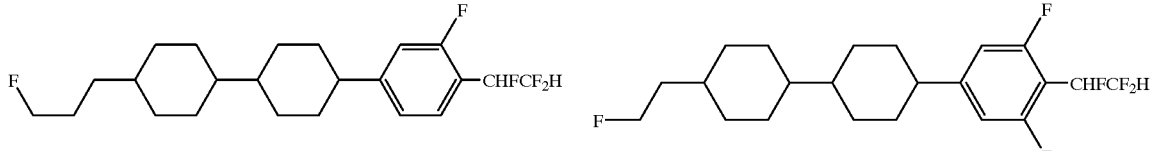
No. 89
No. 90
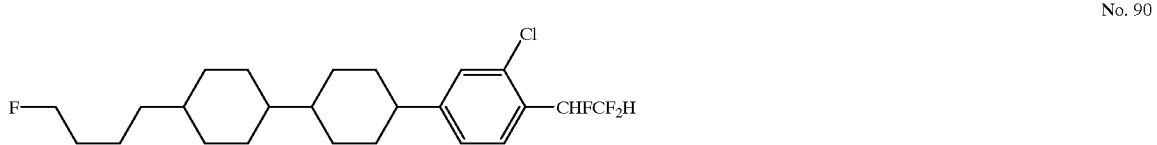
No. 91
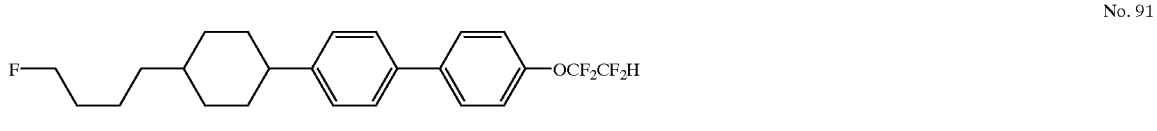

-continued
No. 92
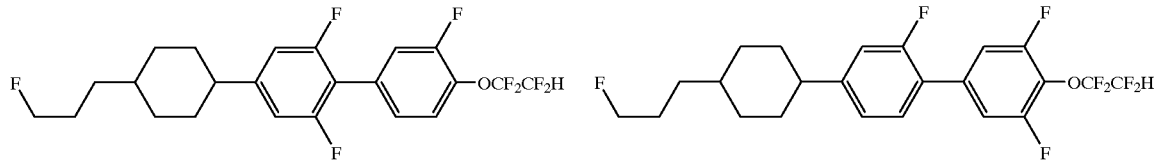
No. 93
No. 94
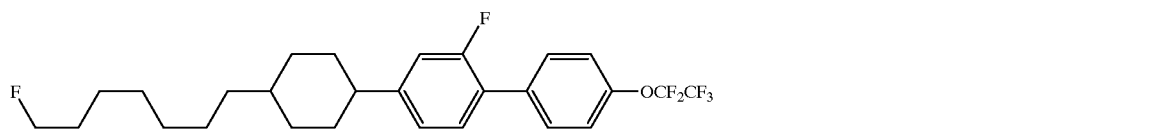
No. 95
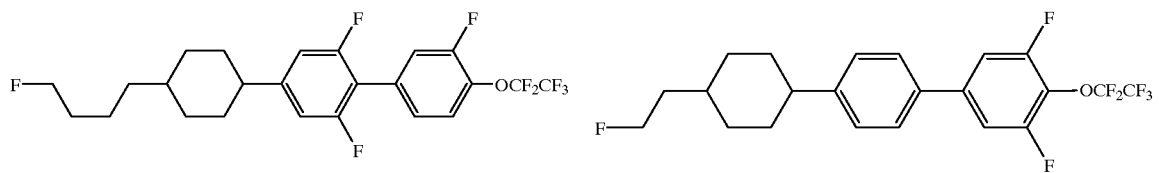
No. 96
No. 97
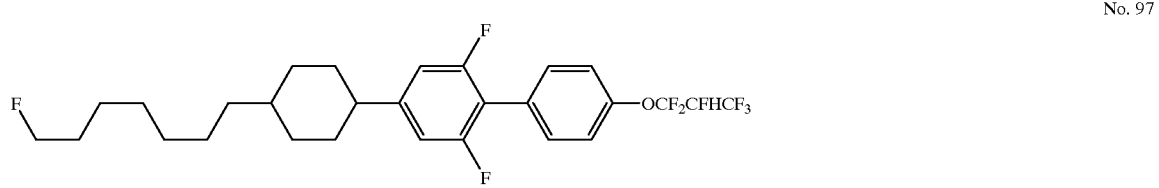
No. 98
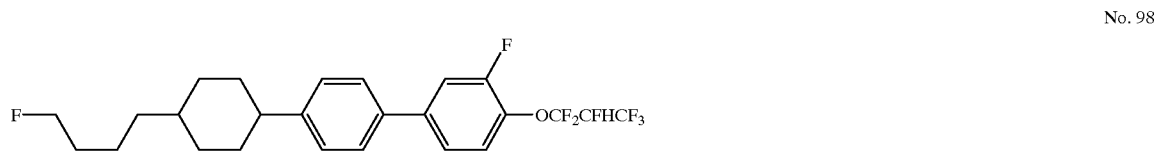
No. 99
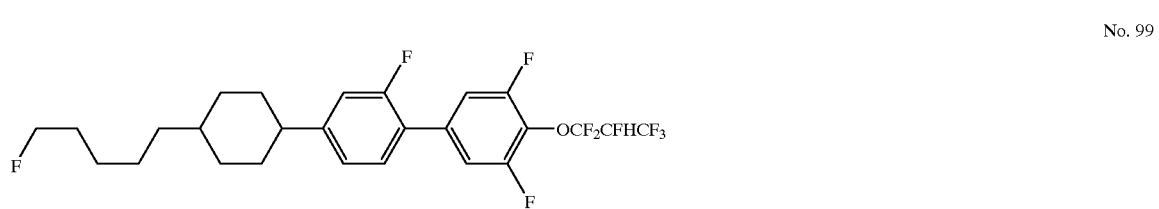
No. 100
No. 101
No. 102
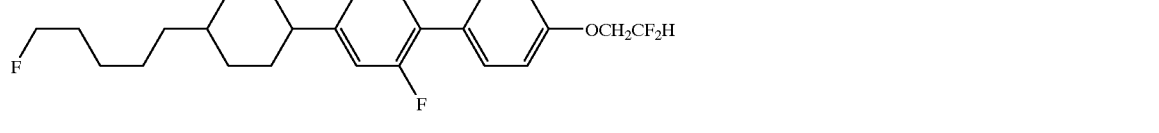
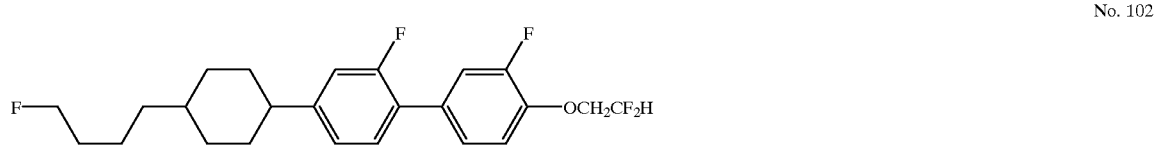

No. 103
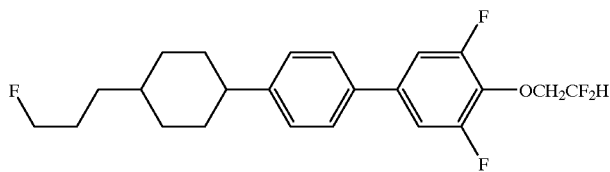
No. 104
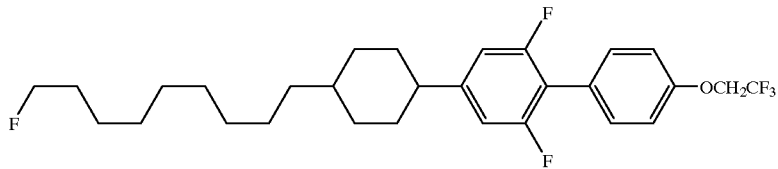
No. 105
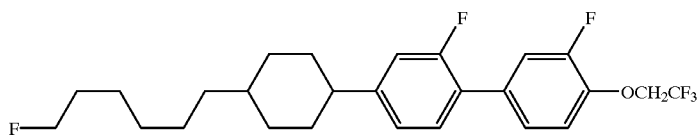
No. 106 No. 107
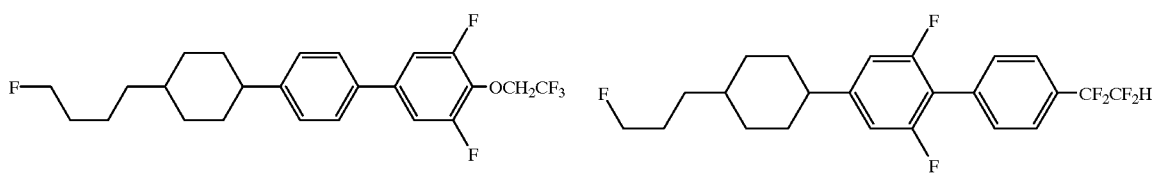
No. 108
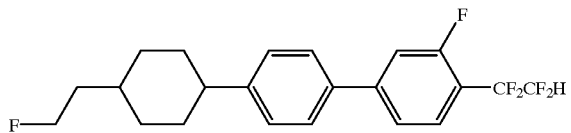
No. 109
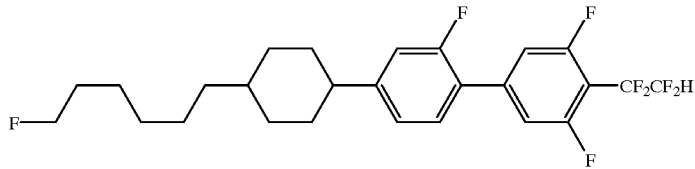
No. 110
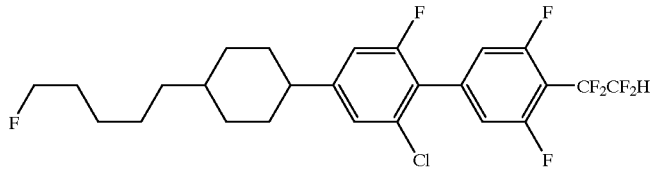
No. 111 No. 112
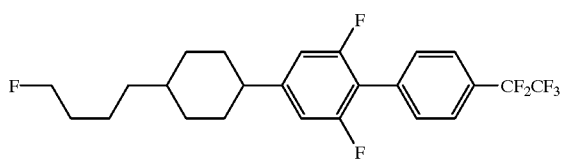 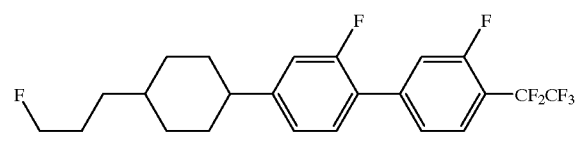

No. 113
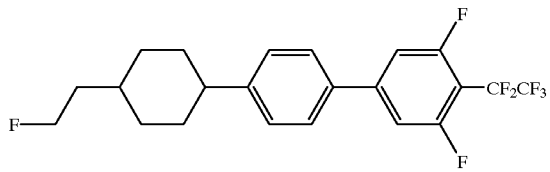
No. 114
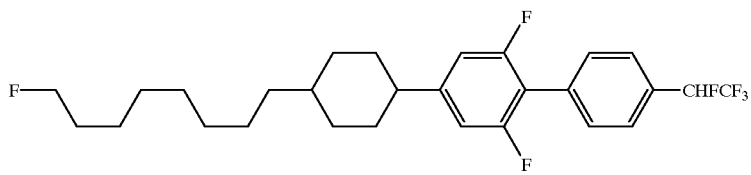
No. 115
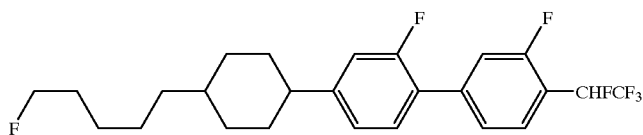
No. 116
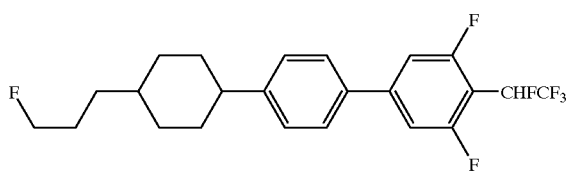
No. 117
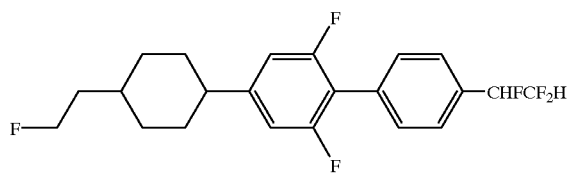
No. 118
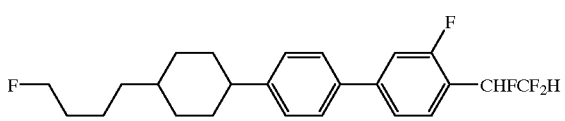
No. 119
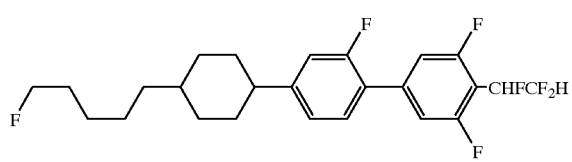
No. 120
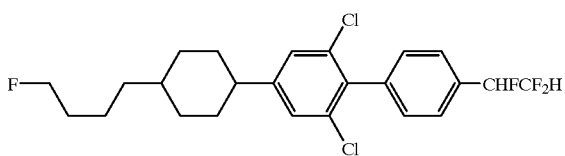
No. 121
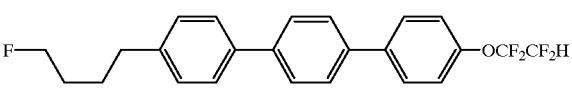
No. 122
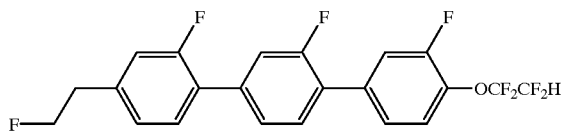
No. 123
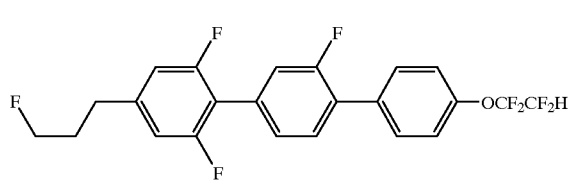
No. 124
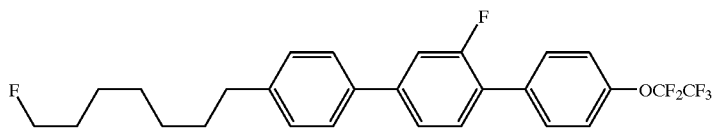

-continued
No. 125
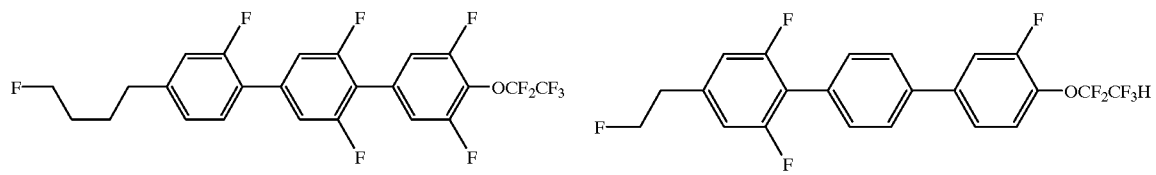
No. 126
No. 127
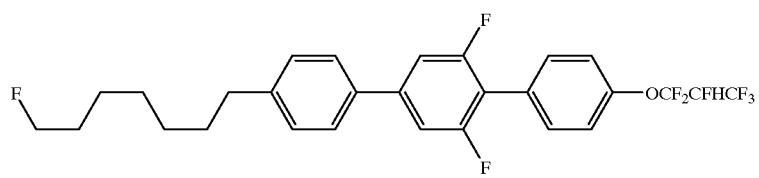
No. 128
No. 129
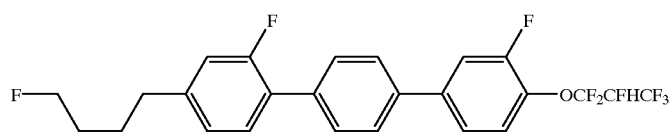
No. 130
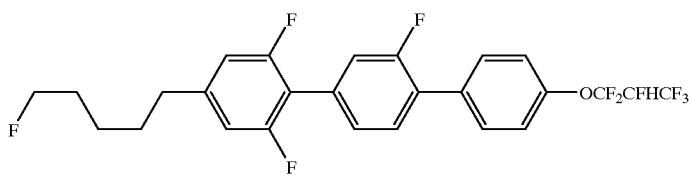
No. 131
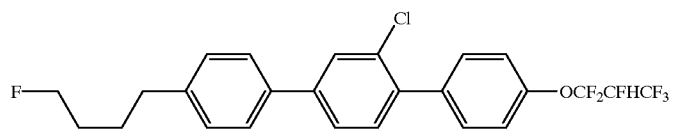
No. 132
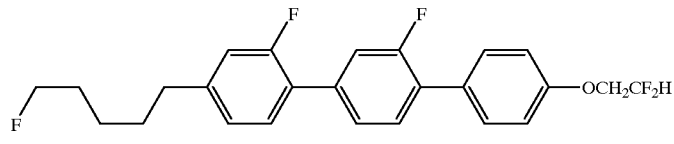
No. 133
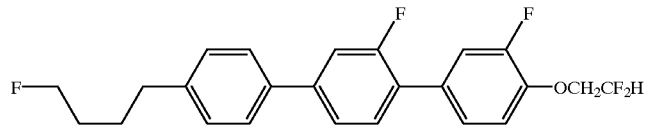
No. 134
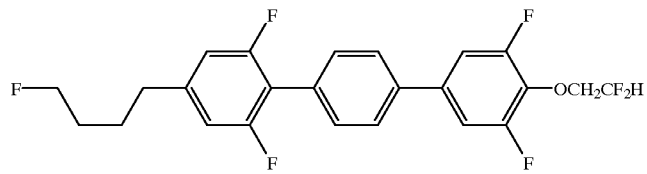
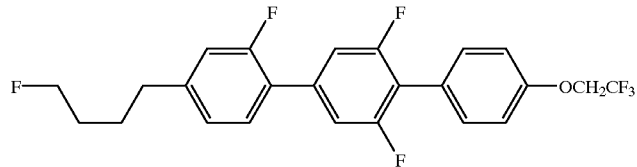

-continued
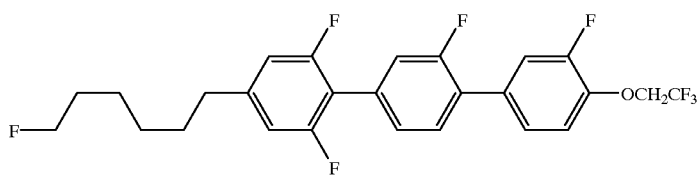
No. 135
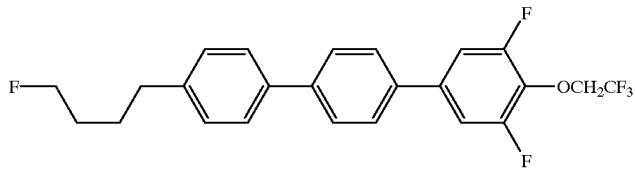
No. 136
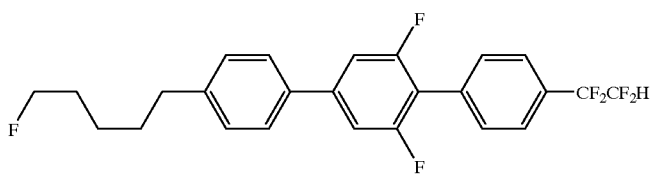
No. 137
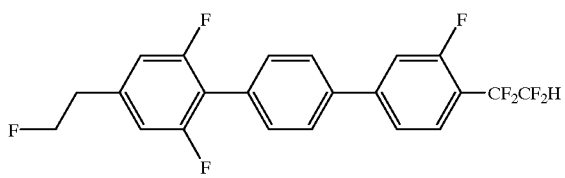
No. 138
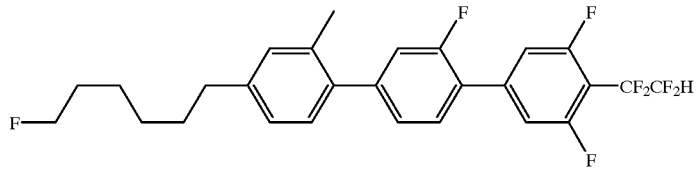
No. 139
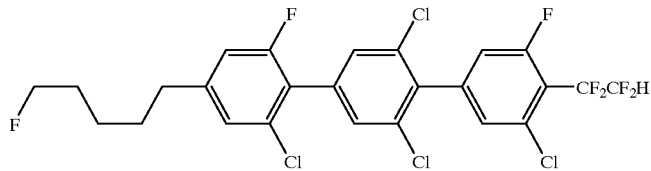
No. 140
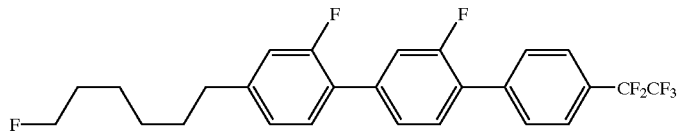
No. 141
No. 142
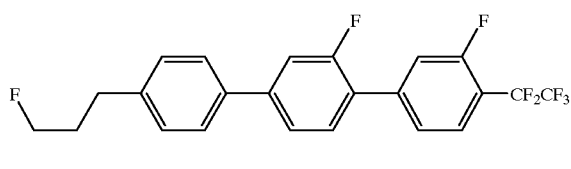
No. 143
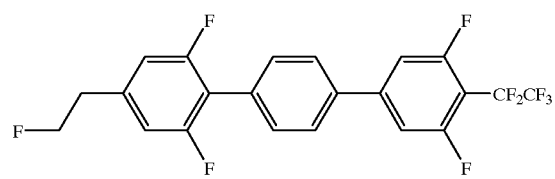
No. 144
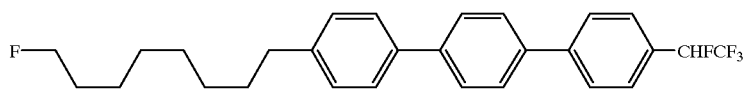

-continued
No. 145
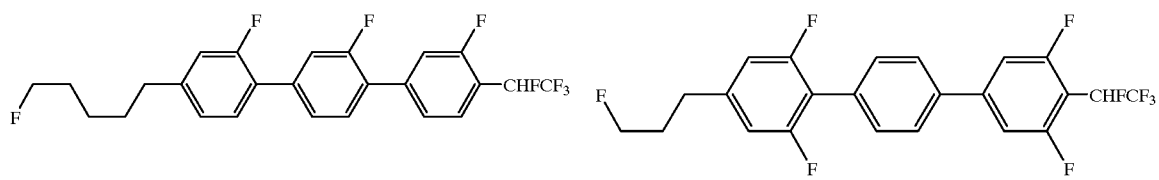
No. 146
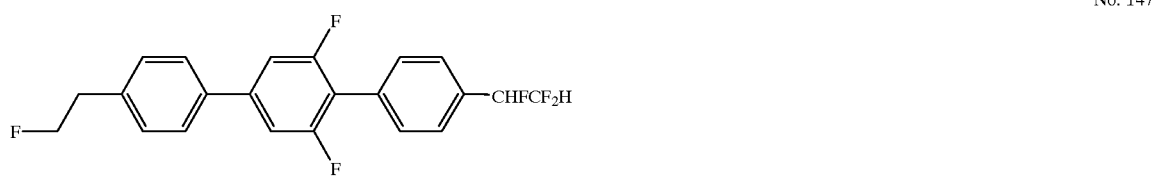
No. 147
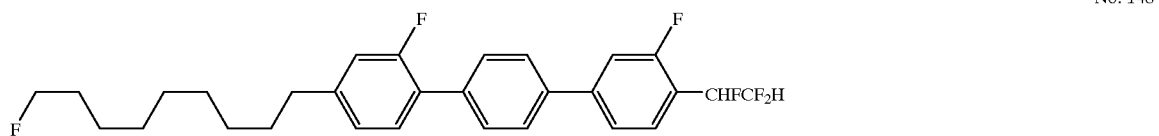
No. 148
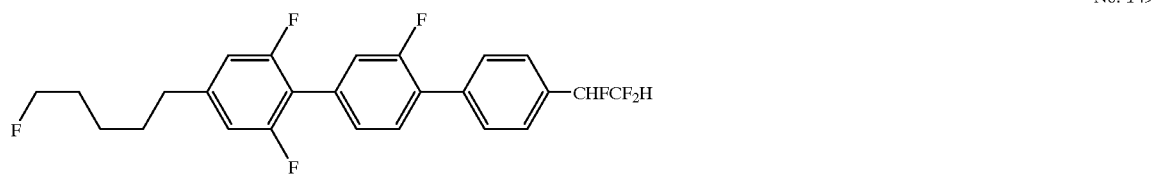
No. 149
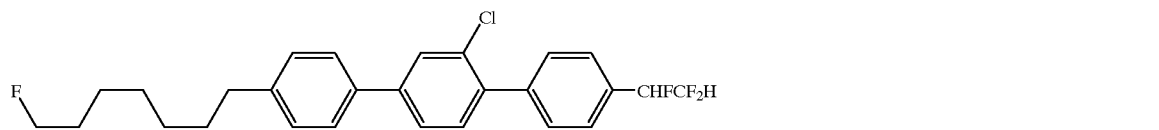
No. 150
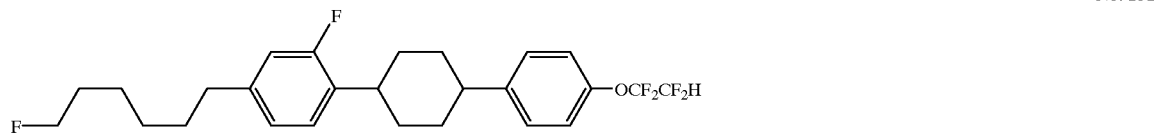
No. 151
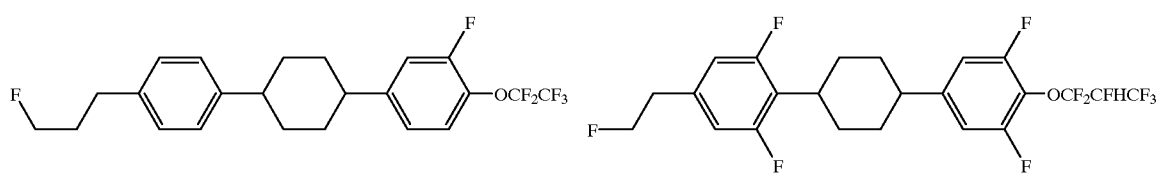
No. 152
No. 153
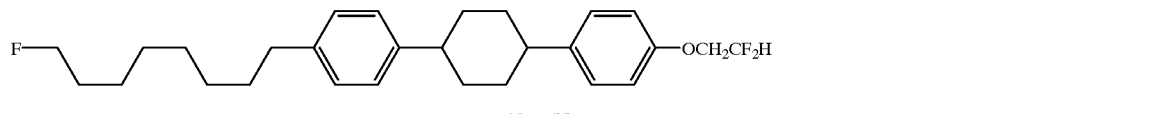
No. 154
No. 155
No. 156
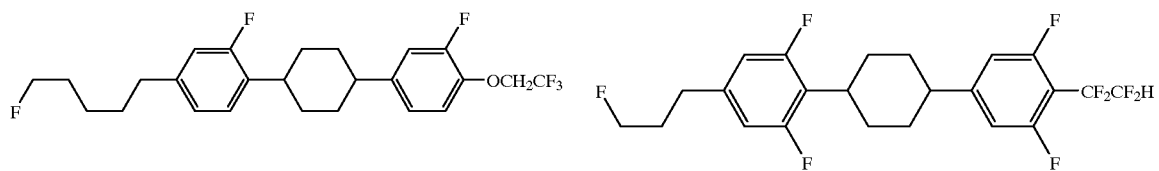

No. 157 – No. 166: (chemical structures)

EXAMPLE 2 (Use Example 1)

Nematic liquid crystal composition comprising the following cyanophenylcyclohexane type liquid crystalline compounds in the content each shown below (hereinafter sometimes referred to as Liquid crystal composition A1)

4-(4-propylcyclohexyl)benzonitrile 24%
4-(4-pentylcyclohexyl)benzonitrile 36%
4-(4-heptylcyclohexyl)benzonitrile 25%
4-(4-(4-pentylcyclohexyl)phenylbenzonitrile 15% had the following characteristics:

Clearing point (TNI): 71.7° C.
Threshold voltage (Vth) at a cell thickness of 8.8 μm: 1.78 V
Δ∈: 10.0
Δn: 0.137

To 85% by weight of this liquid crystal composition A1 was mixed 15% by weight of 1-(4-(3-fluoropropyl)

cyclohexyl)-4-(3-fluoro-4-(1,1,2,2-tetrafluoroethoxy)phenyl)-3,5-difluorobenzene (Compound No. 92) to prepare Liquid crystal composition B1. This composition exhibited nematic phase even after allowed to stand at −20° C. for 30 days, and the characteristics thereof were as follows:

Clearing point (TNI): 69.8° C.

Threshold voltage (Vth) at a cell thickness of 9.3 μm: 1.40 V

Δ∈: 11.0

Δn: 0.124

Further, the values of physical properties of the compound (Compound No. 92) were calculated, by extrapolation from the values of physical properties of each of the liquid crystal compositions described above and the mixing ratio of the compound contained therein, to be as follows:

Clearing point (TNI): 59.0° C.

Δ∈: 11.0

Δn: 0.124

EXAMPLE 3 (Comparative Example 1)

Liquid crystal composition A2 was prepared which comprised the same compounds in the same contents as Composition Example 22 with the exception that a compound of the present invention (Compound No. 92) was changed to 3—HB(F,F)B(F)—OCF$_2$CF$_2$H which is not included in the scope of the present invention. When this Liquid crystal composition A2 was allowed to stand at −20° C., smectic phase was developed in seventh days.

As described above, the liquid crystalline compounds of the present invention are excellent in the miscibility with existing liquid crystalline compounds even at low temperatures, and electrically and chemically stable while having a high voltage holding ratio and a high Δ∈.

INDUSTRIAL APPLICABILITY

Accordingly, when the liquid crystalline compound of the present invention was used as component of liquid crystal compositions, liquid crystal compositions for liquid crystal display devices by which response speed does not become extremely slow in any times and an excellent display is possible can be attained.

What is claimed is:

1. A liquid crystalline compound expressed by the general formula (1)

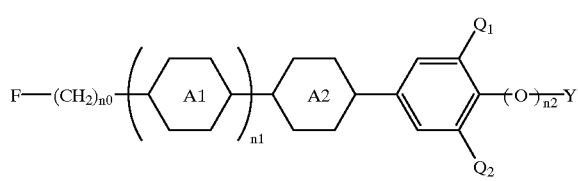

(1)

wherein n0 is an integer of 2 to 10; n1 and n2 are each independently 0 or 1; ring A1 and ring A2 each independently represent a group selected from the groups expressed by any one of the formulas (a) to (g);

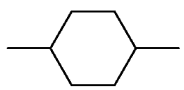
(a)

(b)

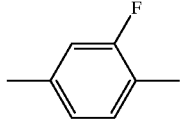
(c)

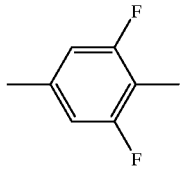
(d)

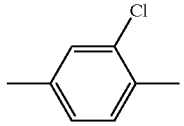
(e)

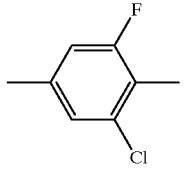
(f)

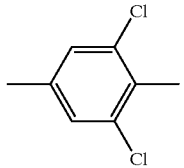
(g)

$Q_1$ and $Q_2$ each independently represent hydrogen atom, fluorine atom, or chlorine atom; and Y represents a fluoroalkyl group having 2 to 7 carbon atoms.

2. The liquid crystalline compound according to claim 1 wherein n1 is 0.

3. The liquid crystalline compound according to claim 1 wherein n1 is 1.

4. The liquid crystalline compound according to claim 1 wherein n2 is 0.

5. The liquid crystalline compound according to claim 1 wherein n2 is 1.

6. The liquid crystalline compound according to claim 1 wherein n1 is 1 and ring A1 is a group selected from the groups expressed by any one of the formulas (a) to (d):

(a) 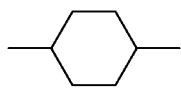

(b) 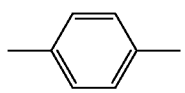

(c) 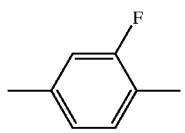

(d) 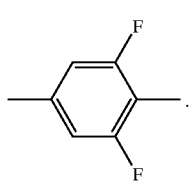

7. A liquid crystal composition comprising at least one liquid crystalline compound defined in any one of claims 1 to 6.

8. A liquid crystal composition comprising, as a first component, at least one liquid crystalline compound defined in any one of claims 1 to 6, and comprising, as a second component, at least one compound selected from the compounds expressed by any one of the general formulas (2), (3), and (4)

(2) 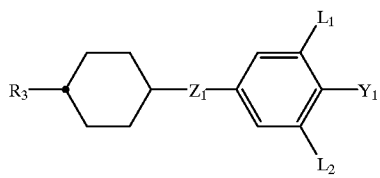

(3) 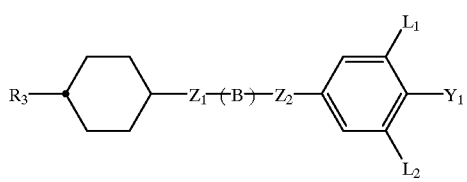

(4) 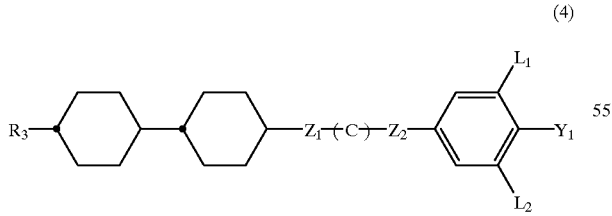

wherein $R_3$, $Y_1$, $L_1$, $L_2$, $Z_1$, and $Z_2$ may be the same or different; $R_3$ represents an alkyl group having 1 to 10 carbon atoms in which alkyl group one or not-adjacent two or more methylene groups may be replaced by oxygen atom or —CH=CH—, and any hydrogen atom may be replaced by fluorine atom; $Y_1$ represents fluorine atom, chlorine atom, $OCF_3$, $OCF_2H$, $CF_3$, $CF_2H$, $CFH_2$, $OCF_2CF_2H$, or $OCF_2CFHCF_3$; $L_1$ and $L_2$ each independently represent hydrogen atom or fluorine atom; $Z_1$ and $Z_2$ each independently represent —$CH_2CH_2$—, —$CH_2CH_2CH_2CH_2$—, —COO—, —$CF_2O$—, —$OCF_2$—, —CH=CH—, or single bond; B represents trans-1,4-cyclohexylene or 1,3-dioxane-2,5-diyl, or 1,4-phenylene in which hydrogen atom on the ring may be replaced by fluorine atom; and C represents trans-1,4-cyclohexylene, or 1,4-phenylene in which hydrogen atom on the ring may be replaced by fluorine atom.

9. A liquid crystal composition comprising, as a first component, at least one liquid crystalline compound defined in any one of claims 1 to 6, and comprising, as a second component, at least one compound selected from the compounds expressed by the general formula (5) and (6)

(5) 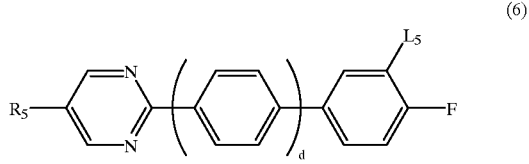

(6)

wherein $R_4$ and $R_5$ each independently represent an alkyl group having 1 to 10 carbon atoms in which alkyl group one or not-adjacent two or more methylene groups may be replaced by oxygen atom or —CH=CH—, and any hydrogen atom may be replaced by fluorine atom; $Y_2$ represents —CN group or —C≡C—CN; E represents trans-1,4-cyclohexylene, 1,4-phenylene, 1,3-dioxane-2,5-diyl, or pyrimidine-2,5-diyl; G represents trans-1,4-cyclohexylene, 1,4-phenylene in which hydrogen atom on the ring may be replaced by fluorine atom, or pyrimidine-2,5-diyl; H represents trans-1,4-cyclohexylene or 1,4-phenylene; $Z_3$ represents —$CH_2CH_2$— —COO—, or single bond; $L_3$, $L_4$, and $L_5$ each independently represent hydrogen atom or fluorine atom; and b, c, and d are each independently 0 or 1.

10. A liquid crystal composition comprising, as a first component, at least one liquid crystalline compound defined in any one of claims 1 to 6, comprising, as a second component, at least one compound selected from the compounds expressed by any one of the general formulas (2), (3), and (4)

(2)

(3)

(4)

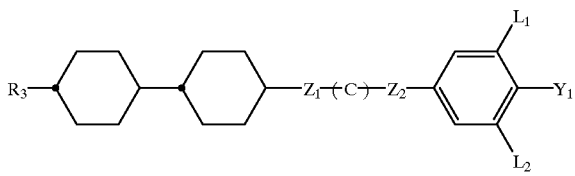

wherein $R_3$, $Y_1$, $L_1$, $L_2$, $Z_1$, and $Z_2$ may be the same or different; $R_3$ represents an alkyl group having 1 to 10 carbon atoms in which alkyl group one or not-adjacent two or more methylene groups may be replaced by oxygen atom or —CH═CH—, and any hydrogen atom may be replaced by fluorine atom; $Y_1$ represents fluorine atom, chlorine atom, $OCF_3$, $OCF_2H$, $CF_3$, $CF_2H$, $CFH_2$, $OCF_2CF_2H$, or $OCF_2CFHCF_3$; $L_1$ and $L_2$ each independently represent hydrogen atom or fluorine atom; $Z_1$ and $Z_2$ each independently represent —CH$_2$CH$_2$—, —CH$_2$CH$_2$CH$_2$—, —COO—, —CF$_2$O—, —OCF$_2$—, —CH═CH—, or single bond; B represents trans-4-cyclohexylene or 1,3-dioxane-2,5-diyl, or 1,4-phenylene in which hydrogen atom on the ring may be replaced by fluorine atom; and C represents trans-1,4-cyclohexylene, or 1,4-phenylene in which hydrogen atom on the ring may be replaced by fluorine atom, and comprising, as a third component, at least one compound selected from the compounds expressed by any one of the general formulas (7), (8), and (9)

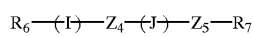 (7)

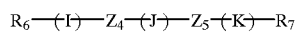 (8)

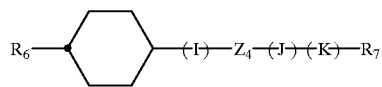 (9)

wherein $R_6$, $R_7$, I, J, and K may be the same or different; $R_6$ and $R_7$ each independently represent an alkyl group having 1 to 10 carbon atoms in which alkyl group one or not-adjacent two or more methylene groups may be replaced by oxygen atom or —CH═CH—, and any hydrogen atom may be replaced by fluorine atom; I, J, and K each independently represent trans-1,4-cyclohexylene or pyrimidine-2,5-diyl, or 1,4-phenylene in which hydrogen atom on the ring may be replaced by fluorine atom; and $Z_4$ and $Z_5$ each independently represent —C≡C—, —COO—, —CH$_2$CH$_2$—, —CH═CH—, or single bond.

11. A liquid crystal composition comprising, as a first component, at least one liquid crystalline compound defined in any one of claims 1 to 6, comprising, as a second component, at least one compound selected from the compounds expressed by the general formula (5) and (6)

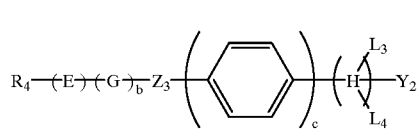 (5)

(6)

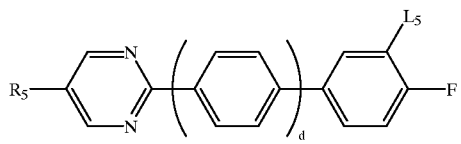

wherein $R_4$ and $R_5$ each independently represent an alkyl group having 1 to 10 carbon atoms in which alkyl group one or not-adjacent two or more methylene groups may be replaced by oxygen atom or —CH═CH—, and any hydrogen atom may be replaced by fluorine atom; $Y_2$ represents —CN group or —C≡C—CN; E represents trans-1,4-cyclohexylene, 1,4-phenylene, 1,3-dioxane-2,5-diyl, or pyrimidine-2,5-diyl; G represents trans-1,4-cyclohexylene, 1,4-phenylene in which hydrogen atom on the ring may be replaced by fluorine atom, or pyrimidine-2,5-diyl; H represents trans-1,4-cyclohexylene or 1,4-phenylene; $Z_3$ represents —CH$_2$CH$_2$— —COO—, or single bond; $L_3$, $L_4$, and $L_5$ each independently represent hydrogen atom or fluorine atom; and b, c, and d are each independently 0 or 1; and comprising, as a third component, at least one compound selected from the compounds expressed by any one of the general formulas (7), (8), and (9)

 (7)

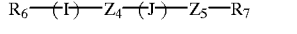 (8)

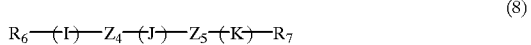 (9)

wherein $R_6$, $R_7$, I, J, and K may be the same or different; $R_6$ and $R_7$ each independently represent an alkyl group having 1 to 10 carbon atoms in which alkyl group one or not-adjacent two or more methylene groups may be replaced by oxygen atom or —CH═CH—, and any hydrogen atom may be replaced by fluorine atom; I, J, and K each independently represent trans-1,4-cyclohexylene or pyrimidine-2,5-diyl, or 1,4-phenylene in which hydrogen atom on the ring may be replaced by fluorine atom; and $Z_4$ and $Z_5$ each independently represent —C≡C—, —COO—, —CH$_2$CH$_2$—, —CH═CH—, or single bond.

12. A liquid crystal composition comprising, as a first component, at least one liquid crystalline compound defined in any one of claims 1 to 6, comprising, as a part of a second component, at least one compound selected from the compounds expressed by any one of the general formulas (2), (3), and (4)

(2)

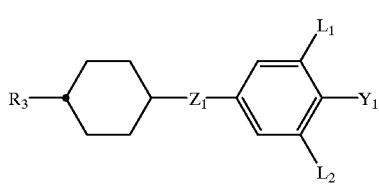

(3)

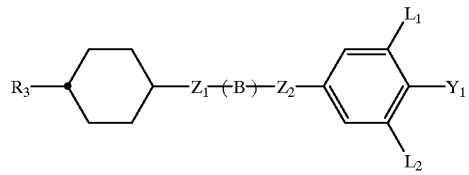

(4)

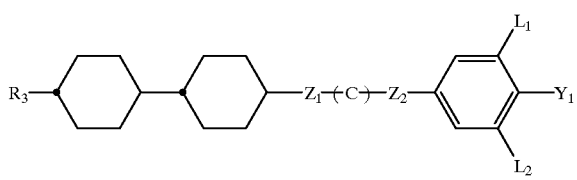

wherein $R_3$, $Y_1$, $L_1$, $L_2$, $Z_1$, and $Z_2$ may be the same or different; $R_3$ represents an alkyl group having 1 to 10 carbon atoms in which alkyl group one or not-adjacent two or more methylene groups may be replaced by oxygen atom or —CH=CH—, and any hydrogen atom may be replaced by fluorine atom; $Y_1$ represents fluorine atom, chlorine atom, OCF$_3$, OCF$_2$H, CF$_3$, CF$_2$H, CFH$_2$, OCF$_2$CF$_2$H, or OCF$_2$CFHCF$_3$; $L_1$ and $L_2$ each independently represent hydrogen atom or fluorine atom; $Z_1$ and $Z_2$ each independently represent —CH$_2$CH$_2$—, —CH$_2$CH$_2$CH$_2$CH$_2$—, —COO—, —CF$_2$O—, —OCF$_2$—, —CH=CH—, or single bond; B represents trans-1,4-cyclohexylene or 1,3-dioxane-2,5-diyl, or 1,4-phenylene in which hydrogen atom on the ring may be replaced by fluorine atom; and C represents trans-1,4-cyclohexylene, or 1,4-phenylene in which hydrogen atom on the ring may be replaced by fluorine atom; comprising, as another part of the second component, at least one compound selected from the compounds expressed by the general formula (5) and (6)

(5)

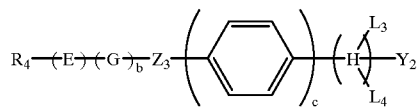

(6)

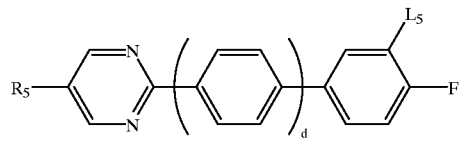

wherein $R_4$ and $R_5$ each independently represent an alkyl group having 1 to 10 carbon atoms in which alkyl group one or not-adjacent two or more methylene groups may be replaced by oxygen atom or —CH=CH—, and any hydrogen atom may be replaced by fluorine atom; $Y_2$ represents —CN group or —C≡C—CN; E represents trans-1,4-cyclohexylene, 1,4-phenylene, 1,3-dioxane-2,5-diyl, or pyrimidine-2,5-diyl; G represents trans-1,4-cyclohexylene, 1,4-phenylene in which hydrogen atom on the ring may be replaced by fluorine atom, or pyrimidine-2,5-diyl; H represents trans-1,4-cyclohexylene or 1,4-phenylene; $Z_3$ represents —CH$_2$CH$_2$— —COO—, or single bond; $L_3$, $L_4$, and $L_5$ each independently represent hydrogen atom or fluorine atom; and b, c, and d are each independently 0 or 1; and comprising, as a third component, at least one compound selected from the compounds expressed by any one of the general formulas (7), (8), and (9)

(7)

(8)

(9)

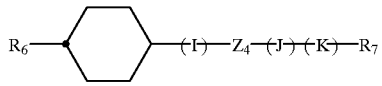

wherein $R_6$, $R_7$, I, J, and K may be the same or different; $R_6$ and $R_7$ each independently represent an alkyl group having 1 to 10 carbon atoms in which alkyl group one or not-adjacent two or more methylene groups may be replaced by oxygen atom or —CH=CH—, and any hydrogen atom may be replaced by fluorine atom; I, J, and K each independently represent trans-1,4-cyclohexylene or pyrimidine-2,5-diyl, or 1,4-phenylene in which hydrogen atom on the ring may be replaced by fluorine atom; and $Z_4$ and $Z_5$ each independently represent —C≡C—, —COO—, —CH$_2$CH$_2$—, —CH=CH—, or single bond.

13. A liquid crystal composition according to claim 7 wherein the liquid crystal composition further comprises an optically active compound.

14. A liquid crystal display device comprising a liquid crystal composition defined in claim 7.

15. A liquid crystal display device comprising a liquid crystal composition defined in claim 13.

* * * * *

UNITED STATES PATENT AND TRADEMARK OFFICE
CERTIFICATE OF CORRECTION

PATENT NO.  : 6,248,260 B1
DATED       : June 19, 2001
INVENTOR(S) : Yasuhiro Haseba et al.

It is certified that error appears in the above-identified patent and that said Letters Patent is hereby corrected as shown below:

Column 49,
Between lines 60 and 65, change "$H^+$" to -- $H_2$ --.

Column 81,
Change the structure of the fifth compound (No. 139) to:

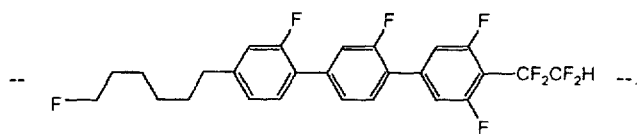

Signed and Sealed this

Ninth Day of April, 2002

Attest:

JAMES E. ROGAN
*Attesting Officer*     *Director of the United States Patent and Trademark Office*